United States Patent

Nozaki

[19]

[11] Patent Number: 6,038,514
[45] Date of Patent: Mar. 14, 2000

[54] MATERIALS DESIGN SYSTEM AND STORAGE MEDIUM STORING COMPUTER PROGRAM FOR CAUSING COMPUTER SYSTEM TO ANALYZE STABLE STRUCTURE OR DYNAMIC BEHAVIOR OF SYSTEM AT ATOMIC OR MOLECULAR LEVEL TO ASSIST MATERIALS DESIGN BASED ON THIS ANALYSIS

[75] Inventor: Hanae Nozaki, Yokohama, Japan

[73] Assignee: Kabushiki Kaisha Toshiba, Kawasaki, Japan

[21] Appl. No.: 08/909,684

[22] Filed: Aug. 12, 1997

[30]   Foreign Application Priority Data

Aug. 13, 1996 [JP] Japan ................................. 8-213572
Jul. 18, 1997 [JP] Japan ................................. 9-194035

[51] Int. Cl.[7] ............................. G06F 17/22; G06F 17/50
[52] U.S. Cl. ............................ 702/27; 702/33; 395/500.27
[58] Field of Search .................... 702/27, 22, 28, 702/30, 31, 23, 32; 395/500.32, 500.33

[56]   References Cited

U.S. PATENT DOCUMENTS 5,241,470  8/1993  Lee et al. .................................. 702/27
5,265,030  11/1993 Skalnick et al. .................... 395/500.32
5,553,004  9/1996  Gronbech-Jensen et al. .......... 364/496

OTHER PUBLICATIONS

Wilson; "Simulation of Liquids and Solids" Chemistry by Computer (Plenum Press 1986) pp. 135–139.
G. Makov et al.; "Periodic Boundary Conditions in ab initio Calculations" Physical Review B, vol. 51, No. 7, Feb. 15, 1995, pp. 4014–4022.

*Primary Examiner*—Marc S. Hoff
*Assistant Examiner*—Bryan Bui
*Attorney, Agent, or Firm*—Finnegan, Henderson, Farabow, Garrett & Dunner, L.L.P.

[57]   ABSTRACT

Disclosed is a materials design system for obtaining the structural stability or dynamic behavior of an aperiodic system ($S^2$), which includes a reference system $S^0$ processing unit (1-1), an aperiodic system $S^2$ processing unit (1-2), an interatomic potential processing unit (1-3), a reference system $S^0$ calculation unit (1-4), an aperiodic system $S^2$ calculation unit (1-5), an MM calculation unit (1-6) for analyzing the stable structure, and an MD calculation unit (1-7) for analyzing the dynamic behavior. The structure of the aperiodic system ($S^2$) is described on the basis of a deviation from a reference system ($S^0$). When the potential energy of the aperiodic system ($S^2$) and the force acting on each atom or each molecule of the aperiodic system ($S^2$) are to be calculated, calculation is performed within a unit cell of the reference system ($S^0$) and a predetermined range (region where lattice relaxation is taken into consideration) containing the disorder in the aperiodic system ($S^2$). According to this arrangement, in materials design, the stable structure or dynamic behavior of a system containing a disorder (aperiodic system ($S^2$)) can be efficiently calculated without approximation.

14 Claims, 22 Drawing Sheets

CORRESPONDENCE LIST [$S^0 \leftrightarrow S^2$]

| REFERENCE SYSTEM $S^0$ (WITH PERIODICITY) | | APERIODIC SYSTEM $S^2$ (WITHOUT PERIODICITY) | |
|---|---|---|---|
| | ATOMIC NUMBER $(h, \zeta)$ | SERIAL NUMBER $(i)$ | IMPURITY NUMBER $(\sigma)$ |
| FUNDAMENTAL CELL ($\zeta=0$) | (1, 0) | (1) | |
| | (2, 0) | (2) | (1) |
| | (3, 0) | (3) | |
| | (4, 0) | (4) | IMPURITY ATOM |
| | (4, 1) | (5) | |
| | (1, 2) | (6) | |
| | (2, 2) | (7) | |
| | (3, 2) | (8) | |
| | (4, 2) | (9) | |
| | (1, 3) | (10) | |
| | (3, 3) | (11) | |
| | (4, 3) | (12) | |
| | (2, 4) | (13) | |
| | (4, 4) | (14) | |
| | (1, 5) | (15) | |
| | (2, 5) | (16) | |
| | (3, 5) | (17) | |
| | (4, 5) | (18) | |
| | (1, 7) | (19) | |
| | (2, 7) | (20) | |
| | (1, 8) | (21) | |

FIG. 4

| REFERENCE SYSTEM $S^0$ | APERIODIC SYSTEM $S^2$ | |
|---|---|---|
| $A^0(h\zeta) \neq 0$ | $A^2(i) \neq 0$ (AND $A^2(i) \neq A^0(h\zeta)$) | ···SUBSTITUTIONAL IMPURITY ATOM |
| $A^0(h\zeta) \neq 0$ | $A^2(i) \neq 0$ | ···INTERSTITIAL IMPURITY ATOM |
| $A^0(h\zeta) = 0$ | $A^2(i) = 0$ | ···DEFECT |

FIG. 5

| CORRESPONDENCE LIST $[S^0 \leftrightarrow S^1]$ | CORRESPONDENCE LIST $[S^1 \leftrightarrow S^2]$ | | |
|---|---|---|---|
| REFERENCE SYSTEM $S^0$ ATOMIC NUMBER $(h, \zeta)$ | PERIODIC SYSTEM $S^1$ ATOMIC NUMBER $(h, \xi)$ | APERIODIC SYSTEM $S^2$ SERIAL NUMBER $(i)$ | IMPURITY NUMBER $(\sigma)$ |
| FUNDAMENTAL CELL ($\zeta=0$) (1, 0) (2, 0) (3, 0) (4, 0) | (1, 0) (2, 0) (3, 0) (4, 0) | (1) (2) (3) (4) | (1) IMPURITY ATOM |
| (1, 1) (2, 1) (3, 1) (4, 1) | (5, 0) (6, 0) (7, 0) (8, 0) | (5) | |
| (1, 2) (2, 2) (3, 2) (4, 2) | (9, 0) (10, 0) (11, 0) (12, 0) | (6) (7) (8) (9) | |
| (1, 3) (2, 3) (3, 3) (4, 3) | (13, 0) (14, 0) (15, 0) (16, 0) | (10) (11) (12) | |
| (1, 4) (2, 4) (3, 4) (4, 4) | (17, 0) (18, 0) (19, 0) (20, 0) | (13) (14) | |
| (1, 5) (2, 5) (3, 5) (4, 5) | (21, 0) (22, 0) (23, 0) (24, 0) | (15) (16) (17) (18) | |
| (1, 6) (2, 6) (3, 6) (4, 6) | (25, 0) (26, 0) (27, 0) (28, 0) | | |
| (1, 7) (2, 7) (3, 7) (4, 7) | (29, 0) (30, 0) (31, 0) (32, 0) | (19) (20) | |
| (1, 8) (2, 8) (3, 8) (4, 8) | (33, 0) (34, 0) (35, 0) (36, 0) | (21) | |

FIG. 18

| PERIODIC SYSTEM $S^1$ | APERIODIC SYSTEM $S^2$ | |
|---|---|---|
| $A^1(k\xi) \neq 0$ <br><br> $m^1(k\xi) \neq 0 (\neq \infty)$ | $A^2(i) \neq 0$ <br> (AND $A^2(i) \neq A^1(k\xi)$) <br> $m^2(i) \neq 0 (\neq \infty)$ <br> (AND $m^2(i) \neq m^1(k\xi)$) | SUBSTITUTIONAL IMPURITY ATOM |
| $A^1(k\xi) = 0$ <br> $m^1(k\xi) = \infty$ | $A^2(i) \neq 0$ <br> $m^2(i) \neq 0 (\neq \infty)$ | INTERSTITIAL IMPURITY ATOM |
| $A^1(k\xi) \neq 0$ <br> $m^1(k\xi) \neq 0 (\neq \infty)$ | $A^2(i) = 0$ <br> $m^2(i) = \infty$ | DEFECT |

FIG. 19

MATERIALS DESIGN SYSTEM AND
STORAGE MEDIUM STORING COMPUTER
PROGRAM FOR CAUSING COMPUTER
SYSTEM TO ANALYZE STABLE
STRUCTURE OR DYNAMIC BEHAVIOR OF
SYSTEM AT ATOMIC OR MOLECULAR
LEVEL TO ASSIST MATERIALS DESIGN
BASED ON THIS ANALYSIS

BACKGROUND OF THE INVENTION

The present invention relates to an assist system (CAD system) for designing a substance or a material using a computer and, more particularly, to MM (Molecular Mechanics) calculation and MD (Molecular Dynamics) calculation.

As is generally known, when a substance or a material is to be designed using a computer, the structural stability or dynamic behavior of a crystal system is analyzed using MM (Molecular Mechanics) calculation or MD (Molecular Dynamics) calculation.

In MD calculation, a change over time in motion of atoms or molecules at a finite temperature is tracked in accordance with a Newton's equation. This is one of essential techniques for substance/material design as a means for checking the microscopic behavior of a system (reference [1]: Akira Ueda, "Computer Simulation", Asakura Shoten (1990)).

MM calculation is a method of analyzing the most stable structure of a system and corresponds to MD calculation at the absolute zero (T=0 K) (reference [2]: Isao Okada and Eiji Osawa, "Introduction to Molecular Simulation", Kaibundo (1989)).

The MM calculation and MD calculation can be applied to both an infinite system (e.g., a crystal) and an isolated system (e.g., a molecule). The MM/MD calculation of the present invention is directed to the infinite system.

The "infinite system" means a system having a sufficient range at the atomic/molecular level, i.e., a solid or liquid such as a crystal, an amorphous substance, or a liquid crystal. Since such an infinite system cannot be directly handled by computer simulation, a cell (unit cell) having a predetermined size and called a unit cell is set in the infinite system. Accordingly, the infinite system is perceived as a system in which the unit cells are periodically and three-dimensionally arranged.

With this arrangement, computer simulation for the infinite system can be performed only by performing calculation while setting a periodic boundary condition for the unit cell.

This technique using the periodic boundary condition is supposed to be adequate for a crystal system having a periodicity. However, this method is also applied, as an approximation method, to a system whose periodicity disappears because of impurities.

The impurity is the major factor (disorder) for canceling the periodicity. The impurity here means a substitutional/interstitial impurity atom or a defect (the three types of disorders will be referred to as "impurity atoms" hereinafter). A set of one or more impurity atoms existing relatively close to each other in a crystal is called an "impurity". In addition to the impurity, a destruction phenomenon or the like can also be considered as a disorder. In this specification, an infinite system in which such disorders are distributed at a relatively low concentration (a system in which there are almost no interactions between disorders) is defined as an "aperiodic system".

When the disorder is an impurity, the "aperiodic system" can be regarded as a "system containing an isolated impurity". The "system containing an isolated impurity" means an infinite system having only one "impurity", or an infinite system having a plurality of impurities which are sufficiently separated from each other and do not interact each other.

In other words, in such a system, the content of the "impurity" is very low. An example is a defect in a (compound) semiconductor. This defect is known as a DX center which gives a deep impurity level near the center of the energy gap of the semiconductor and largely affects the device characteristics of a semiconductor laser or the like.

In analyzing the structural stability or dynamic behavior of such an "aperiodic system" on the basis of the above-described MM calculation or MD calculation, a method of performing simulation while giving prominence on one unit cell under the "periodic boundary condition" is generally known as a "supercell method".

In the supercell method, only one disorder is arranged in the unit cell, and a sufficiently large unit cell size is set, thereby approximately describing a state wherein disorders do not interact each other. More specifically, in the supercell method, to realize the state of the above-described aperiodic system (when the disorder is an "impurity", "a system containing an isolated impurity"), normally, only one disorder is set in the unit cell. However, this disorder is automatically arranged in peripheral unit cells (to be referred to as "image cells") because of the periodic boundary condition. To perform proper calculation while minimizing interaction with these disorders, the unit cell size must be as large as possible.

However, in the supercell method, the unit cell size must be determined in advance before the start of simulation (the size cannot be changed during simulation), and the size is often determined (to be relatively small) in consideration of the balance between the calculation accuracy and the calculation time.

When the supercell method is used, the aperiodic system can be handled within the same framework as that of the calculation method for a periodic system. For this reason, the supercell method is generally used as a convenient method for MD calculation or MM calculation.

To perform MD calculation or MM calculation using the supercell method, the force acting on each constituent atom of the system must be calculated in each step of repetitive calculation of MM calculation or at each time (one step of repetitive calculation) of MD calculation on the basis of the interatomic interaction. The potential energy of the system is often simultaneously calculated on the basis of the interatomic interaction. When the interatomic interaction is a long-range interaction, calculation of the force or energy slowly converges. Particularly, for a Coulomb interaction described as an $r^{-1}$ function, accurate calculation can hardly be executed when the sum is simply calculated for pairs of atoms, as is known. Therefore, a method called an Ewald method is generally used when calculation of the force or energy according to the Coulomb interaction is performed for the above-described infinite system (a system with the periodic boundary condition) (reference [1]).

This Ewald method can be applied to calculate the lattice sum (the sum for equivalent atoms belonging to different unit cells) of not only the Coulomb interaction but also an interaction given by an $r^{-n}$ function (multipole interaction or van der Waals force). This is an excellent method because, by appropriately speeding up convergence of calculation of the lattice sum in a real space and an imaginary space, the force or energy of the $r^{-n}$ long-range interaction is efficiently calculated.

However, MM/MD calculation for a periodic system using the conventional method or for an aperiodic system to which the supercell method is applied has the following problems.

Most of the MM/MD calculation execution time is spent for calculation of the force (and the energy). When the interatomic interaction is a long-range interaction, the number of pairs which must be taken into consideration becomes enormous. Particularly, for the Coulomb interaction, the calculation time still poses a serious problem even when the Ewald method is applied.

For MD calculation, when a temperature fluctuation is to be suppressed within the allowance in terms of statistical mechanics, the MD calculation must be performed for a system in which a number N of atoms per unit cell is at least several hundred. For this reason, it is an important challenge to minimize the amount of calculation of the force.

Especially, for the purpose of designing a substance/material, the MD calculation must be repeatedly performed for a number of systems while changing the simulation conditions including the temperature. Therefore, shortening of the calculation time, i.e., efficient calculation of the force is an important key to the practical new materials design.

In addition, since one step of the repetitive calculation in MD calculation corresponds to a time of 1 picosecond or less (about 0.01 PS) in a real system, the repetitive calculation must be performed in several ten thousand to several hundred thousand or more steps to analyze a change over time in system within a physically significant range. For this reason, for example, several ten days are still necessary to perform MD calculation once regardless of the improvement of the computer capability.

The above problems of the calculation time are posed when the long-range interaction is taken into consideration for both the periodic system and the aperiodic system handled by the supercell method. MM/MD calculation for the aperiodic system also has the following problems.

When the aperiodic system is to be handled by the supercell method, calculation must be performed using a unit cell with a sufficiently large size such that interaction between disorders contained in different unit cells can be neglected, as described above.

However, when the interatomic interaction is a long-range interaction, it is practically difficult to execute calculation using a sufficiently large unit cell because of the balance between the calculation time and the accuracy, resulting in a calculation error depending on the cell size. More specifically, in a normal simulation, calculation is often executed using a unit cell with a relatively small size in order to shorten the calculation time. In this case, the interaction with disorders contained in the peripheral unit cells cannot be neglected depending on the unit cell size, and a calculation error corresponding to the unit cell size is generated. In other words, the situation of the "aperiodic system" defined above cannot be exactly handled.

To confirm the dependency on the unit cell size, MM/MD calculation must be performed while changing the unit cell size, and the results must be compared. The Coulomb interaction as the most representative interaction is described by an $r^{-1}$ function. For this reason, to confirm convergence of the energy at, e.g., a 10-times higher accuracy, MM/MD calculation must be performed using a unit cell whose number N of atoms is $10^3$ times larger.

However, since the calculation time increases in proportion to the square of N, as described above, even confirmation of the dependency on the unit cell size can hardly be performed for the Coulomb interaction.

When the Coulomb interaction (charges) is considered in the aperiodic system, the following problem is generated in the supercell method. When the sum of charges of local disorders is not 0, the sum of charges per unit cell also deviates from 0 due to introduction of such disorders (e.g., an ion, a substitutional/interstitial impurity atom, and a defect). In the supercell method for which the periodic boundary condition is assumed, the sum of charges per unit cell must absolutely be 0 to prevent divergence of the energy, i.e., a restriction is technically required for the convenience of numerical calculation.

As a result of this restriction, when a system containing a disorder which breaks the charge neutrality is to be handled by the supercell method, and the sum of charges per unit cell is not 0, artificial charges (e.g., uniform charges) must be added to each constituent atom to nullify the sum. This disables calculation using the real charge distribution in the system. Particularly, consideration of the artificial charges largely affects the potential energy value.

The problems of the conventional method of analyzing the periodic system or aperiodic system using the supercell method will be summarized below.

(1) In MM/MD calculation, most of the MM/MD calculation execution time is spent for calculation of the force (and the energy). When the interatomic interaction is a long-range interaction, the number of pairs which must be taken into consideration becomes enormous. Particularly, for the Coulomb interaction, the calculation time still poses a serious problem even when the Ewald method is applied.

(2) When calculation for the aperiodic system is to be performed on the basis of the supercell method, calculation must be performed using a unit cell with a sufficiently large size such that interaction between disorders contained in different unit cells can be neglected.

However, when the interatomic interaction is a long-range interaction, it is practically difficult to execute calculation using a sufficiently large unit cell because of the calculation time, resulting in a calculation error depending on the cell size.

To confirm the dependency on the unit cell size, MM/MD calculation must be performed while changing the unit cell size, and the results must be compared. For a pair potential, the calculation time increases in proportion to the square of the number N of atoms. Therefore, for the $r^{-n}$ long-range interaction, even confirmation of the dependency on the unit cell size can hardly be performed.

(3) When analysis using the supercell method is to be performed for a system where the charge neutrality has been lost, the charge distribution must be corrected to nullify the total charges per unit cell. In this case, the total potential energy, the equilibrium lattice constant, the equilibrium atomic coordinates, and the like of the system undesirable change, so the charge distribution of the system where the charge neutrality has been lost cannot be strictly handled.

BRIEF SUMMARY OF THE INVENTION

The present invention has been made in consideration of the above situation, and has as its object to provide a materials design system capable of efficiently analyzing the stable structure or dynamic behavior of an infinite system regardless of whether the system is a periodic system or an aperiodic system.

(1) First Aspect of Present Invention

Arrangement

According to the first aspect of the present invention, there is provided a materials design system which analyzes a structural stability or dynamic behavior of a system (aperiodic system $S^2$) having a local disorder at an atomic or molecular level, thereby assisting materials design, comprising: a reference system $S^0$ processing unit for processing physical quantities of a system (reference system $S^0$) having no disorder; an aperiodic system $S^2$ processing unit for processing physical quantities of the aperiodic system $S^2$ and a list for making constituent atoms of the reference system $S^0$ to correspond with those of the aperiodic system $S^2$ in one-to-one correspondence to describe a structure of the aperiodic system $S^2$ on the basis of a deviation from the reference system $S^0$; a reference system $S^0$ calculation unit for calculating an energy of the reference system $S^0$ and a force acting on each atom or each molecule of the reference system $S^0$; an aperiodic system $S^2$ calculation unit for calculating an energy of the aperiodic system $S^2$ and a force acting on each constituent atom of the aperiodic system $S^2$ using the energy of the reference system $S^0$ and the force acting on each constituent atom of the reference system $S^0$, which are calculated by the reference system $S^0$ calculation unit; and an aperiodic system $S^2$ MM/MD calculation unit for executing calculation (MM calculation or MD calculation) of the structural stability or dynamic behavior of the aperiodic system $S^2$ using a calculation result from the aperiodic system $S^2$ calculation unit.

Function

With the above arrangement, a high-speed MM/MD calculation for the aperiodic system $S^2$ can be realized in the following manner.

In the first aspect, when MM/MD calculation for the aperiodic system $S^2$ is to be executed, the reference system $S^0$ (a system whose constituent atoms correspond to those of the aperiodic system $S^2$ in one-to-one correspondence) is simultaneously handled.

The reference system $S^0$ may be either a system having lattice vibration caused by the temperature effect at a finite temperature or a system without lattice vibration caused by the temperature effect at the absolute zero. In the former case, the reference system $S^0$ may be divided into a reference system $S^0$ (a system which does not consider lattice vibration) and a periodic system $S^1$ (a system which considers lattice vibration) and handled, as in the invention described in claims 2 and 5.

In the first aspect, the reference system $S^0$ processing unit processes the structure and potential parameters of the reference system $S^0$, and then, the aperiodic system $S^2$ processing unit processes the structure and potential parameters of the aperiodic system $S^2$ and makes the constituent atoms of the reference system $S^0$ to correspond to those of the aperiodic system $S^2$ in one-to-one correspondence.

The reference system $S^0$ calculation unit calculates the force and energy of the reference system $S^0$. Since the reference system $S^0$ has a periodicity, equation (18) (to be described later) can be applied to calculate the force acting on each constituent atom. In addition, the efficiency of calculation of the lattice sum of an $r^{-n}$ long-range interaction can be increased by the Ewald method.

When the reference system $S^0$ does not consider lattice vibration caused by the temperature effect, the amount of calculation of the force can be small because the number $N_{T=0}$ of atoms per unit cell $V^0$ is relatively small.

Since MM calculation performs an analysis at the absolute zero (T=0 K), the amount of calculation of the force of the reference system $S^0$ is small.

That is, according to the first aspect, the force acting on each constituent atom of the reference system $S^0$ whose calculation amount is small is used to calculate the force acting on each constituent atom of the aperiodic system $S^2$, thereby increasing the calculation efficiency.

More specifically, in the present invention, the structure of the aperiodic system $S^2$ is described as a deviation from the reference system $S^0$. With this method, MM/MD calculation for an infinite system containing a completely isolated disorder is realized without using any artificial periodic boundary condition, unlike the conventional method (supercell method).

For this purpose, the present invention has the aperiodic system $S^2$ processing unit. The aperiodic system $S^2$ processing unit sets the region (described as $R_{relax}$ in the embodiments) where lattice relaxation caused by the locally arranged disorder is taken into consideration, and processed the coordinates and potential parameters of each atom in this region and the correspondence list for making the atoms to correspond to those of the reference system $S^0$ in one-to-one correspondence. When the force (energy) of the aperiodic system $S^2$ is to be calculated by the aperiodic system $S^2$ calculation unit, the calculation result of the force of the reference system $S^0$, which is calculated by the reference system $S^0$ calculation unit, us used to increase the calculation efficiency. MM/MD calculation is executed by the MM/MD calculation unit using the force which has been calculated in the above way. With this processing, MM/MD calculation for the aperiodic system $S^2$ is realized with a higher accuracy at a higher speed than the supercell method.

(2) Second Aspect of Present Invention

Arrangement

According to the second aspect of the present invention, the materials design system according to claim 1, further comprises, when an analysis (MD calculation) of the dynamic behavior of the aperiodic system $S^2$ is to be performed at a finite temperature (temperature T>0 K); means for describing the structure of the aperiodic system $S^2$ on the basis of a deviation from a system (periodic system $S^1$) which has no local disorder but considers vibration of atoms which is caused by a temperature effect, the means for describing the structure of the aperiodic system $S^2$ comprising a periodic system $S^1$ processing unit for processing a physical quantity of the periodic system $S^1$ and a list for making constituent atoms of a reference system $S^0$ (the system in which lattice vibration is not taken into account) to correspond to those of the periodic system $S^1$ in one-to-one correspondence to describe a structure of the periodic system $S^1$ on the basis of a deviation from the reference system $S^0$, a periodic system $S^1$ calculation unit for calculating an energy of the periodic system $S^1$ and a force acting on each constituent atom of the periodic system $S^1$ using the energy of the reference system $S^0$ and the force acting on each constituent atom of the reference system $S^0$, which are calculated by the reference system $S^0$ calculation unit, and a periodic system $S^1$ MD calculation unit for executing periodic system MD calculation to analyze the dynamic behavior of the aperiodic system $S^2$ as a deviation from the periodic system $S_1$; and the aperiodic system $S^2$ MM/MD calculation unit executes calculation (MD calculation) of the structural stability or dynamic behavior of the aperiodic system $S^2$ using a calculation result from the aperiodic system $S^2$ calculation unit and a calculation result from the aperiodic system $S^1$ MD calculation unit.

Function

This aspect of the present invention provides, when the analysis (MD calculation) of the dynamic behavior of the aperiodic system $S^2$ is to be performed at a finite temperature (temperature T>0 K), the means capable of realizing efficient MD calculation for the aperiodic system $S^2$ even when the unit cell of the reference system $S^0$ is relatively large because of lattice vibration caused by the temperature effect.

More specifically, in the invention according to claim 2, the reference system $S^0$ having a relatively large size because of lattice vibration caused by the temperature effect is called a period system Si, and the reference system $S^0$ is regarded as a system which does not consider lattice vibration caused by the temperature effect. The structure of the periodic system $S^1$ is calculated using the force acting on each constituent atom of the reference system $S^0$, thereby increasing the calculation efficiency. In addition, an accurate and high-speed MD calculation for the aperiodic system $S^2$ is realized.

The method of increasing the calculation efficiency by handling two system, i.e., the reference system $S^0$ and the periodic system $S^1$ will be described later in association with the fourth aspect of the present invention. Note that the calculation unit called an MD calculation unit in the invention according to claim 1 is divided into a periodic system MD calculation unit and an aperiodic system MD calculation unit in the invention according to claim 2.

The invention according to claim 2 means that, in MD calculation for the aperiodic system $S^2$, three systems, i.e., the reference system $S^0$, the periodic system $S^1$, and the aperiodic system $S^2$ are handled.

(3) Third Aspect of Present Invention

Arrangement

According to the third aspect of the present invention, in the materials design system according to claim 1, the aperiodic system $S^2$ processing unit comprises means for changing, during simulation, a region where lattice relaxation of the aperiodic system $S^2$ is taken into consideration.

Function

According to this arrangement, even when the range of lattice relaxation (structure deformation) is larger than the region which is set before the start of MM/MD calculation, the structural stability or dynamic behavior of the aperiodic system $S^2$ can be properly and efficiently calculated.

(4) Fourth Aspect of Preset Invention

Arrangement

According to the fourth aspect of the present invention, there is provided a materials design system which analyzes a dynamic behavior of atoms or molecules in a system (periodic system $S^1$) which has no local disorder but vibration of atoms which is caused by a temperature effect, thereby assisting materials design, comprising: a reference system $S^0$ processing unit for processing a physical quantity of a system (reference system $S^0$) which does not consider vibration of atoms which is caused by the temperature effect; a periodic system $S^1$ processing unit for processing a physical quantity of the periodic system $S^1$ and a list for making constituent atoms of the reference system $S^0$ to correspond with those of the periodic system $S^1$ in one-to-one correspondence to describe a structure of the periodic system $S^1$ on the basis of a deviation from the reference system $S^0$; a reference system $S^0$ calculation unit for calculating an energy of the reference system $S^0$ and a force acting on each atom or each molecule of the reference system $S^0$; a periodic system $S^1$ calculation unit for calculating an energy of the periodic system $S^1$ and a force acting on each constituent atom of the periodic system $S^1$ using the energy of the reference system $S^0$ and the force acting on each constituent atom of the reference system $S^0$, which are calculated by the reference system $S^0$ calculation unit; and a periodic system $S^1$ MD calculation unit for analyzing dynamic behavior of the periodic system using a calculation result from the reference system $S^0$ calculation unit.

Function

With the above arrangement, a high-speed MD calculation for the periodic system $S^1$ can be realized I the following manner.

According to the fourth aspect, when MD calculation for the periodic system $S^1$ is to be executed, the reference system $S^0$ (a system whose constituent atoms correspond to those of the periodic system $S^1$ in one-to-one correspondence) is simultaneously handled.

The reference system $S^0$ corresponds to the structure of the periodic system $S^1$ at the absolute zero (T=0 K), so that this system has no lattice vibration caused by he temperature effect. For this reason, for the number $N_{T=0}$ of atoms per unit cell $U^0$ of the reference system $S^0$ generally, $N_{T=0} << N_{T>0}$ holds, as compared to the number $N_{T>0}$ of atoms per unit cell $U^1$ of the periodic system $S^1$. In a system such as an amorphous structure which originally has a relatively large minimum unit cell size, a situation $N_{T=0}$ $N_{T>0}$ may be generated. For such a system, an accurate and high-speed MD calculation can be realized using the calculation method according to claim 1 in which the reference system $S^0$ is regarded as a system which considers lattice vibration caused by the temperature effect.

In this aspect, the reference system $S^0$ processing unit processes the structure and potential parameters of the reference system $S^0$, and the periodic system $S^1$ processing unit processes the structure and potential parameters of the periodic system $S^1$ and makes the constituent atoms of the reference system $S^0$ to correspond to those of the periodic system $S^1$ in one-to-one correspondence.

The reference system $S^0$ calculation unit calculates the force and energy of the reference system $S^0$. Since the reference system $S^0$ has a periodicity, equation (69) (to be described later) can be applied to calculate the force acting on each constituent atom. In addition, the efficiency of calculation of the lattice sum of an $r^{-n}$ long-range interaction can be increased by the Ewald method.

The amount of calculation of the force can be small because the number $N_{T=0}$ of atoms per unit cell $U^0$ is relatively small.

More specifically, when the force (and eneregy) of the periodic system $S^1$ is to be calculated by the periodic system $S^1$ calculation unit, the following processing is performed. When the force acting on a constituent atom (k0) (kth atom contained in a fundamental cell $\zeta=0$) of the periodic system $S^1$ is to be calculated, a region $R_{cut}$ centered on the atom (k0) is assumed. As an interaction with each atom (k'$\zeta$') in the region $R_{cut}$, a correct value in the periodic system $S^1$ is calculated. As an interaction with each atom (k'$\zeta$') outside the region $R_{cut}$, an interaction in a system which neglects lattice vibration caused by the temperature effect, i.e., the reference system $S^0$ is approximately used.

Since the interatomic interaction is most largely influenced by atoms at a close position, it is adequate to approximately handle only an interaction with atoms at a remote position.

The region $R_{cut}$ is set such that the number of atoms outside the region $R_{cut}$ larger than that inside the region $R_{cut}$. Since the calculation result of the reference system $S^0$ whose calculation amount is small is used to calculate interactions with the atoms outside the region $R_{cut}$, the efficiency of calculation of the force of the periodic system $S^1$ can be increased.

In the present invention, the force calculated by the periodic system $S^1$ calculation unit is used to execute MD calculation by the periodic system MD calculation unit, thereby realizing MD calculation for the periodic system $S^1$ at a higher speed than that of the conventional method.

(5) Fifth Aspect of Present Invention

Arrangement

According to the fifth aspect of the present invention, in the materials design system according to claim 1 or 5, the reference system $S^0$ processing unit comprises means for setting a dummy atom or a dummy molecule in the reference system $S^0$.

Function

According to this arrangement, even when lattice relaxation (structure deformation) occurs in an arbitrary size, the structural stability or dynamic behavior of the aperiodic system $S^2$ or the periodic system $S^1$ can be accurately calculated by setting the dummy atom or dummy molecule in the reference system $S^0$.

(6) Sixth Aspect of Present Invention

According to the sixth aspect of the present invention, there is provided a storage medium which stores a computer program for causing a computer system to analyze a structural stability or dynamic behavior of a crystal system (aperiodic system $S^2$) having a local disorder at an atomic or molecular level to assist materials design, comprising: a reference system $S^0$ processing procedure code of processing a physical quantity of a system (reference system $S^0$) having no disorder; an aperiodic system $S^2$ processing procedure code of processing a physical quantity of the aperiodic system $S^2$ and a list for making constituent atoms of the reference system $S^0$ to correspond with those of the aperiodic system $S^2$ in one-to-one correspondence to describe a structure of the aperiodic system $S^2$ on the basis of a deviation from the reference system $S^0$; a reference system $S^0$ calculation procedure code of calculating an energy of the reference system $S^0$ and a force acting on each atom or each molecule of the reference system $S^0$; an aperiodic system $S^2$ calculation procedure code of calculating an energy of the aperiodic system $S^2$ and a force acting on each constituent atom of the aperiodic system $S^2$ using the energy of the reference system $S^0$ and the force acting on each constituent atom of the reference system $S^0$, which are calculated by the reference system $S^0$ calculation procedure code; and an MM/MD calculation procedure code of executing calculation (MM calculation or MD calculation) of the structural stability or dynamic behavior of the aperiodic system $S^2$ using a calculation result from the aperiodic system $S^2$ calculation procedure code.

(7) Seventh Aspect of Present Invention

According to the seventh aspect of the present invention, the storage medium described according to sixth aspect further comprises, when an analysis (MD calculation) of the dynamic behavior of the aperiodic system $S^2$ is to be performed at a finite temperature (temperature T>0 K): a procedure code of describing the structure of the aperiodic system $S^2$ on the basis of a deviation from a system (periodic system $S^1$) which has no local disorder but considers vibration of atoms which is caused by a temperature effect, the procedure code of describing the structure of the aperiodic system $S^2$ comprising, a periodic system $S^1$ processing procedure code of processing a physical quantity of the periodic system $S^1$ and a list for making constituent atoms of a reference system $S^0$ (the system in which lattice vibration is not taken into account) to correspond to those of the periodic system $S^1$ in one-to-one correspondence to describe a structure of the periodic system $S^1$ on the basis of a deviation from the reference system $S^0$, a periodic system $S^1$ calculation procedure code of calculating an energy of the periodic system $S^1$ and a force acting on each constituent atom of the periodic system $S^1$ using the energy of the reference system $S^0$ and the force acting on each constituent atom of the reference system $S^0$, which are calculated by the reference system $S^0$ calculation procedure code, and a periodic system MD calculation procedure code of executing periodic system MD calculation to analyze the dynamic behavior of the aperiodic system $S^2$ as a deviation from the periodic system $S^1$; and the aperiodic system $S^2$ MM/MD calculation procedure code executes calculation (MD calculation) of the structural stability or dynamic behavior of the aperiodic system $S^2$ using a calculation result from the aperiodic system $S^2$ calculation procedure code and a calculation result from the aperiodic system $S^1$ MD calculation procedure code.

The function of the seventh aspect corresponds to that of the second aspect of the present invention.

(8) Eight Aspect of Present Invention

According to the eighth aspect of the present invention, in the storage medium according to the sixth aspect, the aperiodic system $S^2$ processing procedure code comprises a procedure code of changing, during simulation, a region where lattice relaxation of the aperiodic system $S^2$ is taken into consideration.

The function of the eighth aspect corresponds to that of the third aspect of the present invention.

(9) Ninth Aspect of Present Invention

According to the ninth aspect of the present invention, there is provided a storage medium which stores a computer program for causing a computer system to analyze a dynamic behavior of atoms or molecules in a system (periodic system $S^1$) which has no local disorder but vibration of atoms which is caused by a temperature effect, thereby assisting materials design, comprising: a reference system $S^0$ processing procedure code of processing a physical quantity of a system (reference system $S^0$) which does not consider vibration of atoms which is caused by the temperature effect; a periodic system $S^1$ processing procedure code of processing a physical quantity of the periodic system $S^1$ and a list for making constituent atoms of the reference system $S^0$ to correspond with those of the periodic system $S^1$ in one-to-one correspondence to describe a structure of the periodic system $S^1$ on the basis of a deviation from the reference system $S^0$; a reference system $S^0$ calculation procedure code of calculating an energy of the reference system $S^0$ and a force acting on each atom or each molecule of the reference system $S^0$; and a periodic system calculation procedure code of calculating an energy of the periodic system $S^1$ and a force acting on each constituent atom of the periodic system $S^1$ using the energy of the reference system $S^0$ and the force acting on each constituent atom of the reference system $S^0$, which are calculated by the reference system $S^0$ calculation procedure code; and a periodic system $S^1$ MD calculation procedure code for analyzing dynamic behavior of the periodic system using a calculation result from the reference system $S^0$ calculation procedure code.

The function of the ninth aspect corresponds to that of the fourth aspect of the present invention.

(10) 10th Aspect of Present Invention

According to the 10th aspect of the present invention, in a storage medium according to the sixth or ninth aspect, the reference system $S^0$ processing procedure code comprises a procedure code of setting a dummy atom or a dummy molecule in the reference system $S^0$.

The function of the 10th aspect corresponds to that of the fifth aspect of the present invention.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a table showing an example of a correspondence list corresponding to the reference system $S^0$ and the aperiodic system $S^2$ in FIG. 3;

FIG. 5 is a table showing potential parameters A of substitutional and interstitial impurity atoms and defects in the reference system $S^0$ and the aperiodic system $S^2$;

FIG. 18 is a table showing a correspondence list [$S^0 \leftrightarrow S^1$] and a correspondence list [$S^1 \leftrightarrow S^2$];

FIG. 19 is a correspondence table showing a comparison, between a periodic system $S^1$ and the aperiodic system $S^2$, of the potential parameters A and the masses m of substitutional and interstitial impurity atoms and defects handled in the MD calculation for an aperiodic system $S^2$ according to the sixth embodiment;

DETAILED DESCRIPTION OF THE INVENTION

The first to seventh embodiments of the present invention will be described below with reference to the accompanying drawing.

First Embodiment

MM/MD Calculation for Aperiodic System $S^2$

The first embodiment of the present invention will be described first with reference to the accompanying drawing.

This embodiment corresponds to the invention described in claim 1. In this embodiment, a case wherein a "disorder" is an "impurity" will be described. In this case, the aperiodic system $S^2$ is also called an "isolated impurity system".

Figure 1:
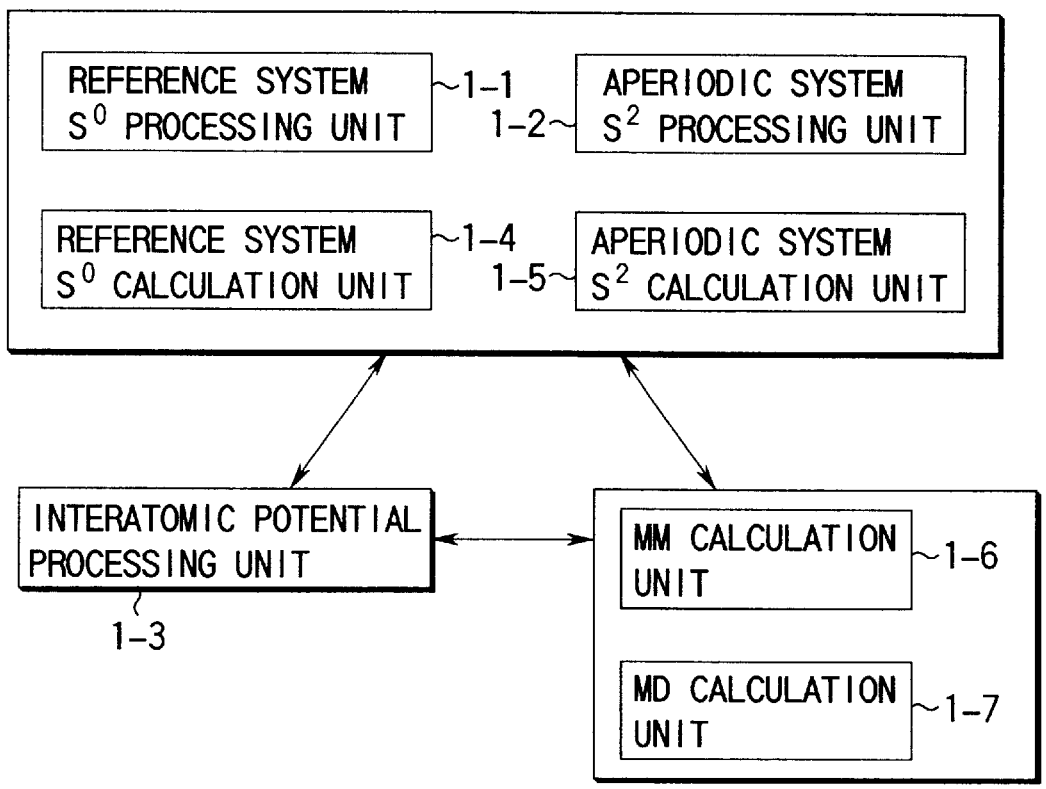
FIG. 1 is a block diagram showing the arrangement of a materials design system according to the first embodiment.

FIG. 1 is a block diagram showing the arrangement of a materials design system according to the first embodiment of the present invention. This system arrangement is basically common to the second, third, and fourth embodiments to be described later.

The materials design system of this embodiment comprises a reference system $S^0$ processing unit 1-1, an aperiodic system $S^2$ processing unit 1-2, an interatomic potential processing unit 1-3, a reference system $S^0$ calculation unit 1-4, an aperiodic system $S^2$ calculation unit 1-5, an MM calculation unit 1-6, and an MD calculation unit 1-7. In this embodiment, the processing operations of the respective blocks shown in FIG. 1 will be described first, and then, the flow of processing of the materials design system will be described using flow charts.

Figure 2:
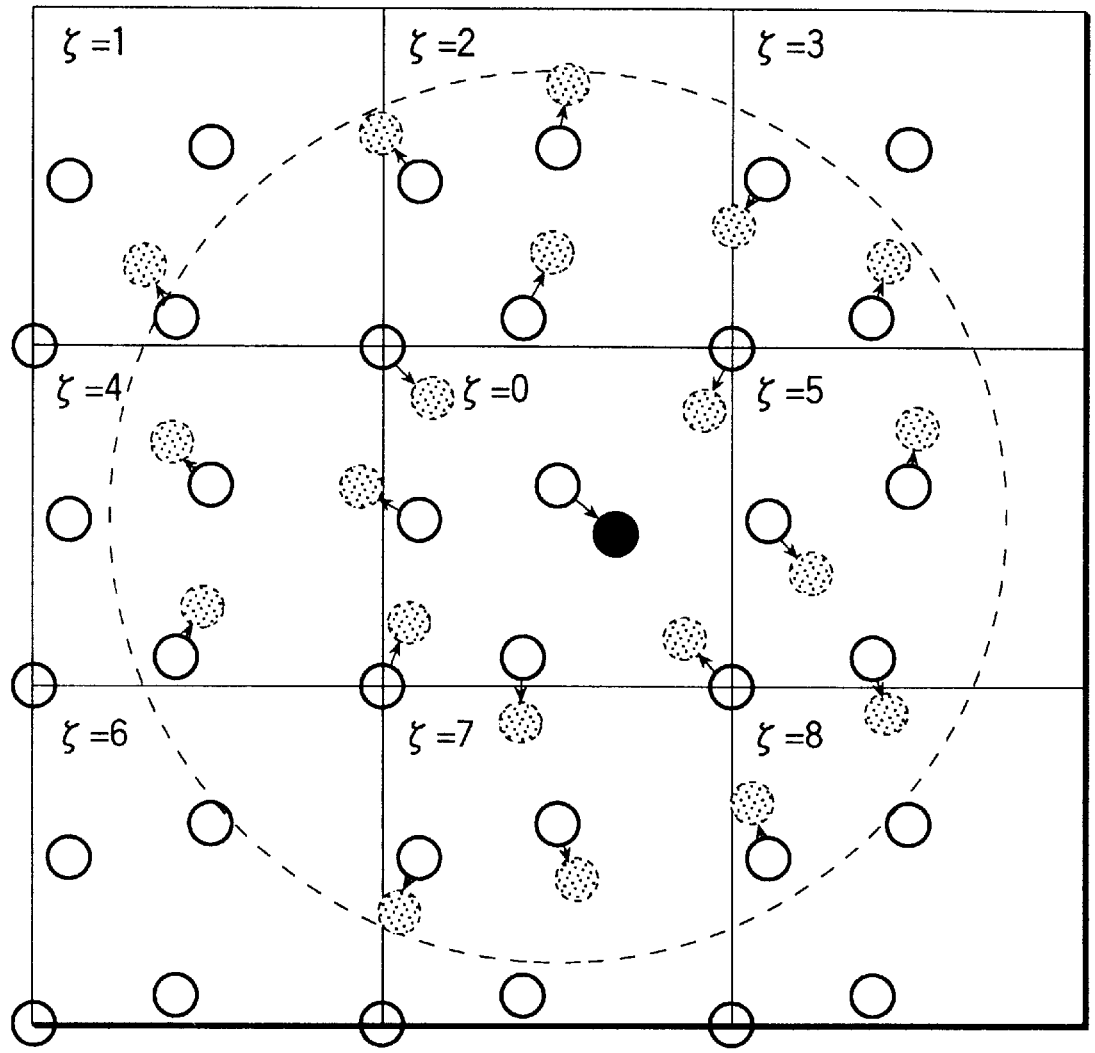
FIG. 2 is a view for explaining the relationship between a reference system $S^0$ and an aperiodic system $S^2$.

The primary characteristic feature of the calculation method of this embodiment is that the atomic coordinates of a system (aperiodic system $S^2$) containing an isolated impurity as a calculation target are represented by a deviation from a system (reference system $S^0$) in which no impurity is arranged at all. This will be described with reference to FIG. 2. Referring to FIG. 2, atoms indicated by solid lines are atoms constituting the reference system $S^0$, and boxes indicated by solid lines represent the unit cells of the reference system $S^0$.

FIG. 2 two-dimensionally shows nine unit cells. The central unit cell will be called a fundamental cell ($\zeta=0$). Assume that an atom placed almost at the center of the fundamental cell ($\zeta=0$) is replaced with another element (indicated by a bullet). This is a substitutional impurity atom. Lattice relaxation (structure deformation) occurs at its periphery because of the presence of such an impurity. This lattice relaxation normally occurs only in a finite region centered on the impurity, and this region is indicated by a dashed line in FIG. 2. Since the equilibrium atomic coordinates of the atoms in this region change due to the interaction from the impurity, for example, the atoms are arranged at positions indicated by dashed lines (gray bullets). Therefore, the aperiodic system $S^2$ in this embodiment corresponds to the reference system $S^0$ in which atomic coordinates in the region have changed.

Such a structure can be very effectively represented by a deviation between the crystal structure of the reference system $S^0$ and that of the aperiodic system $S^2$ (the deviation is indicated by arrows in FIG. 2, and this deviation will also be referred to as a relaxation amount hereinafter). The reason for this is as follows. Since the reference system $S^0$ contains no impurity at all, the unit cell can be set to be relatively small. Accordingly, the data amount (coordinates of atoms contained in the unit cell, potential parameters, and so on) required to describe the crystal structure of the reference system $S^0$ can be small. In addition, the amount of calculation of the potential energy or force can also be decreased.

Next, the deviation from the reference system $S^0$ will be described. Since this deviation is present only in a finite region centered on the impurity in the aperiodic system $S^2$, the data amount (vectors representing the deviations of the respective atoms) is not so large. Since the potential energy or force in the aperiodic system $S^2$ is calculated on the basis of this deviation, the amount of this calculation is not so large.

In the conventional supercell method, calculation must be executed using a unit cell nine or more times (27 times as a three-dimensional size) larger than that of the reference system $S^0$ to calculate lattice relaxation as shown in FIG. 2. This results in disadvantages as described in the above-mentioned (BACKGROUND OF THE INVENTION).

In this embodiment, the two systems associated with each other, i.e., the reference system $S^0$ and the aperiodic system $S^2$ are handled. The physical quantities (the atomic coordinates, the potential parameters, the potential energies of the systems, forces acting on the respective atoms, and the like) of the two systems must be clearly discriminated. The physical quantities of the reference system $S^0$ will be represented with a suffix "0", and those of the aperiodic system $S^2$ will be represented with a suffix "2" hereinafter, thereby discriminating the physical quantities.

Processing of the reference system $S^0$ processing unit 1-1 shown in FIG. 1 will be describe first. As described above, since the reference system $S^0$ contains no impurity at all, the unit cell size can be relatively small. When a perfect crystal is assumed as the reference system $S^0$, the minimum unit cell of the crystal can be regarded as the unit cell of the reference system $S^0$. Not only the perfect crystal but also an amorphous structure may be assumed as the reference system $S^0$ as far as the amorphous structure has a periodicity.

The reference system $S^0$ processing unit 1-1 receives the lattice constants of the reference system $S^0$, the number $N^0$ of atoms per unit cell, atomic coordinates $r^0(h0)_\alpha$ of $N^0$ atoms, and potential parameters $A^0(h0)$ of $N^0$ atoms, and holds these values.

All the unit cells are equivalent under the periodic boundary condition. Attention is paid to a unit cell $\zeta=0$, and the atomic coordinates and potential parameters are designated for this fundamental cell ($\zeta=0$). The coordinate value $r^0(h0)_\alpha$ represents the $\alpha$-direction coordinate of the hth atom contained in the fundamental cell ($\zeta=0$). Coordinate value $r^0(h\zeta)_\alpha$ of an atom contained in an arbitrary unit cell is calculated on the basis of the lattice constants (fundamental translation vector $\epsilon a_{\lambda\alpha}$) and the relative coordinates ($x_\lambda(h)$) by equations (1) to (3) below:

$$r^0(h\zeta)_\alpha = r^0(\zeta)_\alpha + r^0(h)_\alpha \qquad (1)$$

$$r^0(\zeta)_\alpha = \zeta_1 a_{1\alpha} + \zeta_2 a_{2\alpha} + \zeta_3 a_{3\alpha} \qquad (2)$$

$$r^0(h)_\alpha = x_1(h)a_{1\alpha} + x_2(h)a_{2\alpha} + x_3(h)a_{3\alpha} \qquad (3)$$

where $\lambda$ is the suffix for discriminating the three fundamental translation vectors. The reference system $S^0$ processing unit 1-1 may receive the relative coordinates $x_\lambda(h)$ in place of the atomic coordinates $r^0(h0)_\alpha$ and set $r^0(h0)_\alpha$ in accordance with the above equations.

The potential parameter $A^0(h0)$ is an interatomic potential parameter held by the interatomic potential processing unit 1-3. In the case of Coulomb interaction, $A^0(h0)$ corresponds to a point change. For the atomic coordinates $r^0(h0)_\alpha$ and the potential parameters $A^0(h0)$, equations (4) and (5) below hold for an arbitrary cell $\zeta$ because of the periodic boundary condition:

$$r^0(h\zeta)_\alpha = r^0(h0)_\alpha + r^0(\zeta)_\alpha \qquad (4)$$

$$A^0(h\zeta) = A^0(h0) \qquad (5)$$

Handling for describing the crystal structure of the reference system $S^0$ is the same as that of the conventional supercell method. Handling of the potential parameters $A^0(h0)$ is also associated with the processing operation of the interatomic potential processing unit 1-3 shown in FIG. 1 and will be described in detail in association with the interatomic potential processing unit 1-3.

Processing of the aperiodic system $S^2$ processing unit 1-2 shown in FIG. 1 will be described next. In this embodiment, some atoms of the above-described reference system $S^0$ are replaced with impurity atoms. Accordingly, the atoms of the reference system $S^0$ and those of the aperiodic system $S^2$ must be handled in one-to-one correspondence. In the aperiodic system $S^2$, the periodicity of the reference system $S^0$ disappears because of the existence of the local impurity (FIG. 2). For this reason, the notation using the atomic numbers (h$\zeta$) representing the periodicity is not appropriate anymore, and serial numbers (i) must be set for the atoms of the aperiodic system $S^2$.

Figure 3:
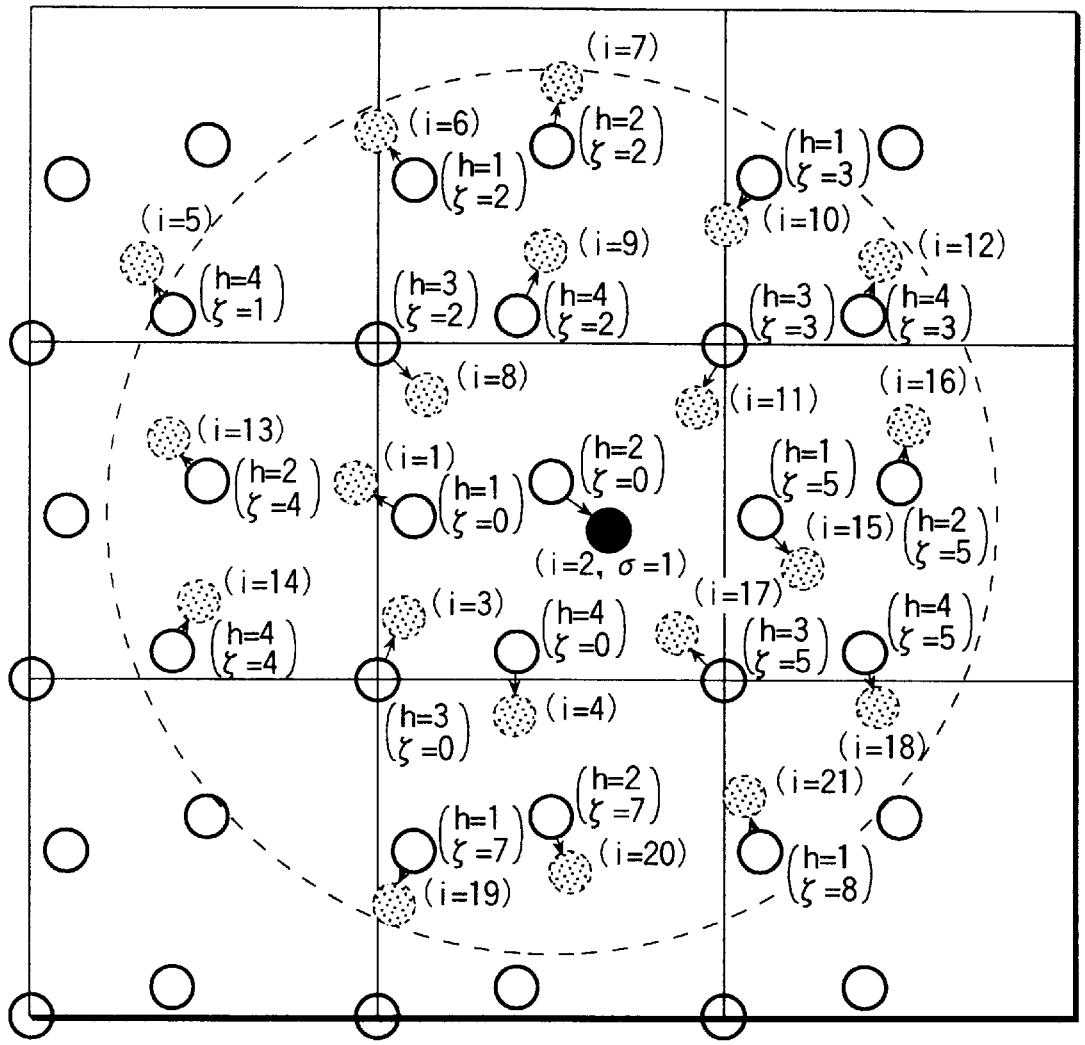
FIG. 3 is a view showing the constituent atoms of the reference system $S^0$ and the aperiodic system $S^2$ shown in FIG. 2 while assigning atomic numbers (h$\zeta$) and serial numbers (i) to the atoms.

The above processing can be performed using the correspondence list $[S^0 \leftrightarrow S^2]$. An example of this correspondence list $[S^0 \leftrightarrow S^2]$ is shown in FIG. 4. This table shows the correspondence list $[S^0 \leftrightarrow S^2]$ for the system shown in FIG. 2. In FIG. 3, atomic numbers are assigned to the constituent atoms of the reference system $S^0$ and the aperiodic system $S^2$ in FIG. 2. The atomic numbers in FIG. 3 correspond to those shown in the correspondence list $[S^0 \leftrightarrow S^2]$ (FIG. 4). FIG. 3 will be referred hereinafter.

In the correspondence list $[S^0 \leftrightarrow S^2]$ shown in FIG. 4, the atomic numbers (h$\zeta$) of the reference system $S^0$ which contains four ($N^0=4$) constituent atoms in the unit cell are registered. As the constituent atoms of the aperiodic system $S^2$ corresponding to the reference system $S^0$, 21 serial numbers (i) are registered. The 21 atoms correspond to atoms contained in a region indicated by a dashed line in FIG. 3. As is apparent from the correspondence list $[S^0 \leftrightarrow S^2]$ in FIG. 4, the constituent atoms of the aperiodic system $S^2$ are made to correspond to those of the reference system $S^0$ in one-to-one correspondence. This correspondence can also be uniquely made in accordance with for example an equation $i = h + \zeta N^0$. For the descriptive convenience, the impurity atoms in the aperiodic system $S^2$ will be also represented by impurity numbers ($\sigma$).

The flow of the processing operation of the aperiodic system $S^2$ processing unit 1-2 will be described below mainly in association with the initial setting stage of MM/MD calculations. The aperiodic system $S^2$ processing unit 1-2 receives the number $N^{imp}$ of impurity atoms contained in the aperiodic system $S^2$, numbers which indicate the $N^{imp}$ impurity atoms, potential parameters $A^{imp}(\sigma)$ of the $N^{imp}$ impurity atoms, and a region $R_{relax}$ where lattice relaxation is taken into consideration. The numbers which indicate the $N^{imp}$ impurity atoms mean the numbers of atoms in the reference system $S^0$, which are replaced with impurity atoms. More specifically, a set $\{(h_1,\zeta_1), (h_2,\zeta_2), \ldots (h_{Nimp}, \zeta_{Nimp})\}$ is designated.

The example shown in FIG. 3 contains only one impurity atom ($N^{imp}=1$), and a set $\{(h=20, \zeta=0)\}$ is designated. An arbitrary number of impurity atoms can be handled as $N^{imp}$. The impurity atom to be designated can be contained in the fundamental cell ($\zeta=0$) of the reference system $S^0$ or an image cell ($\zeta \neq 0$). The set $\{(h_1,\zeta_1), (h_2,\zeta_2), \ldots, (h_{Nimp}, \zeta_{Nimp})\}$ for designating the impurity atoms is made to correspond to a set of impurity numbers, i.e., $\{(\sigma_1), (\sigma_2), \ldots, (\sigma_{Nimp})\}$. In the correspondence list $[S^0 \leftrightarrow S^2]$ shown in FIG. 4, the number of impurity atoms is 1, and an impurity number ($\sigma=1$) is assigned to the atom ($i=2$) of the aperiodic system $S^2$.

The region $R_{relax}$ where lattice relaxation is taken into consideration will be described next. In the aperiodic system $S^2$, lattice relaxation occurs around the impurity. Since the lattice relaxation becomes almost zero at a position far from the impurity atom, the lattice relaxation can be calculated only in a finite region centered on the impurity atoms. As the region where the lattice relaxation is taken into consideration, for example, a sphere having the radius $R_{relax}$ and centered on the center of gravity of the impurity atoms can be assumed. This region need not always be spherical. In this embodiment, the region where lattice relaxation is taken into consideration is generally represented by $R_{relax}$. This region $R_{relax}$ may be arbitrarily designated by the user or set on the side of the materials design system of this embodiment. The aperiodic system $S^2$ processing unit 1-2 counts the number $N^2$ of atoms contained in the region $R_{relax}$ ($N^2$ does not means the square of N. In the present invention, the square of N is described as N×N). All the $N^{imp}$ impurity atoms should be contained in the $N^2$ atoms, as a matter of course. In the example shown in FIG. 3, $N^2=21$. The aperiodic system $S^2$ processing unit 1-2 calculates coordinates $r^2(i)_\alpha$ of the $N^2$ atoms and holds the coordinate values. The coordinates $r^2(i)_\alpha$ are calculated by equation (6) below:

$$r^2(i)_\alpha = r^0(i)_\alpha + \Delta r(i)_\alpha \tag{6}$$

As described above, the atoms (i) of the aperiodic system $S^2$ are made to correspond to the atoms (h$\zeta$) of the reference system $S^0$ in one-to-one correspondence on the basis of the correspondence list $[S^0 \leftrightarrow S^2]$. Therefore, for $r^0(i)_\alpha$ of equation (6), equation (7) below holds on the basis of the correspondence list $[S^0 \leftrightarrow S^2]$ and the periodicity of the reference system $S^0$:

$$r^0(i)_\alpha = r^0(h\zeta)_\alpha = r^0(h0)_\alpha + r^0(\zeta)_\alpha \tag{7}$$

The value is easily calculated from $r^0(h0)_\alpha$ which has already been held by the reference system $S^0$ processing unit 1-1.

Next, the second term of equation (6), i.e., $\Delta r(i)_\alpha$ will be described. As described above, in this embodiment, the crystal structure of the aperiodic system $S^2$ is described on the basis of the deviation from the reference system $S^0$. The deviation corresponds to $\Delta r(i)_\alpha$ which physically represents lattice relaxation caused by impurity. When the stable structure of the aperiodic system $S^2$ is to be calculated by MM calculation on the basis of the calculation method of this embodiment, this relaxation amount $\Delta r(i)_\alpha$ is calculated. The initial values of $\Delta r(i)_\alpha$ are set at the initial setting stage of MM/MD calculation. These initial values may be arbitrarily designated by the user or automatically set at 0 by the materials design system of this embodiment.

Handling of the potential parameter of each atom of the aperiodic system $S^2$ will be described next. As described above, the aperiodic system $S^2$ processing unit 1-2 receives the potential parameters $A^{imp}(\sigma)$ of the $N^{imp}$ impurity atoms ($\sigma$). Accordingly, the aperiodic system $S^2$ processing unit 1-2 sets potential parameters $A^2(i)$ of the $N^2$ atoms (i) contained in the region $R_{relax}$ by using equations (8) and (9):

$$A^2(i)=A^0(i)(=A^0(h\zeta)=A^0(h0) \ldots i \neq \sigma \tag{8}$$

$$A^2(i)=A^{imp}(\sigma) \ldots i=\sigma \tag{9}$$

Like the potential parameters $A^0(h0)$ of the reference system $S^0$, handling of the potential parameters $A^2(i)$ is associated with the processing operation of the interatomic potential processing unit 1-3. The interatomic potential processing unit 1-3 will be described below.

The interatomic potential processing unit 1-3 shown in FIG. 1 holds a function representing an interatomic interaction. In this embodiment, the interatomic interaction acting between the atom (i) and an atom (j) is described by equation (10):

$$\phi(i,j)=A(i)A(j)\phi(r|i,j) \tag{10}$$

where $A(i)$ corresponds to the potential parameters $A^0(h0)$ and $A^2(i)$ described about the reference system $S^0$ processing unit 1-1 and the aperiodic system $S^2$ processing unit 1-2. When $\phi(ij)$ represents a Coulomb interaction, $A(i)=q_i$, and $\phi(r|ij)=1/\{r(ij)\}$, where $q_i$ is the point charge of the atom (i) and $r(ij)$ is the distance between the atoms (i) and (j).

As the interatomic interaction described by the function (10), there are interatomic interactions such as van der Waals force and multipole interaction described by $r^{-n}$ functions, in addition to the Coulomb interaction. Since these interactions are generally taken into consideration in MM/MD simulations, it can be said that equation (10) represents the general function of interatomic interactions. The materials design system of this embodiment can simultaneously handle a plurality of interatomic interactions such as Coulomb interaction+van der Waals force+short-range repulsive force. In this case, the interatomic interaction $\phi(ij)$ between the atom (i) and the atom (j) is described by equations (11) and (12):

$$\phi(i,j) = \sum_\mu \phi_\mu(i,j) \tag{11}$$

$$= \sum_\mu A_\mu(i)A_\mu(j)\phi_\mu(r|i,j) \tag{12}$$

Regardless of whether one or a plurality of interatomic interactions are to be taken into consideration, handling is performed in the same manner. Therefore, a suffix $\mu$ will be omitted for the above-described reference system $S^0$ processing unit 1-1 and the aperiodic system $S^2$ processing unit 1-2 and in the following description. In this embodiment, a description associated only with an interatomic potential will be made. The calculation method of this embodiment can also handle a molecular crystal. In this case, an intermolecular potential is processed like the interatomic potential.

As described about the aperiodic system $S^2$ processing unit 1-2, the atoms of the reference system $S^0$ are made to correspond to those of the aperiodic system $S^2$ in one-to-one correspondence on the basis of the correspondence list $[S^0 \leftrightarrow S^2]$, and the potential parameters are related to each other by equations (8) and (9). According to equations (8) and (9), when the potential parameters of the reference system $S^0$ are compared to those of the aperiodic system $S^2$, the impurity atoms of the aperiodic system $S^2$ have potential parameter values different from those of the corresponding atoms of the reference system $S^0$. However, the other atoms of the aperiodic system $S^2$ have the same potential parameter values as those of the corresponding atoms of the reference system $S^0$.

The materials design system of this embodiment can handle three types of impurities, i.e., a substitutional impurity atom, an interstitial impurity atom, and a defect. These impurities are discriminated on the basis of the relationship in the potential parameters between the reference system $S^0$ and the aperiodic system $S^2$, as shown in FIG. 5. Of the three types of impurities shown in FIG. 5, the interstitial impurity atom must be particularly carefully handled. An atom corresponding to the interstitial impurity atom is not originally present in the reference system $S^0$. To make the one-to-one correspondence based on the correspondence list $[S^0 \leftrightarrow S^2]$, a dummy atom must be set in the reference system $S^0$ in advance. Since the potential parameter $A^0(h0)$ of the dummy atom is always 0, as shown in FIG. 5, the potential energy or the force acting on each atom of the reference system $S^0$ does not change even when the dummy atom is set.

In the materials design system of this embodiment, to obtain the stable structure or dynamic behavior of the aperiodic system $S^2$ by MM calculation or MD calculation, the potential energy and the force acting on each atom of the reference system $S^0$ and the aperiodic system $S^2$ are calculated. This method will be described below.

The processing operation of the reference system $S^0$ calculation unit 1-4 shown in FIG. 1 will be described first. Since the reference system $S^0$ has a periodicity, handling of the reference system $S^0$ is the same as that of the conventional supercell method. The reference system $S^0$ calculation unit 1-4 calculates the potential energy of the reference system $S^0$ and the force acting on each atom of the reference system $S^0$. In this embodiment, a position vector $r^0(h\zeta, h'\zeta')_\alpha$ between two atoms is defined by equation (13) below:

$$r^0(h\zeta, h'\zeta')_\alpha = r^0(h'\zeta')_\alpha - r^0(h\zeta)_\alpha \qquad (13)$$

The sign in the equations of the potential energy and force to be described below is based on the definition of equation (13). For the potential energy, equation (14) is calculated for the atom (h0) using the interatomic potential represented by equation (10):

$$e^0(h0) = \sum_{h'}^{N^0} \sum_{\zeta'}^{all} {}^* A^0(h'\zeta') \varphi(r^0 \mid h0, h'\zeta') \qquad (14)$$

For the force, $f^0(h0)_\alpha$ is calculated in accordance with equations (15) and (16):

$$f^0(h0)_\alpha = \sum_{h'}^{N^0} \sum_{\zeta'}^{all} {}^* A^0(h'\zeta') \varphi^{(1)}(r^0 \mid h0, h'\zeta')_\alpha \qquad (15)$$

$$\varphi^{(1)}(r^0 \mid h\zeta, h'\zeta')_\alpha = \left. \frac{\partial}{\partial r(h\zeta, h'\zeta')_\alpha} \varphi(r \mid h\zeta, h'\zeta') \right|_{r=r^0} \qquad (16)$$

In this embodiment, $e^0(h0)$ and $f^0(h0)$ are called a partial potential energy and a partial force, respectively.

The summation $$\sum_{\zeta'} {}^*$$

in equation (15) means that the term in which $h'=h$ and $\zeta'=\zeta$ is eliminated from the sum. The summation $$\sum^{all}$$

represents that the sum is calculated for terms as many as possible until the convergence of the sum attains a sufficient accuracy. Since the terms added by this sum correspond to the interatomic potential itself or the differential coefficient of the interatomic potential, the value of each term generally becomes smaller as the interatomic distance increases. Therefore, $$\sum^{all}$$

means that the terms are added while calculating interactions for sufficiently far atoms where the interatomic interactions become negligible.

In calculation of the Coulomb interaction, the efficiency of calculation can be increased using the Ewald method (reference 1) for equations (14) and (15). A potential energy $E^0_{cell}$ per unit cell of the reference system $S^0$ is obtained using equation (14), as follows:

$$E^0_{cell} = \frac{1}{2} \sum_h^{N^0} A^0(h0) e^0(h0) \qquad (17)$$

In the conventional supercell method, $E^0_{cell}$ or $E^0_{cell}/N^0$ (potential energy per atom) is calculated. A value obtained by adding $E^0_{cell}$ of all unit cells contained in the reference system $S^0$ corresponds to a total potential energy $E^0_{whole}$. An a component $F^0(h0)_\alpha$ of the force acting on each atom (h0) in the fundamental cell ($\zeta=0$) of the reference system $S^0$ is calculated using equation (15) as follows:

$$F^0(h0)_\alpha = A^0(h0) f^0(h0)_\alpha \qquad (18)$$

In the conventional supercell method, MM calculation and MD calculation are executed using the value $F^0(h0)_\alpha$.

The processing operation of the aperiodic system $S^2$ calculation unit 1-5 shown in FIG. 1 will be described next. The primary characteristic feature of this embodiment is that the relaxation amount $\Delta r(i)_\alpha$ from the reference system $S^0$ is calculated to obtain, e.g., the stable structure of the aperiodic system $S^2$. In this embodiment, to obtain the relaxation amount $\Delta r(i)_\alpha$, $\Delta E$ and $\Delta F(i)_\alpha$ of the aperiodic system $S^2$ are calculated. The two quantities are defined by equations (19) and (20):

$$\Delta E = E^2_{whole} - E^0_{whole} \qquad (19)$$

$$\Delta F(i)_\alpha = F^2(i)_\alpha - F^0(i)_\alpha \qquad (20)$$

These values are obtained by subtracting the physical quantities (second term on the right-hand side) of the reference system $S^0$ from the physical quantities (first term on the right-hand side) of the aperiodic system $S^2$. More specifically, $\Delta E$ represents the change in potential energy by lattice relaxation caused by the impurity doped in the reference system $S^0$. Both $E^0_{whole}$ and $E^2_{whole}$ are the total potential energies and therefore represent divergence quantities. On the other hand, the difference $\Delta E$ has a finite value. This corresponds to the fact that the lattice relaxation caused by the local impurity atoms occurs only within a finite range.

$F^0(i)_\alpha$ and $F^2(i)_\alpha$ are forces acting on the atoms of the reference system $S^0$ and the aperiodic system $S^2$, respectively. $\Delta E$ and $\Delta F(i)_\alpha$ are defined by the above equations and calculated as follows. $\Delta E$ and $\Delta F(i)_\alpha$ are represented using two terms as follows:

$$\Delta E = \Delta E^{(a)} + \Delta E^{(b)} \tag{21}$$

$$\Delta F(i)_\alpha = \Delta F^{(a)}(i)_\alpha + \Delta F^{(b)}(i)_\alpha \tag{22}$$

The energy is represented as follows:

$$\Delta E^{(a)} = \sum_{i=\sigma}^{N^{imp}} [A^2(i) - A^0(i)] e^0(i) + \sum_{i=\sigma}^{N^{imp}} [A^2(i) - A^0(i)] \sum_{j(>i)=\sigma}^{N^{imp}} [A^2(j) - A^0(j)] \varphi(r^0 \mid i, j) \tag{23}$$

$$\Delta E^{(b)} = \sum_{i \in R_{relax}}^{N_2} A^2(i) \sum_{j(>i)}^{all} A^2(j) \left[ \delta r(i,j) \varphi^{[1]}(r^0 \mid i, j) + \frac{1}{2} [\delta r(i,j)]^2 \varphi^{[2]}(r^0 \mid i, j) \right] + O[(\delta r)^3] \tag{24}$$

$$\delta r(i,j) = |\vec{r}^2(i,j)| - |\vec{r}^0(i,j)| \tag{25}$$

$$\varphi^{[1]}(r^0 \mid i, j) = \left. \frac{d}{d r(i,j)} \varphi(r \mid i, j) \right|_{r=r^0} \tag{26}$$

$$\varphi^{[2]}(r^0 \mid i, j) = \left. \frac{d^2}{d [r(i,j)]^2} \varphi(r \mid i, j) \right|_{r=r^0} \tag{27}$$

The force is represented as follows:

$$\Delta F^{(a)}(i)_\alpha = [A^2(i) - A^0(i)] f^0(i)_\alpha + A^2(i) \sum_{j=\sigma}^{N^{imp}} * [A^2(j) - A^0(j)] \varphi^{(1)}(r^0 \mid i, j)_\alpha \tag{28}$$

$$\Delta F^{(b)}(i)_\alpha = A^2(i) \sum_{j}^{all} * A^2(j) \left[ \sum_\beta \Delta r(i,j)_\beta \varphi^{(2)}(r^0 \mid i, j)_{\alpha\beta} + \frac{1}{2} \sum_{\beta,\gamma} \Delta r(i,j)_\beta \Delta r(i,j)_\gamma \varphi^{(3)}(r^0 \mid i, j)_{\alpha\beta\gamma} \right] + O[(\Delta r)^3] \tag{29}$$

$$\Delta r(i,j)_\alpha = r^2(i,j)_\alpha - r^0(i,j)_\alpha \tag{30}$$

$$= (r^2(j)_\alpha - r^2(i)_\alpha) - (r^0(j)_\alpha - r^0(i)_\alpha) \tag{31}$$

$$\varphi^{(1)}(r^0 \mid i, j)_\alpha = \left. \frac{\partial}{\partial r(i,j)_\alpha} \varphi(r \mid i, j) \right|_{r=r^0} \tag{32}$$

$$\varphi^{(2)}(r^0 \mid i, j)_{\alpha\beta} = \left. \frac{\partial^2}{\partial r(i,j)_\alpha \partial r(i,j)_\beta} \varphi(r \mid i, j) \right|_{r=r^0} \tag{33}$$

-continued $$\varphi^{(3)}(r^0 \mid i, j)_{\alpha\beta\gamma} = \left. \frac{\partial^3}{\partial r(i,j)_\alpha \partial r(i,j)_\beta \partial r(i,j)_\gamma} \varphi(r \mid i, j) \right|_{r=r^0} \tag{34}$$

For $e^0(i)$ and $f^0(i)_\alpha$ of equations (23) and (28), equations (35) and (36) hold on the basis of the correspondence list $[S^0 \leftrightarrow S^2]$ and the periodicity of the reference system $S^0$:

$$e^0(i) = e^0(h\zeta) = e^0(h0) \tag{35}$$

$$f^0(i)_\alpha = f^0(h\zeta)_\alpha = f^0(h0)_\alpha \tag{36}$$

These values represent physical quantities calculated by the reference system $S^0$ calculation unit 1-4 on the basis of equations (14) and (15). In the above equations, $$\sum_{i=\sigma}^{N^{imp}}$$

represents the sum for $N^{imp}$ impurity atoms ($\sigma$), and $$\sum_{i \in R_{relax}}^{N^2}$$

means the sum for the $N^2$ atoms contained in the region $R_{relax}$.

The above-described series of equations mathematically represent Taylor expansion. The physical quantities ($E^2$whole and $F^2(i)_\alpha$) of the aperiodic system $S^2$ are Taylor-expanded on the basis of the deviation ($\delta r(ij)$ or $\Delta r(ij)_\alpha$) from the reference system $S^0$. The first term in the equation (21) or (22) is given by subtracting the physical quantity ($E^0$whole or $F^0(i)_\alpha$) from the zero-order term in the Taylor expansion. The second term in equation (21) or (22) corresponds to the higher-order term in the Taylor expansion. In equations (24) and (29) which give this higher-order term, terms of second or lower order are presented, and $O[(\delta r)^3]$ and $O[(\Delta r)^3]$ represent terms of third or higher arbitrary order.

Instead of equations (24) and (29), in equations (106) and (108) to be described later, equations in which the quantities of a periodic system $S^1$ are replaced with those of the reference system $S^0$ may be used.

The processing operation of the MM calculation unit 1-6 shown in FIG. 1 will be described next. The MM calculation unit 1-6 calculates the stable structure of the aperiodic system $S^2$ by MM calculation on the basis of the calculation method of this embodiment. In the MM calculation, the potential energy of the system is minimized to obtain the stable structure. Several calculation methods are available as a means for realizing this calculation. In this embodiment, a method of steepest descent will be exemplified. According to the materials design system of this embodiment, when MM calculation is to be executed using repetitive calculation based on the method of steepest descent, in the nth step, a deviation $\epsilon \Delta r(i|n)_\alpha$ of the $N^2$ atoms contained in the region $R_{relax}$ of the aperiodic system $S^2$ is calculated according to equation (37):

$$\Delta r(i|n)_\alpha = \Delta r(i|n-1)_\alpha + \epsilon \Delta F(i|n-1)_\alpha \tag{37}$$

where $\Delta F(i)_\alpha$ is calculated according to equation (22) by the aperiodic system $S^2$ calculation unit 1-5. In addition, a constant $\epsilon$ may be arbitrarily designated by the user or set on the side of the materials design system of this embodiment to efficiently execute the MM calculation. When $\Delta r(i)_\alpha$ is calculated by the MM calculation unit 1-6 in accordance with the above equation, the aperiodic system $S^2$ processing unit 1-2 updates the value $\Delta r(i)_\alpha$, and simultaneously, calculates the atomic coordinates $r^2(i)_\alpha$ of the aperiodic system $S^2$. The above processing is performed using repetitive calculation until $\Delta F(i|n)_\alpha$ becomes almost zero under a certain determination condition. With this processing, the stable structure of the aperiodic system $S^2$ can be obtained.

According to the calculation method of this embodiment, the stable structure of the aperiodic system $S^2$ can be obtained by equation (37), and simultaneously, the normal MM calculation can be performed for the atomic coordinates $r^0(h0)_\alpha$ of the reference system $S^0$. However, to increase the calculation efficiency, the stable structure (equilibrium structure) of the reference system $S^0$ is preferably input in advance, or before MM calculation for the aperiodic system $S^2$ is started, MM calculation for the reference system $S^0$ is preferably independently performed to obtain the stable structure of the reference system $S^0$. During this MM calculation, the aperiodic system $S^2$ calculation unit 1-5 can calculate $\Delta E$ on the basis of equation (21) in an arbitrary step. The difference $\Delta E$ physically represents the change in potential energy which is caused by the lattice relaxation by the impurity doped in the reference system $S^0$, as described above. When $\Delta E$ is calculated in each step, and the resultant value is monitored, the process of minimizing the potential energy of the aperiodic system $S^2$ by the MM calculation can be tracked.

The processing operation of the MD calculation unit 1-7 shown in FIG. 1 will be described next. In the MD calculation, the velocity of each atom is also calculated. Therefore, when MD calculation is to be executed, the reference system $S^0$ processing unit 1-1 and the aperiodic system $S^2$ processing unit 1-2 additionally hold $v^0(h0)_\alpha$ and $v^2(i)_\alpha$, respectively, representing the velocity of each atom. Masses $m^0(h0)$ and $m^2(i)$ are also held. Accordingly, a supplementary explanation about the reference system $S^0$ processing unit 1-1 and the aperiodic system $S^2$ processing unit 1-2 will be made, and then, the processing operation of the MD calculation unit 1-7 will be described. For the values $v^0(h0)_\alpha$ and $m^0(h0)$ held by the reference system $S^0$ processing unit 1-1, equations (38) and (39) hold on the basis of the correspondence list $[S^0 \leftrightarrow S^2]$ and the periodicity of the reference system $S^0$:

$$v^0(i)_\alpha = v^0(h\zeta)(=v^0(h0)_\alpha \quad (38)$$

$$m^0(i) = m^0(h\zeta) = m^0(h0) \quad (39)$$

These values are designated by the user at the initial setting stage of MD calculation. Alternatively, these values may be set on the side of the materials design system of this embodiment in accordance with a certain reference. Handling of the mass of each atom is the same as that of the potential parameter and can also be treated as one of potential parameters. Next, the aperiodic system $S^2$ processing unit 1-2 performs, for $v^2(i)_\alpha$, the same processing as that for $r^2(i)_\alpha$. More specifically, a description based on equation (20) below, which is equal to equation (6), is made:

$$v^2(i)_\alpha = v^0(i)_\alpha + \Delta v(i)_\alpha \quad (40)$$

The initial value of $\Delta v(i)_\alpha$ is set. This initial value may be arbitrarily designated by the user, or set at 0 on the side of the materials design system of this embodiment at once. Since the mass $m^2(i)$ of each atom can be regarded as one of potential parameters, as described above, the same processing as for $A^2(i)$ is performed. More specifically, a mass $m_{imp}(\sigma)$ of the $N^{imp}$ impurity atom is input to the aperiodic system $S^2$ processing unit 1-2, and accordingly, the masses $m^2(i)$ of the $N^2$ atoms (i) are set in accordance with equations (8) and (9). The supplementary explanation about the reference system $S^0$ processing unit 1-1 and the aperiodic system $S^2$ processing unit 1-2 has been made above.

The processing operation of the MD calculation unit 1-7 will be described. In this embodiment, a Verlet method will be exemplified as the algorithm of MD calculation. For the reference system $S^0$, the position and velocity of each of $N^0$ atoms (h0) contained in the fundamental cell ($\zeta=0$) at a time t are calculated on the basis of equations (41) and (42):

$$r^0(h0|t)_\alpha = \quad (41)$$
$$r^0(h0|t-\Delta t)_\alpha + \Delta t v^0(h0|t-\Delta t)_\alpha + \frac{(\Delta t)^2}{2m^0(i)}F^0(h0|t-\Delta t)$$

$$v^0(h0|t)_\alpha = v^0(h0|t-\Delta t)_\alpha + \frac{\Delta t}{2m^0(i)}[F^0(h0|t-\Delta t)_\alpha + F^0(h0|t)_\alpha] \quad (42)$$

The reference system $S^0$ processing unit 1-1 updates these values. $F^0(h0)_\alpha$ is the $\alpha$-direction force of the atom (h0), which is calculated by the reference system $S^0$ calculation unit 1-4 in accordance with equation (18). A value $\Delta t$ represents the time interval in MD calculation. The value $\Delta t$ may be arbitrarily designated by the user, or set on the side of the materials design system of this embodiment. MD calculation for the reference system $S^0$ according to equations (41) and (42) is handled as in the conventional supercell method.

For the aperiodic system $S^2$, $\Delta r(i)_\alpha$ and $\Delta v(i)_\alpha$ of the $N^2$ atoms (i) contained in the region $R_{relax}$ at a time t are calculated in accordance with equations (43) and (44):

$$\Delta r(i|t)_\alpha = \Delta r(i|t-\Delta t)_\alpha + \Delta t \Delta v(i|t-\Delta t)_\alpha + \frac{(\Delta t)^2}{2}\Delta F'(i|t-\Delta t) \quad (43)$$

$$\Delta v(i|t)_\alpha = \Delta v(i|t-\Delta t)_\alpha + \frac{\Delta t}{2}[F'(i|t-\Delta t)_\alpha + \Delta F'(i|t)_\alpha] \quad (44)$$

Accordingly, the aperiodic system $S^2$ processing unit 1-2 updates these values, and simultaneously, calculates $r^2(i)_\alpha$ and $v^2(i)_\alpha$ in accordance with equation (6) or (40). A value $\Delta F'(i)_\alpha$ is calculated by the aperiodic system $S^2$ calculation unit 1-5 in accordance with equations (45) to (47) obtained by slightly changing equations (28) and (29):

$$\Delta F'(i)_\alpha = \Delta F^{(a)'}(i)_\alpha + \Delta F^{(b)'}(i)_\alpha \quad (45)$$

$$\Delta F^{(a)'}(i)_\alpha = \left[\frac{A^2(i)}{m^2(i)} - \frac{A^0(i)}{m^0(i)}\right]f^0(i)_\alpha + \quad (46)$$
$$\frac{A^2(i)}{m^2(i)}\sum_{j=\sigma}^{N^{imp}} *[A^2(j) - A^0(j)]\varphi^{(1)}(r^0|i,j)_\alpha$$

$$\Delta F^{(b)'}(i)_\alpha = \frac{A^2(i)}{m^2(i)}\sum_{j}^{all} *A^2\left[\sum_{\beta}\Delta r(i,j)_\beta \varphi^{(2)}(r^0|i,j)_{\alpha\beta} + \quad (47)\right.$$
$$\left. \frac{1}{2}\sum_{\beta,\gamma}\Delta r(i,j)_\beta \Delta r(i,j)_\gamma \varphi^{(3)}(r^0|i,j)_{\alpha\beta\gamma}\right] + O[(\Delta r)^3]$$

When $m^0(i)=1$, and $m^2(i)=1$ in equations (46) and (47), these equations are equivalent to equations (28) and (29). For this reason, for the aperiodic system $S^2$ calculation unit 1-5, equation (45) may be prepared in place of equation (22), and MM calculation may be executed assuming that $m^0(i)=1$, and $m^2(i)=1$.

In MD calculations generally, the total energy (kinetic energy+potential energy) of the system is monitored to confirm the energy conservation law. In the calculation method of this embodiment as well, the potential energy can be calculated at the arbitrary time t. For the aperiodic system $S^2$, $E^0_{cell}$ is calculated, and for the reference system $S^0$, $\Delta E$ is calculated. The MD calculation unit 1-7 executes repetitive calculation based on equations (41) to (44) until a time $t_{end}$. The time $t_{end}$ can be arbitrarily designated by the user.

The processing operation in the block diagram (FIG. 1) showing the arrangement of the materials design system of this embodiment has been described in units of blocks. Next, to clarify the connection state among the blocks, MM calculation will be described below with reference to the flow chart shown in FIG. 6. First, physical quantities of the reference system $S^0$ are input to the reference system $S^0$ processing unit 1-1 (step 2-1). The physical quantities are the lattice constants, the number $N^0$ of atoms per unit cell, the coordinates $r^0(h0)_\alpha$ of the $N^0$ atoms, and the potential parameters $A^0(h0)$ of the $N^0$ atoms.

Next, physical quantities of the aperiodic system $S^2$ are input to the aperiodic system $S^2$ processing unit 1-2 (step 2-2). The physical quantities are the number $N^{imp}$ of impurity atoms, the numbers of the $N^{imp}$ impurity atoms ($\sigma$), the potential parameters $A^{imp}(\sigma)$ of the impurity atoms ($\sigma$), and the region $R_{relax}$ where lattice relaxation is taken into consideration.

When these physical quantities are input, the aperiodic system $S^2$ processing unit 1-2 prepares the correspondence list $[S^0 \leftrightarrow S^2]$. The coordinates $r^2(i)_\alpha$ and the potential parameters $A^2(i)$ of the $N^2$ atoms contained in the region $R_{relax}$ in the aperiodic system $S^2$ are set, and the initial values of $\Delta r(i)_\alpha$ are set (step 2-3).

The reference system $S^0$ calculation unit 1-4 calculates the partial potential energies $e^0(h0)$ and the partial forces $f^0(h0)_\alpha$ of the reference system $S^0$ (step 2-4).

The above steps correspond to initial setting. Subsequent steps correspond to the processing operation of repetitive calculation in MM calculation. First, $\Delta E$ and $\Delta F(i)_\alpha$ are calculated by the aperiodic system $S^2$ calculation unit 1-5 (step 2-5). The relaxation amount $\Delta r(i)_\alpha$ is calculated by the MM calculation unit 1-6 using the value $\Delta F(i)_\alpha$ (step 2-6). Accordingly, the aperiodic system $S^2$ processing unit 1-2 updates the value $\Delta r(i)_\alpha$ and calculates the atomic coordinates $r^2(i)_\alpha$ of the aperiodic system $S^2$ (step 2-7).

The repetitive calculation from step 2-5 to step 2-7 is executed until the value $\Delta F(i)_\alpha$ becomes sufficiently small under a certain determination condition. When the determination condition is satisfied, $r^2(i)_\alpha$ is output or displayed as the stable structure (relaxed structure) of the aperiodic system $S^2$ (step 2-8). In steps 2-4 and 2-5, the potential energy $e^0(h0)$ or $\Delta E$ need not always be calculated, and the calculation can be arbitrarily executed in accordance with the purpose of the user.

Figure 6:
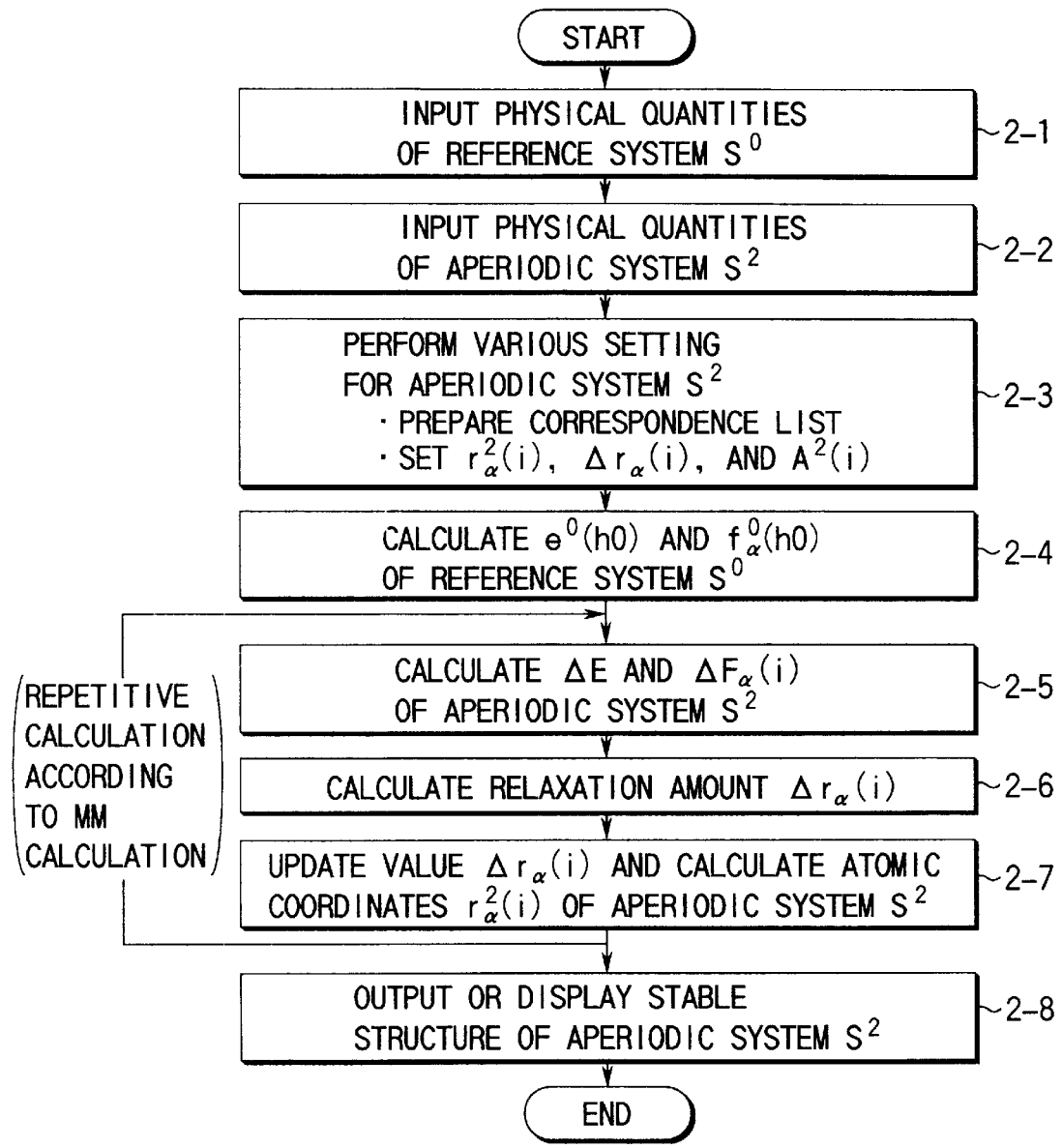
FIG. 6 is a flow chart for executing MM calculation described in the first embodiment.
Figure 7:
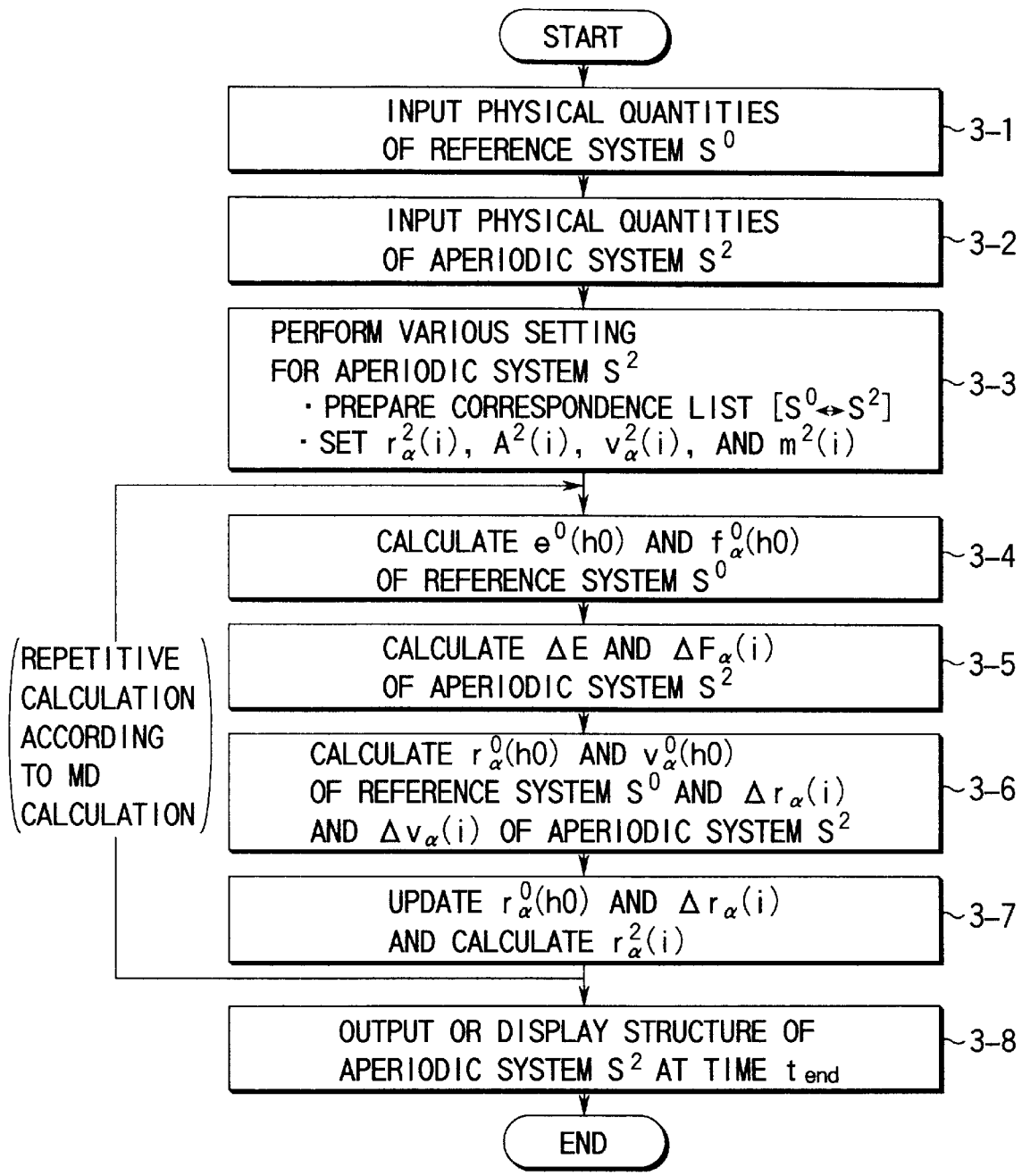
FIG. 7 is a flow chart for executing MD calculation described in the first embodiment.

MD calculation will be described next with reference to the flow chart shown in FIG. 7. From step 3-1 to step 3-3 in FIG. 7, the same processing as described in FIG. 6 in association with MM calculation is executed. However, in this processing associated with MD calculation, the velocities $v^0(h0)_\alpha$ and the masses $m^0(h0)$ of the atoms in the reference system $S^0$ are additionally input in step 3-1. In step 3-2, the masses $m^{imp}(\sigma)$ of the impurity atoms are also input. In step 3-3, setting of the values $v^2(i)_\alpha$ and $m^2(i)$ is performed in addition to the processing in step 2-3.

In the MD calculation, processing from step 3-4 corresponds to repetitive calculation processing. First, $e^0(h0)$ and $f^0(h0)_\alpha$ are calculated by the reference system $S^0$ calculation unit 1-4 (step 3-4), and $\Delta E$ and $\Delta F(i)_\alpha$ are calculated by the aperiodic system $S^2$ calculation unit 1-5 (step 3-5). The MD calculation unit 1-7 calculates $r^0(h0)_\alpha$ and $v^0(h0)_\alpha$ for the reference system $S^0$ and $\Delta r(i)_\alpha$ and $\Delta v(i)_\alpha$ for the aperiodic system $S^2$ (step 3-6). The reference system $S^0$ processing unit 1-1 and the aperiodic system $S^2$ processing unit 1-2 respectively update the values $r^0(h0)_\alpha$ and $\Delta r(i)_\alpha$ and $r^2(i)_\alpha$ is calculated by the aperiodic system $S^2$ processing unit 1-2 (step 3-7).

Processing from step 3-4 to step 3-7 is repeatedly executed until the time tend, and the structure of the aperiodic system $S^2$ at the time tend is output or displayed (step 3-8). In the MD calculation of this embodiment, $r^0(h0)_\alpha$ and $v^0(h0)_\alpha$ for the reference system $S^0$, or $r^2(i)_\alpha$ and $v^2(i)_\alpha$ for the aperiodic system $S^2$ can be output or displayed at an arbitrary time during the repetitive calculation. In steps 3-4 and 3-5, $e^0(h0)$ and $\Delta E$ need not always be calculated every time and can be calculated at an arbitrary time in accordance with the purpose of the user.

Processing as the framework of the materials design system according to this embodiment has been described above.

Modifications of the materials design system of this embodiment will be described below as the second, third, and fourth embodiments.

Second Embodiment

The second embodiment corresponds to the invention described in claim 3.

First, handling of a region $R_{relax}$ where lattice relaxation is taken into consideration, which is set by an aperiodic system $S^2$ processing unit 1-2 will be described.

In the materials design system of the first embodiment, the region $R_{relax}$ is set such that the impurity is positioned almost at the center of the region $R_{relax}$. For this reason, the relaxation amount $\Delta r(i)_\alpha$ is generally large at the central portion of the region $R_{relax}$ and becomes almost zero at the edge of the region $R_{relax}$. In MM calculation and MD calculation, the relaxation amount $\Delta r(i)_\alpha$ is updated by the aperiodic system $S^2$ processing unit 1-2 in each step or at each time point of the repetitive calculation. When the relaxation amount $\Delta r(i)_\alpha$ becomes relatively large even at the edge of the region $R_{relax}$ during a simulation, this means that the range of real lattice relaxation is larger than the region $R_{relax}$, and no proper calculation result can be obtained by this simulation.

Figure 8:
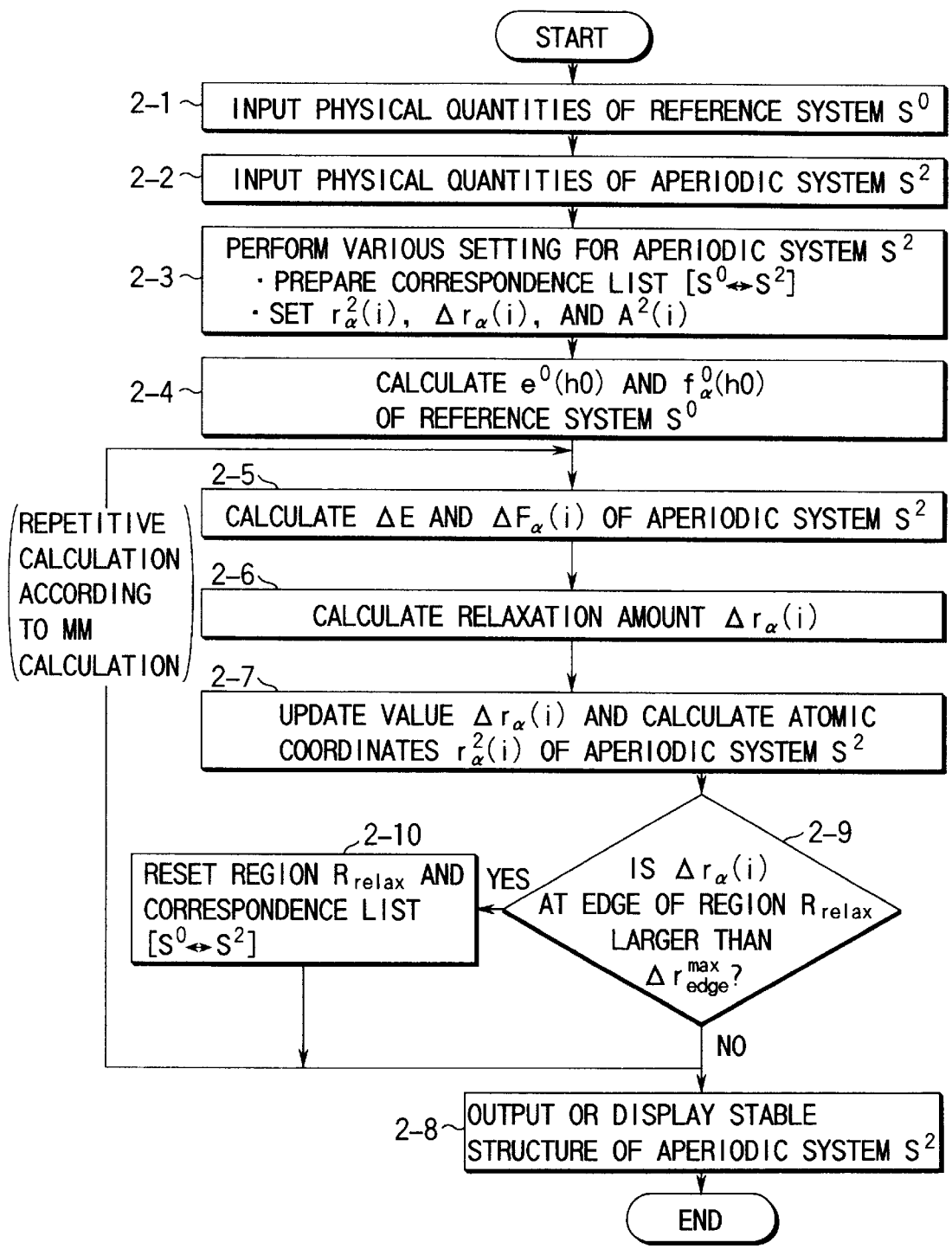
FIG. 8 is a flow chart for executing MM calculation described in the second embodiment.

To prevent this, the calculation method of the second embodiment allows to change the size of the region $R_{relax}$ during the simulation. The region $R_{relax}$ is changed in the following manner. For MM calculation, the flow chart in FIG. 6 changes to that in FIG. 8, so that step 2-9 and 2-10 are added. In FIG. 8, the relaxation amount $\Delta r(i)_\alpha$ is updated in every step of the repetitive calculation in step 2-7, as has already been described. In step 2-9, the value of the relaxation amount $\Delta r(i)_\alpha$ at the edge of the region $R_{relax}$ is determined in accordance with a certain reference. If it is determined that the relaxation amount $\Delta r(i)_\alpha$ at the edge of the region $R_{relax}$ is larger than a reference value $\Delta r^{max}_{edge}$, the flow advances to step 2-10. In step 2-10, the aperiodic system $S^2$ processing unit 1-2 resets the region $R_{relax}$.

This resetting can be executed by, e.g., replacing the radius $R_{relax}$ of the region with a radius $R'_{relax} = R_{relax} + R_{add}$. The newly set region $R'_{relax}$ contains $N'^2 (>N^2)$ atoms. In step 2-10, information associated with the newly counted $(N'^2 - N^2)$ atoms is additionally registered in the correspondence list [S⁰↔S²], and simultaneously, the initial values of $\Delta r(i)_\alpha$ of these atoms are set. After the above processing is performed in step 2-10, the flow returns to the normal repetitive calculation. The above-described reference value $\Delta r^{max}_{edge}$ and $R_{add}$ may be arbitrarily designated by the user or set on the side of the materials design system of this embodiment in advance to increase the calculation efficiency.

Figure 9:
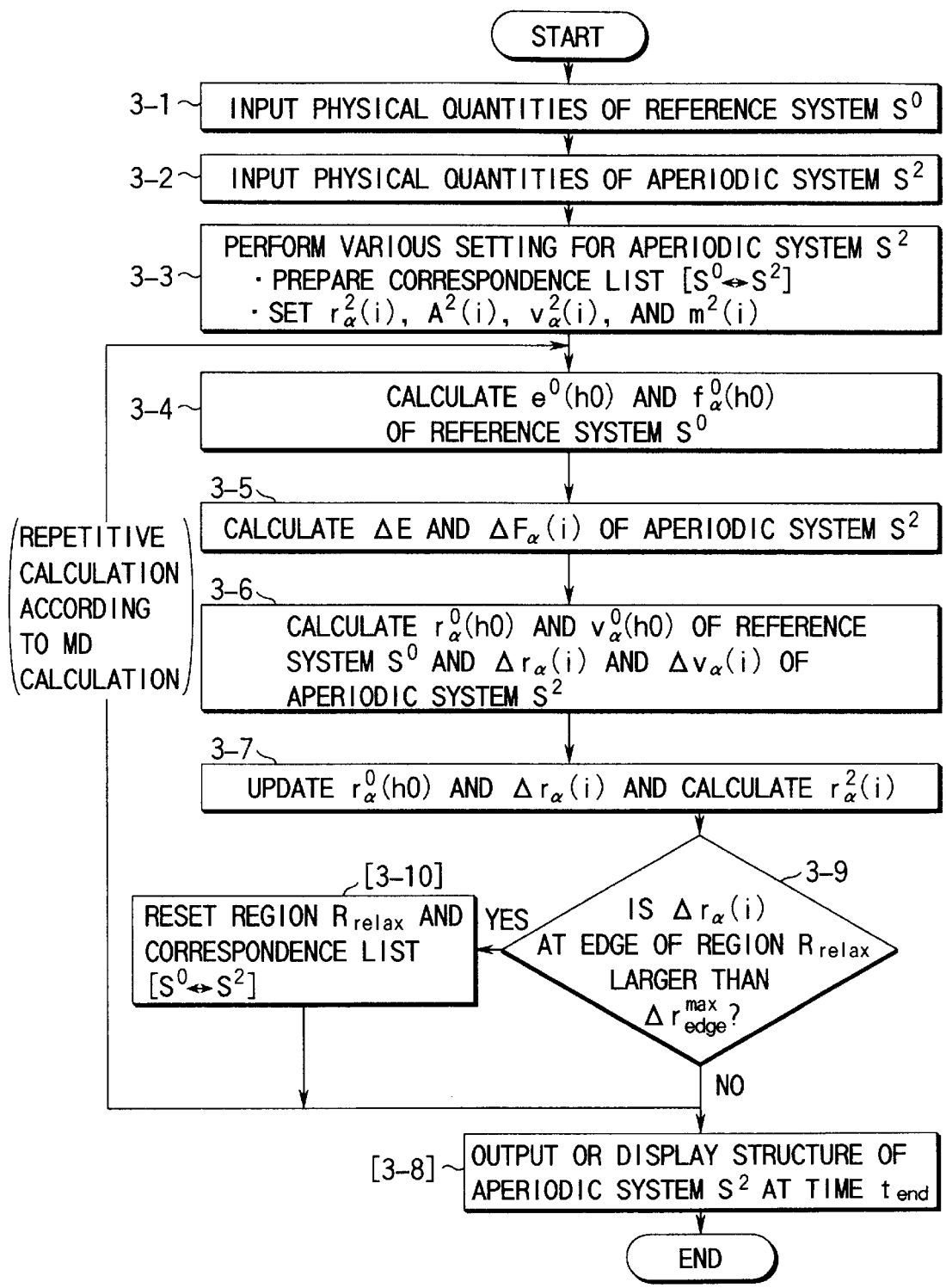
FIG. 9 is a flow chart for executing MD calculation described in the second embodiment.

When the region $R_{relax}$ is appropriately changed following the above procedures, a proper calculation result (relaxed structure) can always be obtained. For MD calculation, the flow chart in FIG. 7 changes to that in FIG. 9. In steps 3-9 and 3-10 added in FIG. 9, the same processing as that in steps 2-9 and 2-10 is performed.

Third Embodiment

The third embodiment corresponds to the invention described in claims 4 and 6.

Processing performed when a relaxation amount $\Delta r(i)_a$ becomes large even at the central portion of a region $R_{relax}$ during a simulation will be described next as the third embodiment.

The materials design system of the first embodiment is characterized in that the atomic coordinates of the aperiodic system $S^2$ are described on the basis of the deviation from the reference system $S^0$, and the physical quantities (the potential energy and the force acting on each atom) of the aperiodic system $S^2$ are approximately calculated by Taylor expansion associated with $\Delta r(i)_\alpha$.

Generally, in Taylor expansion, when the expansion variable is small (near the expansion point), the accuracy of approximation is guaranteed. However, when the expansion variable becomes large (a point separated from the expansion point), the calculation accuracy degrades, as is known. In the materials design system of the first embodiment, the reference system $S^0$ corresponds to the expansion point. When the deviation from the expansion point, i.e., the relaxation amount $\Delta r(i)_\alpha$ becomes large, the calculation accuracy of the physical quantities ($\Delta E$ and $\Delta F(i)_\alpha$) which are calculated using Taylor expansion gradually degrades.

To prevent this, in the third embodiment, accurate calculation can always be performed in accordance with the following procedures. For MM calculation, the flow chart in FIG. 6 changes to that in FIG. 10. In step 2-11 of FIG. 10, it is determined whether the value $\Delta r(i)_\alpha$ for each of the $N^2$ atoms contained in the region $R_{relax}$ is larger than a reference value $\Delta r^{max}_{whole}$. If YES in step 2-11, the flow advances to step 2-12. The reference value $\Delta r^{max}_{whole}$ may be arbitrarily designated by the user or set on the side of the materials design system in advance. A case wherein it is determined that the relaxation amount $\Delta r(i)_\alpha$ of each of $N_{big}$ ($<N^2$) atoms is larger than the reference value $\Delta r^{max}_{whole}$ will be described below. The $N_{big}$ atoms are represented by ($i_{big}$). The atoms of the reference system $S^0$, which are made to correspond to those of the aperiodic system $S^2$ in accordance with the correspondence list [S⁰↔S²], are represented by ($h_{big};\zeta_{big}$).

The following processing is performed when step 2-12 is executed for the first time on the basis of the determination result in step 2-11. In step 2-12, addition/changing processing for the reference system $S^0$ is performed by the reference system $S^0$ processing unit 1-1. First, $N_{big}$ dummy atoms ($h_{dmy}^0$) (to be described as ($h_{dmy};\zeta=0$) hereinafter) are additionally set in the fundamental cell of the reference system $s^0$. With this processing, the number of atoms per unit cell of the reference system $S^0$ becomes $N^0+N_{big}$. The potential parameter and atomic position of the newly set dummy atom ($h_{dmy};\zeta=0$) of the reference system $S^0$ are set in accordance with equations (48) and (49):

$$A^0(h_{dmy};\zeta=0)=0 \tag{48}$$

$$r^0(h_{dmy};\zeta=0)_\alpha = r^2(i_{big})_\alpha \tag{49}$$

In step 2-13, the aperiodic system $S^2$ processing unit 1-2 performs addition/changing processing for the aperiodic system $S^2$. Since, in step 2-12, the dummy atom is arranged in the reference system $S^0$, the number of atoms contained in the aperiodic system $S^2$ also increases. First, atoms contained in the region $R_{relax}$ of the aperiodic system $S^2$ are counted again, and a correspondence list of the dummy atom ($h_{dmy};\zeta$) of the reference system $S^0$ and the corresponding dummy atom ($i_{dmy}$) of the aperiodic system $S^2$ is added to the A correspondence list [S⁰↔S²]. When the number of atoms added to the correspondence list [S⁰↔S₂] is represented by $N_{add}$, $N_{add} > N_{big}$. The specific value $N_{add}$ is determined in consideration of the unit cell size of the reference system $S^0$ and the size of the region $R_{relax}$.

From step 2-13, the number of atoms contained in the region $R_{relax}$ of the aperiodic system $S^2$ is represented by $N^2+N_{add}$. From step 2-13, in addition to the original impurity atom ($\sigma$), the atom ($i_{big}$) and the dummy atom ($i_{dmy}$) are also handled as impurity atoms. Subsequently, the potential parameters of the atom ($i_{big}$) and the dummy atom ($i_{dmy}$) are rewritten or newly set. For the atom ($i_{big}$), the potential parameter is changed as follows:

$$A^2(i_{big})=0 \tag{50}$$

Next, the potential parameter of the dummy atom is newly set. For setting, the following points must be taken into consideration.

The dummy atom ($h_{dmy};\zeta=0$) arranged in the fundamental cell of the reference system $S^0$ in step 2-12 is also arranged in the image cells ($\zeta\neq0$) because of the periodicity of the reference system $S^0$. For this reason, two types of dummy atoms are added to the correspondence list [S⁰↔S²] in step 2-13. One is a dummy atom ($i^{(\zeta=0)}_{dmy}$) which is made to correspond to the dummy atom ($h_{dmy};\zeta=0$) contained in the fundamental cell ($\zeta=0$) of the reference system $S^0$ in the correspondence list [S⁰↔S₂]. The other is a dummy atom ($i^{(\zeta\neq0)}_{dmy}$) which is made to correspond to a dummy atom ($h_{dmy};\zeta\neq0$) contained in the image cell ($\zeta\neq0$) of the reference system $S^0$ in the correspondence list [S⁰↔S₂]. The potential parameters of the two types of dummy atoms of the aperiodic system $S^2$ are set in accordance with equations (51) and (52) below:

$$A^2\left(i^{(\zeta=0)}_{dmy}\right) = A^2(i_{big}) \tag{51}$$

$$A^2\left(i^{(\zeta\neq0)}_{dmy}\right) = 0 \tag{52}$$

The meanings of the two equations are as follows. After step 2-13, the physical quantities of the atom ($i_{big}$) originally present in the aperiodic system $S^2$ are calculated as the physical quantities of the dummy atom ($i^{(\zeta=0)}_{dmy}$). For this purpose, equation (51) is set. For the dummy atom ($i^{(\zeta\neq0)}_{dmy}$) which is set because of the periodicity of the reference system $S^0$ although it is unnecessary, the potential parameter is set to be 0 by equation (52), thereby setting a situation as if the dummy atom ($i^{(\zeta\neq0)}_{dmy}$) were physically absent. For the relaxation amounts of these atoms, the initial value of $\Delta r(i_{dmy})_\alpha$ is set to be 0. For $\Delta r(i_{big})_\alpha$, the value need not be changed because the relaxation amount becomes unnecessary from step 2-13.

The above series of processing operations corresponds to processing of shifting the expansion point of Taylor expansion to make the expansion variable small. More specifically, since the relaxation amount $\Delta r(i_{big})_\alpha$ of the atom $(i_{big})$ becomes large, the dummy atom $(h_{dmy}; \zeta=0)$ is virtually arranged at the position $(r^0(h_{dmy}; \zeta=0)_\alpha = r^0(i_{big})_\alpha + \Delta r(i_{big})_\alpha)$ of the reference system $S^0$. Since the potential parameter $A^0(h_{dmy}; \zeta=0)$ of this dummy atom is set to be 0 by equation (48), the potential energy or force of the reference system $S^0$ does not change due to addition of the dummy atom $(h_{dmy}; \zeta=0)$. After the above processing is performed for the reference system $S^0$, processing for expressing the atomic coordinates of the atom $(i_{big})$ by $r^2(i^{(\zeta=0)}{}_{,dmy})_\alpha$ instead of $r^2(i_{big})_\alpha$ is performed for the aperiodic system $S^2$. More specifically, the coordinates of the atom $(i_{big})$ are represented using $r^2(i^{(\zeta=0)}{}_{,dmy})_\alpha$ as follows:

$$r^2\left(i_{dmy}^{(\zeta=0)}\right)_\alpha = r^0\left(i_{dmy}^{(\zeta=0)}\right)_\alpha + \Delta r\left(i_{dmy}^{(\zeta=o)}\right)_\alpha \tag{53}$$

for $$r^0\left(i_{dmy}^{(\zeta=0)}\right)_\alpha = r^0(h_{dmy}; \zeta=0)_\alpha \tag{54}$$

In MM calculation from step 2-12, as the relaxation amount of the atom $(i_{big})$, $\Delta r(i^{(\zeta=0)}{}_{,dmy})_\alpha$ is obtained instead of $\Delta r(i_{big})_\alpha$.

When the dummy atom $(i_{dmy})$ is arranged, the number of atoms contained in the aperiodic system $S^2$ apparently increases. However, since the original potential parameter $A^2(i_{big})$ of the atom $(i_{big})$ is changed to 0 by equation (50), and the potential parameter of the dummy atom $(i^{(\zeta\neq 0)}{}_{,dmy})$ is also set to be 0 by equation (52), the physical number of atoms contained in the aperiodic system $S^2$ after step 2-13 is equal to that before step 2-13.

It appears that the number of atoms (number of pairs) which must be taken into consideration in calculation of the potential energy or force abruptly increases due to setting of the dummy atoms. However, since the potential parameters A of most dummy atoms are 0, terms associated with the dummy atoms need not be handled in sum calculation by the reference system $S^0$ calculation unit 1-4 or the aperiodic system $S^2$ calculation unit 1-5. Therefore, the increase in calculated amount of the potential energy or force caused by setting of the dummy atoms is not so large.

In step 2-12, the crystal structure of the reference system $S^0$ is apparently changed by setting the dummy atoms. Accordingly, after step 2-13, the flow temporarily returns to step 2-4 to execute calculation of $e^0(h0)$ and $f^0(h0)_\alpha$ again, and then, repetitive calculation based on the normal MM calculation is continuously executed.

When processing from step 2-11 to step 2-13 is performed, MM calculation can be executed with a sufficient calculation accuracy even for the aperiodic system $S^2$ having a very large lattice relaxation. Therefore, the versatility of the materials design system of this embodiment largely increases.

The following points must be taken into consideration. The above-mentioned processing in steps 2-12 and 2-13 is performed in the first cycle of the processing. After the second or subsequent cycles of steps 2-12 and 2-13, the processing changes as follows. If it is determined in step 2-11 twice or more that the relaxation amount $\Delta r(i)_\alpha$ of the same atom is larger than the reference value $\Delta r^{max}{}_{whole}$, the dummy atom corresponding to this atom has already been set in the reference system $S^0$. Therefore, in steps 2-12 and 2-13 from the second cycle, setting of the dummy atom and setting/change of the potential parameter need not be performed, and only equation (49) is calculated. More specifically, only the expansion point $r^0(h_{dmy}; \zeta 0)_\alpha$ need be reset, and the initial value of $\Delta r(i_{dmy})_\alpha$ need be set to be 0 again.

The same processing can also be performed for MD calculation. In this case, the flow chart in FIG. 7 is changed to that in FIG. 11. Processing from step 3-11 to step 3-13 is the same as that from step 2-11 to step 2-13.

Figure 10:
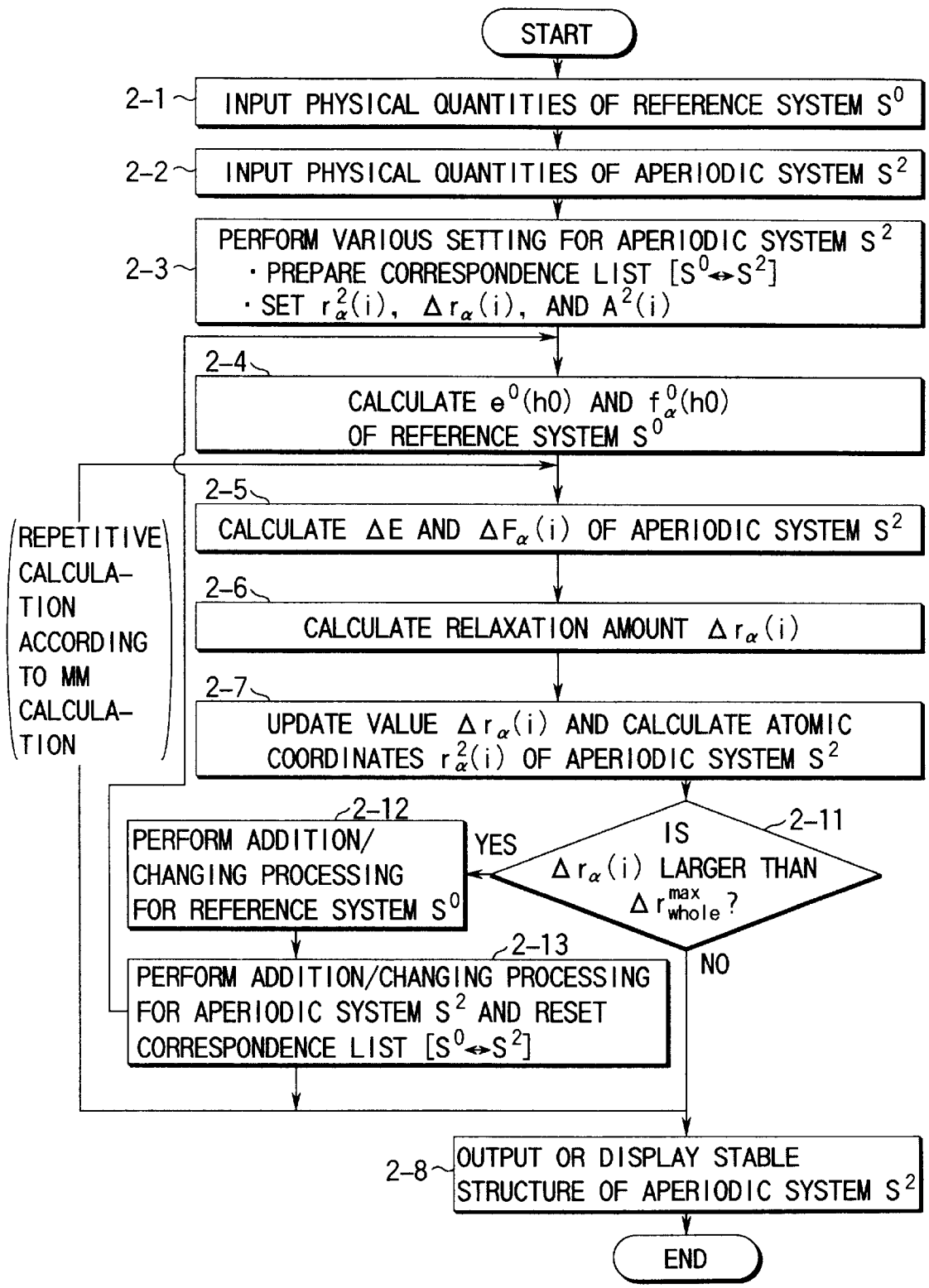
FIG. 10 is a flow chart for executing MM calculation described in the third embodiment.
Figure 11:
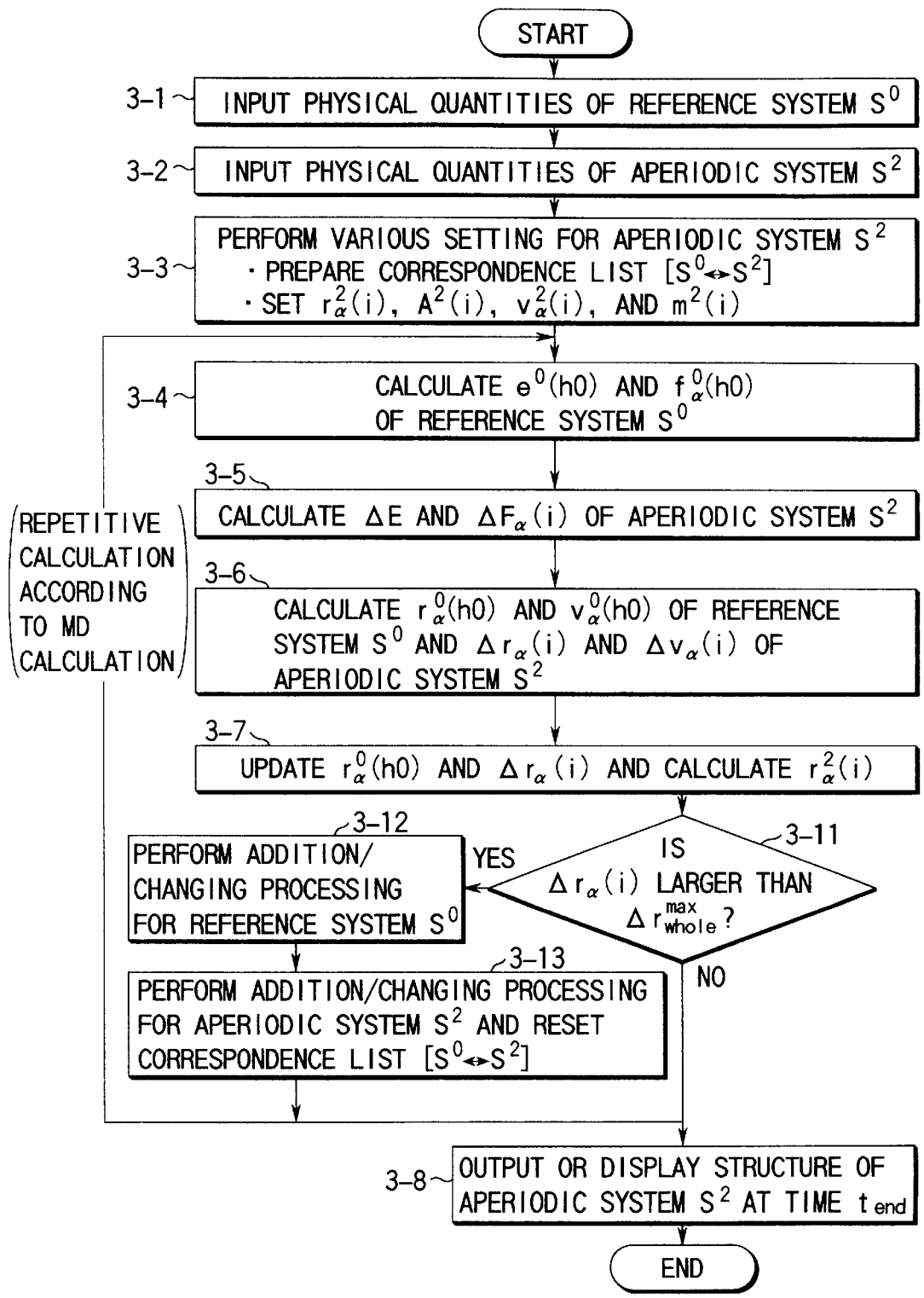
FIG. 11 is a flow chart for executing MD calculation described in the third embodiment.

The flow charts shown in FIGS. 10 and 11 are procedures for realizing highly accurate MM/MD calculation for the aperiodic system $S^2$ in which lattice relaxation with an arbitrary size occurs. To obtain the same function as that of these procedures, dummy atoms may be prepared in advance at the initial setting stage. More specifically, dummy atoms corresponding to all of the $N^2$ atoms (i) contained in the region $R_{relax}$ of the aperiodic system $S^2$ may be set in the reference system $S^0$ and the aperiodic system $S^2$ in advance. With this arrangement, processing of newly setting the dummy atoms in steps 2-12 and 2-13 in FIG. 10 (or steps 3-12 and 3-13 in FIG. 11) can be omitted.

Modifications of the first embodiment associated with MM calculation and MD calculation have been described above as the second and third embodiments. The basic flow chart associated with MM calculation is shown in FIG. 6, and FIGS. 8 and 10 are flow charts of the modifications. For the descriptive convenience, the two modifications have been independently described. However, a materials design system having the both functions can also be formed. For the MD calculation as well, a materials design system having both the functions shown in FIGS. 9 and 11 which show modifications of the basic flow chart in FIG. 7 can be formed.

Fourth Embodiment

The fourth embodiment will be described below.

In this embodiment, handling of interatomic interactions described by functions other than the function given by equation (10) will be described. Processing to be described below can be applied to all the first to third embodiments described above. As the short-range repulsive force between atoms, a Born-Mayer type function represented by equation (55) is often used:

$$\phi(i, j) \propto \exp\left[-\frac{r(i, j)}{B(i) + B(j)}\right] \tag{55}$$

where B(i) is the potential parameter corresponding to the effective radius of an atom (i). The function including the potential parameter B(i) is represented by equation (56):

$$\phi(i,j) = A(i)A(j)\hat{\phi}(B, r|i,j) \tag{56}$$

A function $\psi$ of equation (10) includes no potential parameters. However, in equation (56), a function $\psi\hat{}$ includes a potential parameter B. When an interatomic potential having the function given by equation (56) is to be handled by the materials design system of this embodiment, the following processing is performed.

As in the description of the potential parameter A, the potential parameter B of a reference system $S^0$ is represented by $B^0(h0)$, and the potential parameter B of an aperiodic system $S^2$ is represented by $B^2(i)$. $B^2(i)$ is represented by equation (57):

$$B^2(i) = B^0(i) + \Delta B(i) \tag{57}$$

For $B^0(i)$, equation (58) holds because of the correspondence list and the periodicity of the reference system $S^0$:

$$B^0(i) = B^0(h\zeta) = B^0(h0) \tag{58}$$

When $B^2(i)$ is represented using equation (57), only an impurity atom ($\sigma$) of the aperiodic system $S^2$ has a finite value $\Delta B(\sigma)$ ($\neq 0$), and the values $\Delta B(i)$ of all the remaining atoms are 0.

An aperiodic system $S^2$ calculation unit 1-5 calculates physical quantities $\Delta E$ and $\Delta F(i)_\alpha$ of the aperiodic system $S^2$ as follows. These two quantities are represented by three terms instead of equations (21) and (22):

$$\Delta E = \Delta E^{(a)} + \Delta E^{(b)} + \Delta E^{(c)} \tag{59}$$

$$\Delta F(i)_\alpha = \Delta F^{(a)}(i)_\alpha + \Delta F^{(b)}(i)_\alpha + \Delta F^{(c)}(i)_\alpha \tag{60}$$

For the energy, the respective terms are represented by equations (61) to (64):

$$\Delta E^{(a)} = \sum_{i=\sigma}^{N_{imp}} [A^2(i) - A^0(i)]e^0(i) + \sum_{i=\sigma}^{N_{imp}} [A^2(i) - A^0(i)] \sum_{j(>i)=\sigma}^{N_{imp}} [A^2(j) - A^0(j)]\hat{\varphi}(B^0, r^0 \mid i, j)] \tag{61}$$

$$\Delta E^{(b)} = \sum_{i \in R_{relax}}^{N^2} A^2(i) \sum_{j(>i)}^{all} A^2(j) \left[ \delta r(i,j) \hat{\varphi}^{[1]}(B^2, r^0 \mid i, j) + \frac{1}{2}[\delta r(i,j)]^2 \hat{\varphi}^{[2]}(B^2, r^0 \mid i, j) \right] + O[(\delta r)^3] \tag{62}$$

$$\Delta E^{(c)} = \sum_i A^2(i) \sum_{j(>i)} A^2(j)[\Delta B(i)\hat{\varphi}(B^0, r^0 \mid i, j)_{(i)} + \Delta B(j)\hat{\varphi}(B^0, r^0 \mid i, j)_{(j)}] + O[(\Delta B)^2] \tag{63}$$

$$\hat{\varphi}(B^0, r^0 \mid i, j)_{(i)} = \left. \frac{\partial}{\partial B(i)} \hat{\varphi}(B, r \mid i, j) \right|_{B=B^0, r=r^0} \tag{64}$$

For the force, the terms can be represented as follows:

$$\Delta F^{(a)}(i)_\alpha = [A^2(i) - A^0(i)]f^0(i)_\alpha + A^2(i) \sum_{j=\sigma}^{N^{imp}} *[A^2(j) - A^0(j)]\hat{\varphi}^{(1)}(B^0, r^0 \mid i, j)_\alpha \tag{65}$$

$$\Delta F^{(b)}(i)_\alpha = A^2(i) \sum_j^{all} *A^2(j) \left[ \sum_\beta \Delta r(i,j)_\beta \hat{\varphi}^{(2)}(B^2, r^0 \mid i, j)_{\alpha\beta} + \frac{1}{2} \sum_{\beta,\gamma} \Delta r(i,j)_\beta \Delta r(i,j)_\gamma \hat{\varphi}^{(3)}(B^2, r^0 \mid i, j)_{\alpha\beta\gamma} \right] + O[(\Delta r)^3] \tag{66}$$

$$\Delta F^{(c)}(i)_\alpha = A^2(i) \sum_j *A^2(j) [\Delta B(i)\hat{\varphi}^{*(1)}(B^0, r^0 \mid i, j)_{(i)\alpha} + \Delta B(j)\hat{\varphi}^{*(1)}(B^0, r^0 \mid i, j)_{(j)\alpha}] + O[(\Delta B)^2] \tag{67}$$

$$\hat{\varphi}^{*(1)}(B^0, r^0 \mid i, j)_{(i)\alpha} = \left. \frac{\partial^2}{\partial B(i)\partial r(i,j)_\alpha} \hat{\varphi}(B, r \mid i, j) \right|_{B=B^0, r=r^0} \tag{68}$$

Equations (61), (62), (65), and (66) have the same meanings as those of equations (23), (24), (28), and (29). In equations (61) and (65), the potential parameter $B^0$ of the reference system $S^0$ is used for calculation. In equations (62) and (66), the potential parameter $B^2$ of the aperiodic system $S^2$ is used for calculation.

An important point in handling the interatomic interaction represented by the function given by equation (56) is that the third terms of equations (59) and (60) correspond to terms of higher order in Taylor expansion of $\Delta B$. In equations (63) and (67) which give this term of higher order, terms of first order are rewritten, and $O[(\Delta B)^2]$ represents terms of second or higher arbitrary order.

When the physical quantities $\Delta E$ and $\Delta F(i)_\alpha$ of the aperiodic system $S^2$ are calculated in the above manner, MM/MD calculation using the interatomic potential represented by the general function given by equation (56) can be performed by the calculation method of this embodiment, so that interatomic interactions including the Born-Mayer type interaction can be handled.

For an interatomic interaction represented by a function which is not described by equation (10), the potential energy and force may be calculated by the conventional method, and the resultant potential energy and force may be added to the potential energy and force calculated by the method of the present invention to execute MM/MD calculation.

According to the materials design systems of the above-described first to fourth embodiments, the following effects can be obtained, unlike the conventional supercell method.

(1) Shortening of the computational time
(2) Reduction of the calculation load
(3) Realization of calculation for a perfect isolated system
(4) Realization of calculation without correction for a system where the charge neutrality has been lost These four effects will be described below in more detail on the basis of the actual results of MM calculation.

Figure 12:
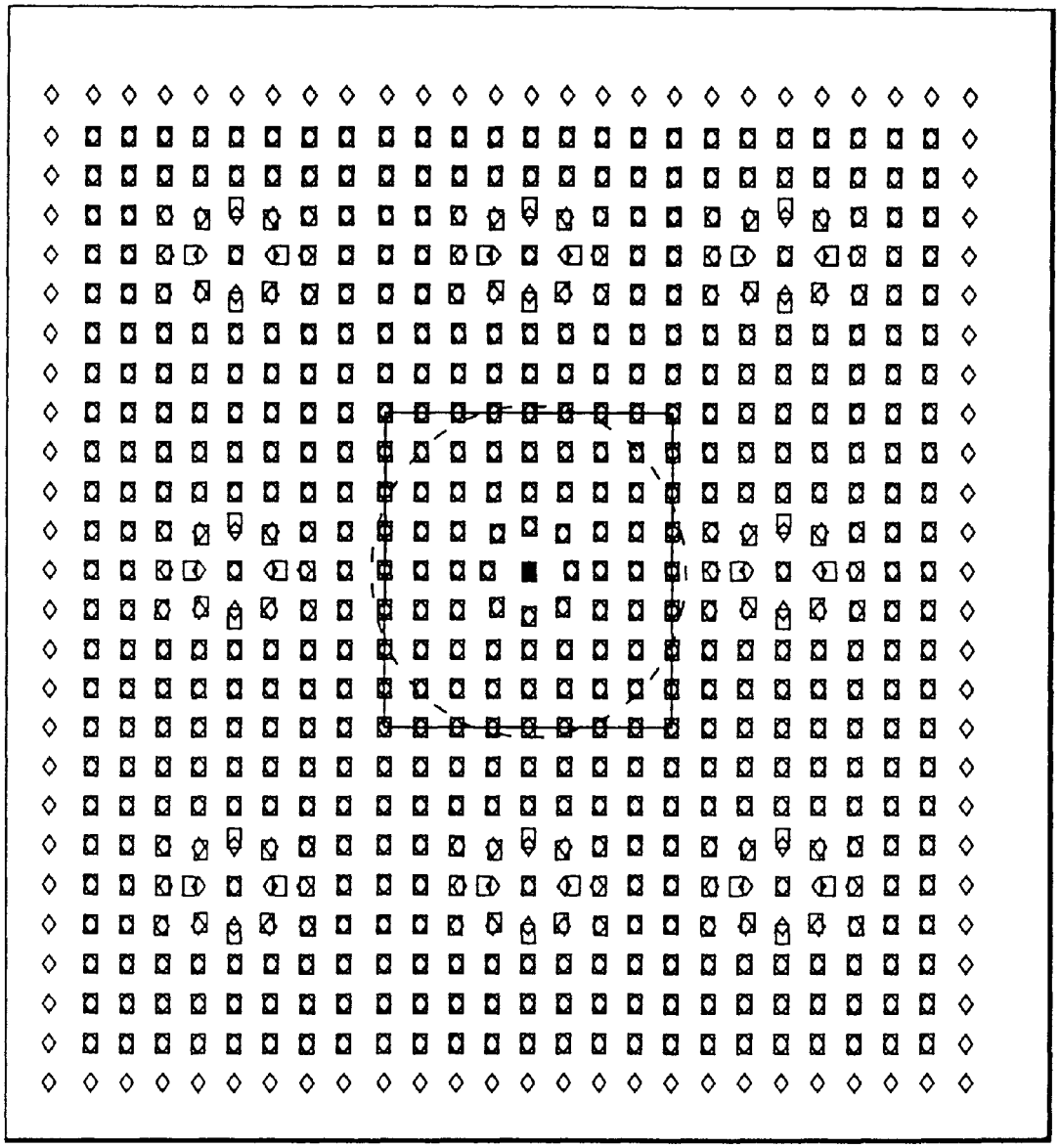
FIG. 12 is a view showing an example of calculation of the stable structure (relaxed structure) by MM calculation of NaCl containing a substitutional impurity ion.

Shortening of the computational time will be described first. For the descriptive convenience, NaCl as a typical ionic crystal will be exemplified as a simple crystal system. The NaCl has an fcc structure in which Na atoms having positive charges and Cl atoms having negative charges are alternated. Assume the reference system $S^0$ as the perfect crystal of NaCl and the aperiodic system $S^2$ in which only one Na ion in the reference system $S^0$ is substituted with a Cl ion. FIG. 12 shows results obtained by calculating the stable structure (relaxed structure) of the aperiodic system $S^2$ by MM calculation based on the calculation method of this embodiment and the conventional supercell method. ◇ indicates the calculation result obtained by the calculation method of this embodiment, and □ indicates the calculation result obtained by the supercell method.

In this calculation example, the unit cell for the supercell method is set to have 512 atoms (solid line). To compare the calculation accuracies between the method of the present invention and the conventional method, for the calculation method of the present invention, a sphere having almost the same volume as that of the unit cell for the supercell method is set as the region $R_{relax}$ where lattice relaxation is taken into consideration (dashed line). The unit cell of the reference system $S^0$ for the calculation method of the present invention is assumed to have eight atoms, i.e., the minimum unit cell as a cubic crystal. In FIG. 12, an atom (solid atom) positioned at the center is a substitutional impurity atom upon substituting Na with Cl. As is apparent from FIG. 12, lattice relaxation occurs around the substitutional impurity atom. The calculation result obtained by the calculation method of the present invention is the same as that obtained by the conventional supercell method.

Attention need be paid to the fact that comparison of the calculation results must be made only for the fundamental cell of the supercell method. The reason for this is as follows. In the supercell method, the image cells also have impurity atoms because of the periodicity. For this reason, in FIG. 12 which shows the calculation result obtained by the supercell method, a total of nine impurity atoms and lattice relaxation around each impurity atom are shown. However, according to the calculation method of this embodiment, a completely isolated impurity system can be handled, so that a proper calculation result can be obtained throughout the whole region of the crystal. In the example shown in FIG.

12, however, since the region of lattice relaxation is not so large, the unit cell containing 512 atoms used for the supercell method has a sufficient size, and for the fundamental cell, the same calculation result as that of the calculation method of this embodiment can be obtained.

The fact that the two calculation results are equal for the fundamental cell means that although approximation calculation based on Taylor expansion is performed in the calculation method of the present invention, a sufficient calculation accuracy can be attained. A more important point is that the calculation method of this embodiment can efficiently shorten the calculation time to about 80 times that of the conventional supercell method. The reason why the calculation time can be largely shortened will be described below.

The calculation time of MM/MD calculation is mainly determined by the number of pairs of atoms which must be taken into consideration in calculation of the potential energy or force. Calculation of the force will be described below. In the supercell method, the force acting on each atom is calculated in accordance with equation (18). In equation (18), $f^0(h0)_\alpha$ is calculated using equation (15). In this calculation, the differential of the interatomic potential must be calculated for all pairs of atoms contained in the unit cell and atoms interacting with the atoms in the crystal. The number of pairs largely increases when the unit cell size increases. In the supercell method, when the unit cell size is increased to realize a "system containing an isolated impurity", the calculation time largely increases.

To prevent this, according to the present invention, calculation of equation (15) which requires a long calculation time is executed only for a small unit cell (e.g., the minimum unit cell of the crystal), thereby allowing to short the calculation time. This is specifically realized by calculation of $\Delta F(i)_\alpha$ based on equation (22). As has been already described, this calculation is given by equations (28) and (29).

First, $f^0(h0)_\alpha$ is calculated in accordance with equation (28). This is the physical quantity of the reference system $S^0$. Since the unit cell of the reference system $S^0$ is small, the calculation amount is not so large.

Next, $$\sum_{i=\sigma}^{N^{imp}}$$

included in equation (28) is the sum only for the impurity atoms ($\sigma$). Since the number of impurity atoms is generally several to several ten, the calculation amount is very small.

$$\sum_{j}^{all}$$

included in equation (29) means that calculation is performed for all pairs of atoms contained in the region $R_{relax}$ and atoms interacting with the atoms. In this case, the fact that the term to be calculated in this sum includes $\Delta r(ij)_\alpha$ must be taken into consideration. This $\Delta r(ij)_\alpha$ abruptly approaches 0 as it is separated from the impurity. For this reason, the number of pairs which must be taken into consideration in $$\sum_{j}^{all}$$

is not so large, and convergence of calculation is very good.

Due to the above-described reason, the number of pairs which must be taken into consideration in the calculation method of this embodiment is much smaller than that of the conventional supercell method, so that the calculation time can be shortened. In calculation of $f^0(h0)_\alpha$ of equation (28), the Ewald method (reference 1) can be used for the Coulomb interaction. Alternatively, the efficient method used in the prior art can be directly applied. In addition, $f^0(i)_\alpha$ is a physical quantity of the reference system $S^0$. For this reason, when an equilibrium structure is to be used as the reference system $S^0$ in MM calculation, calculation need be performed once at the initial setting stage, and thereafter, can be omitted. Therefore, the calculation time can be further shortened.

The above description about calculation of the force also applies to calculation of the potential energy $\Delta E$. Due to the above-described reason, according to the calculation method of the present invention, the calculation time can be made much shorter than that of the conventional supercell method.

Figure 13:
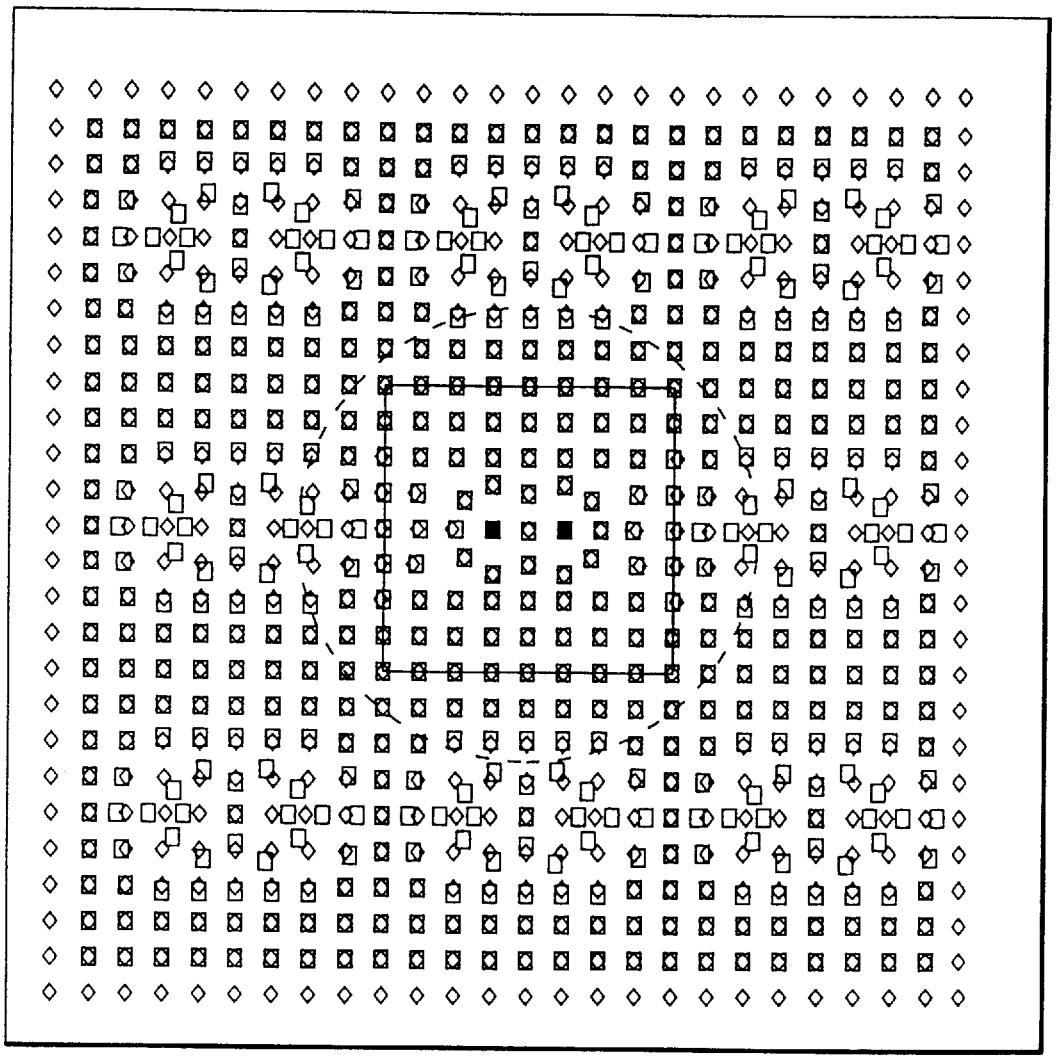
FIG. 13 is a view showing an example of calculation of the stable structure (relaxed structure) by MM calculation of NaCl containing two substitutional impurity ions.

The second effect of the present invention, i.e., reduction of the calculation load will be described next. NaCl will be exemplified again, and this time, a system in which two Na ions are substituted with Cl ions is assumed. FIG. 13 shows results obtained by simulating the stable structure of this system by MM calculation based on the calculation method of the present invention and the conventional supercell method (two solid atoms indicate impurity atoms).

In FIG. 13, the two calculation results do not match even for the fundamental cell of the supercell method and, more particularly, at the edge of the fundamental cell, unlike the above-described FIG. 12. In image cells adjacent to the fundamental cell, the shift between the two calculation results becomes more conspicuous. This means that, in the example shown in FIG. 13, since the range of lattice relaxation is large, the unit cell (containing 512 atoms) assumed for the supercell method has no sufficient size, and the calculation result obtained by the supercell method cannot give a proper stable structure (relaxed structure). To confirm whether the calculation result obtained by the supercell method is correct, calculation must be performed a number of times while changing the unit cell size. An appropriate unit cell size is predicted and set, and calculation is performed for confirmation. Accordingly, not only the excess calculation load but also an excess calculation time is required for the supercell method.

On the other hand, in the calculation method of the present invention, the region $R_{relax}$ where lattice relaxation is taken into consideration can be appropriately changed during the simulation, as described above in the flow charts shown in FIGS. 8 and 9. Even when the initially set region $R_{relax}$ is smaller than the actual lattice relaxation range, a proper calculation result (relaxed structure in case of MM calculation) can be obtained by performing only one simulation, so that the load on the user and the calculation time can be reduced. Actually, in the calculation example based on the calculation method of the present invention shown in FIG. 13, the region $R_{relax}$ where lattice relaxation is taken into consideration is larger than that of the example shown in FIG. 12.

The third effect of the calculation method of this embodiment will be described next. In the conventional supercell method, the impurity arranged in the fundamental cell is inevitably present in the peripheral image cells because of the periodic boundary condition, so the state of an "isolated impurity" cannot be properly realized unless the unit cell size is not sufficiently large. Normally, the unit cell size can hardly be increased due to the balance to the calculation time, and calculation must often be performed for an approximate system (a system in which interaction between impurities cannot be completely neglected). An example of unsatisfactory approximation corresponds to the calculation result of the supercell method shown in FIG. 13.

On the other hand, according to the calculation method of the present invention, the aperiodic system $S^2$ has no periodicity, so the interaction with the "impurity" contained in the image cells is not originally present in the aperiodic system $S^2$, unlike the supercell method. For this reason, simulation for a "completely isolated impurity" can always be performed.

Finally, the fourth effect of the present invention will be described. In the supercell method, when the sum of charges in the unit cell is shifted from 0 by setting impurity atoms, the charges of the impurity atoms themselves peripheral atoms must be corrected. In such a case, no real charge distribution can be handled. In the calculation example by the supercell method shown in FIG. 13, two Na ions are substituted with Cl ions, and the sum of charges per unit cell is −4. To correct the charges, in the calculation shown in FIG. 13, a charge of +4/512 is uniformly added to all atoms in the unit cell in the supercell method. When the charge distribution is corrected in this way, the potential energy of the system, the equilibrium lattice constant, or the equilibrium atomic coordinates undesirably change.

However, the aperiodic system $S^2$ need not satisfy this charge neutrality condition. Therefore, calculation can be executed even for a system where the charge neatrality has been lost as shown in FIG. 12 or 13, without artificially correcting charges.

Fifth Embodiment

MD Calculation for Periodic System

The fifth embodiment of the present invention will be described below with reference to the accompanying drawing.

The fifth embodiment corresponds to the invention described in claim 5.

Prior to a description of this embodiment, calculation of a force for an infinite system with a periodic boundary condition will be briefly described.

An interatomic interaction acting between an atom (hζ) and an atom (h'ζ') is represented by $\phi(h\zeta, h'\zeta')$ where (hζ) represents the hth atom contained in the ζth unit cell, an a component of a force acting on an atom (h0) contained in a unit cell (ζ=0) is represented by equation (69):

$$F(h0)_\alpha = \sum_{h'}^{N} \sum_{\zeta'}^{all} \left[ -\frac{\partial \phi(h\zeta, h'\zeta')}{\partial r(h\zeta, h'\zeta')_\alpha} \right] \quad (69)$$

where $r(h\zeta, h'\zeta')_\alpha$ ($= r(h\zeta)_\alpha - r(h'\zeta')_\alpha$) is the a component of a positional vector between the two atoms, $$\frac{\partial \phi(h\zeta, h'\zeta')}{\partial r(h\zeta, h'\zeta')_\alpha}$$

is the differential coefficient obtained by differentiating the interatomic potential by atomic coordinates, N is the number of atoms per unit cell, $$\sum_{h'}^{N}$$

is the sum for N atoms contained in a unit cell, and $$\sum_{\zeta'}^{all}$$

is the sum for equivalent atoms which have the same value h' contained in different unit cells. Calculation of the latter $$\sum_{\zeta'}^{all}$$

corresponds to the above-described lattice sum, and "all" means that sum calculation is performed for pairs as many as possible until the convergence attains a sufficient accuracy.

The lattice sum $$\sum_{\zeta'}^{all}$$

needs the longest computational time in the calculation of equation (69), and the above-described Ewald method is essentially applied to an $r^{-n}$ long-range interaction such as a Coulomb interaction. Most execution time required for MD calculation is spent to calculate the force according to equation (69), and the calculation time can be estimated as follows.

In a system containing N atoms per unit cell, the three components of the force acting on each of the N atoms are calculated using the above equation, so the calculation amount is represented by $3 \times N \times N \times N_{all}$. The second N corresponds to calculation of $$\sum_{h'}^{N},$$

and $N_{all}$ corresponds to calculation of $$\sum_{\zeta'}^{all}.$$

The Ewald method is generally applied to calculation of the lattice sum, as described above. The calculation amount can hardly be represented as a specific numerical value, and therefore, represented by $N_{all}$ in this case. The value $N_{all}$ is always larger than the number N of atoms per unit cell ($N_{all} \gg N$). In MD calculation, repetitive calculation must be performed generally several thousand to several ten thousand times to track the change over time in the system. Therefore, the total calculation amount for the force is $N \times N \times N_{all} \times N_{step}$ (coefficient "3" is omitted).

This calculation amount increases in proportion to the square of the number N of atoms per unit cell. For this reason, when the cell size increases, the calculation time becomes much longer. The cell size generally used for the MD calculation (supercell method) corresponds to several hundred to several thousand atoms. Recently, calculations for a system containing several million or more atoms are also performed by using a super parallel computer. The number N of atoms per unit cell is determined depending on the system. For a periodic system and an aperiodic system, the lower limit values of N are as follows.

Periodic system . . . $N_{T>0}$ which gives a temperature fluctuation with a statistically allowable accuracy.

Aperiodic system . . . $N_{SC}$ which gives a sufficiently large cell size capable of neglecting the interaction between disorders artificially arranged in the unit cells due to the periodic boundary condition.

The periodic system will be described first. In MD calculation, the motion of atoms or molecules is analyzed at a finite temperature (T>0 K). For this reason, each atom microscopically vibrates due to the temperature effect. Inversely speaking, since this vibration gives the temperature of the system, the temperature of the system can be calculated at each time point (a step of repetitive calculation) of the MD calculation using the vibration (velocity) of each atom. The temperature fluctuation (time dependence) is determined depending on (in proportion to $1/\sqrt{N}$) of the number of independent atoms in the system (when the periodic boundary condition is set, the number N of atoms per unit cell).

To realize a designated temperature T with a small number N of atoms per unit cell, each atom must excessively largely vibrate. Consequently, the temperature fluctuation increases in proportion to $1/\sqrt{N}$, and this MD calculation handles a physically abnormal system.

For this reason, for the periodic system, the MD calculation must be executed in a system having a cell size larger than the number $N_{T>0}$, with which a small temperature fluctuation can be given with a statistically allowable accuracy.

When the aperiodic system is to be approximately handled by the supercell method, a virtual disorder is arranged in each unit cell due to the periodic boundary condition. To represent the real aperiodic system (system without interaction between disorders), a sufficiently large unit cell size must be set. $N_{SC}$ for giving the sufficiently large unit cell has a larger value in a system having a long-range interaction.

Figure 14:
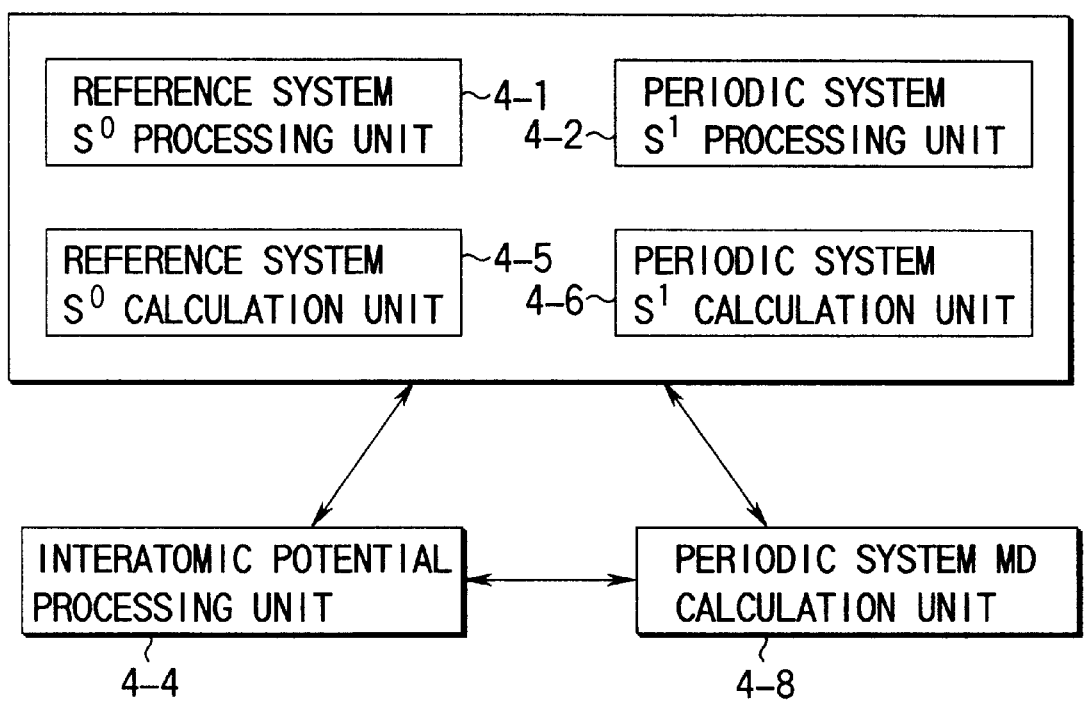
FIG. 14 is a block diagram showing the arrangement of a materials design system for executing MD calculation for a periodic system $S^1$ according to the fifth embodiment.

The fifth embodiment will be described below on the basis of the above-described procedures of MD calculation. FIG. 14 is a block diagram showing the arrangement of a materials design system for executing MD calculation for a periodic system $S^1$. The materials design system comprises a reference system $S^0$ processing unit 4-1, a periodic system $S^1$ processing unit 4-2, an interatomic potential processing unit 4-4, a reference system $S^0$ calculation unit 4-5, a periodic system $S^1$ calculation unit 4-6, and a periodic system MD calculation unit 4-8. In the fifth embodiment, the processing operations of the respective blocks in FIG. 14 will be described first, and then, the flow of processing of executing MD calculation for the periodic system $S^1$ according to the present invention will be described with reference to flow charts.

Processing performed by the reference system $S^0$ processing unit 4-1 shown in FIG. 14 will be described first. The reference system $S^0$ processing unit 4-1 holds/processes the crystal structure, the potential parameters, and the like of the reference system $S^0$. The reference system $S^0$ corresponds to the structure of the periodic system $S^1$ at the absolute zero (T=0 K) and has a periodicity. The unit (unit cell $U^0$) of the periodicity of the reference system $S^0$ is given by, e.g., the minimum unit cell of a crystal. As will be described later, the unit cell $U^0$ is the constituent unit of a unit cell $U^1$ of the periodic system $S^1$.

The reference system $S^0$ processing unit 4-1 receives the lattice constants of the reference system $S^0$, the number $N^0$ of atoms per unit cell $U^0$, atomic coordinates $r^0(h0)_\alpha$ of $N^0$ atoms, potential parameters $A^0(h0)$, and masses $m^0(h0)$ and holds these values.

The number $N^0$ of atoms per unit cell $U^0$ corresponds to the above-described $N_{T=0}$. A suffix $(h\zeta)$ represents the hth atom in the $\zeta$th unit cell of the reference system $S^0$. All the unit cells are equivalent under the periodic boundary condition. Therefore, prominence is given to the 0th ($\zeta=0$) unit cell, and the atomic coordinates, the potential parameters, and the like are designated for this fundamental cell ($\zeta=0$).

The atomic coordinate $r^0(h0)_\alpha$ represents the $\alpha$ component of the coordinate of the hth atom contained in the fundamental cell ($\zeta=0$). Coordinate $r^0(h\zeta)_\alpha$ of an atom contained in an arbitrary unit cell is calculated from the lattice constant (fundamental translation vectors $a_{\lambda\alpha}$) and relative coordinates $x_\lambda(h)$ of the atom as follows:

$$r^0(h\zeta)_\alpha = r^0(\zeta)_\alpha + r^0(h)_\alpha \qquad (70)$$

$$r^0(\zeta)_\alpha = \zeta_1 a_{1\alpha} + \zeta_2 a_{2\alpha} + \zeta_3 a_{3\alpha} \zeta\lambda: \qquad (71)$$

$$r^0(h)_\alpha = x_1(h)a_{1\alpha} + x_2(h)a_{2\alpha} + x_3(h)a_{3\alpha} \qquad (72)$$

$$0 \leq x_\lambda(h) \leq 1$$

where $\lambda$ is the suffix for discriminating the three fundamental translation vectors.

The reference system $S^0$ processing unit 4-1 may receive the fundamental translation vectors $a_{\lambda\alpha}$ and the relative coordinates $x_\lambda(h)$ instead of atomic coordinates $r^0(h0)_\alpha$ and set the atomic coordinates $r^0(h0)_\alpha$ in accordance with the above equations. For the atomic coordinates $r^0(h0)_\alpha$, the potential parameters $A^0(h0)$, and the masses $m^0(h0)$, equations (73) to (75) hold for an arbitrary cell $\zeta$ caused by the periodic boundary condition:

$$r^0(h\zeta)_\alpha = r^0(h0)_\alpha + r^0(\zeta)_\alpha \qquad (73)$$

$$A^0(h\zeta) = A^0(h0) \qquad (74)$$

$$m^0(h\zeta) = m^0(h0) \qquad (75)$$

Handling of the potential parameter $A^0$ is associated with the processing operation of the interatomic potential processing unit 4-4 shown in FIG. 14 and will be described later in detail in association with the interatomic potential processing unit 4-4.

The periodic system $S^1$ processing unit 4-2 shown in FIG. 14 will be described next. The periodic system $S^1$ processing unit 4-2 holds/processes the structure, the potential parameters, and the like of the periodic system $S^1$. The periodic system $S^1$ is a system in which microscopic vibration of each atom in the reference system $S^0$, which is caused by the temperature effect, is taken into consideration. The unit cell $U^1$ of the periodic system $S^1$ is constituted by M unit cells $U^0$ of the reference system $S^0$.

As described above, when the number of atoms (corresponding to $N_{T>0}$) contained in the unit cell $U^1$ is small, the computational time necessary for MD calculation can be short. However, since the temperature fluctuation of the system increases, MD calculation with a statistically required accuracy cannot be realized. For this reason, in MD calculation, generally, a system whose number of atoms per unit cell is several hundred or more is used for calculation.

The periodic system $S^1$ processing unit 4-2 receives the lattice constants of the periodic system $S^1$, the number $N^1$ of atoms per unit cell $U^1$, atomic coordinates $r^1(k0)_\alpha$ of $N^1$ atoms, velocities $v^1(k0)_\alpha$, potential parameters $A^1(k0)$, and masses $m^1(k0)$ and holds these values. The number $N^1$ of atoms per unit cell $U^1$ corresponds to the above-described $N_{T>0}$.

Instead of directly designating $N^1$, a temperature fluctuation $\Delta T$ with an accuracy required by the user may be designated, and $N^1$ may be determined from the temperature fluctuation $\Delta T$.

A suffix (k$\xi$) represents the kth atom in the $\xi$th unit cell of the periodic system $S^1$. All the unit cells are equivalent under the periodic boundary condition. Therefore, prominence is given to the 0th ($\xi$=0) unit cell, and the atomic coordinates, the potential parameters, and the like are designated for this fundamental cell ($\xi$=0).

As described above, the unit cell $U^1$ of the periodic system $S^1$ is constituted by $M(=M_1 \times M_2 \times M_3)$ unit cells $U^0$ of the reference system $S^0$. Atoms in the periodic system $S^1$ are made to correspond to those of the reference system $S^0$ in one-to-one correspondence. The correspondence can be made for an atom (k0) in the fundamental cell ($\xi$=0) of the periodic system $S^1$ and an atom (h$\zeta$) in the reference system $S^0$ using a relation $k=h+\zeta N^0$ ($k=1, \ldots, N^1$). This information is stored in a correspondence list $[S^0 \leftrightarrow S^1]$.

Figure 16:
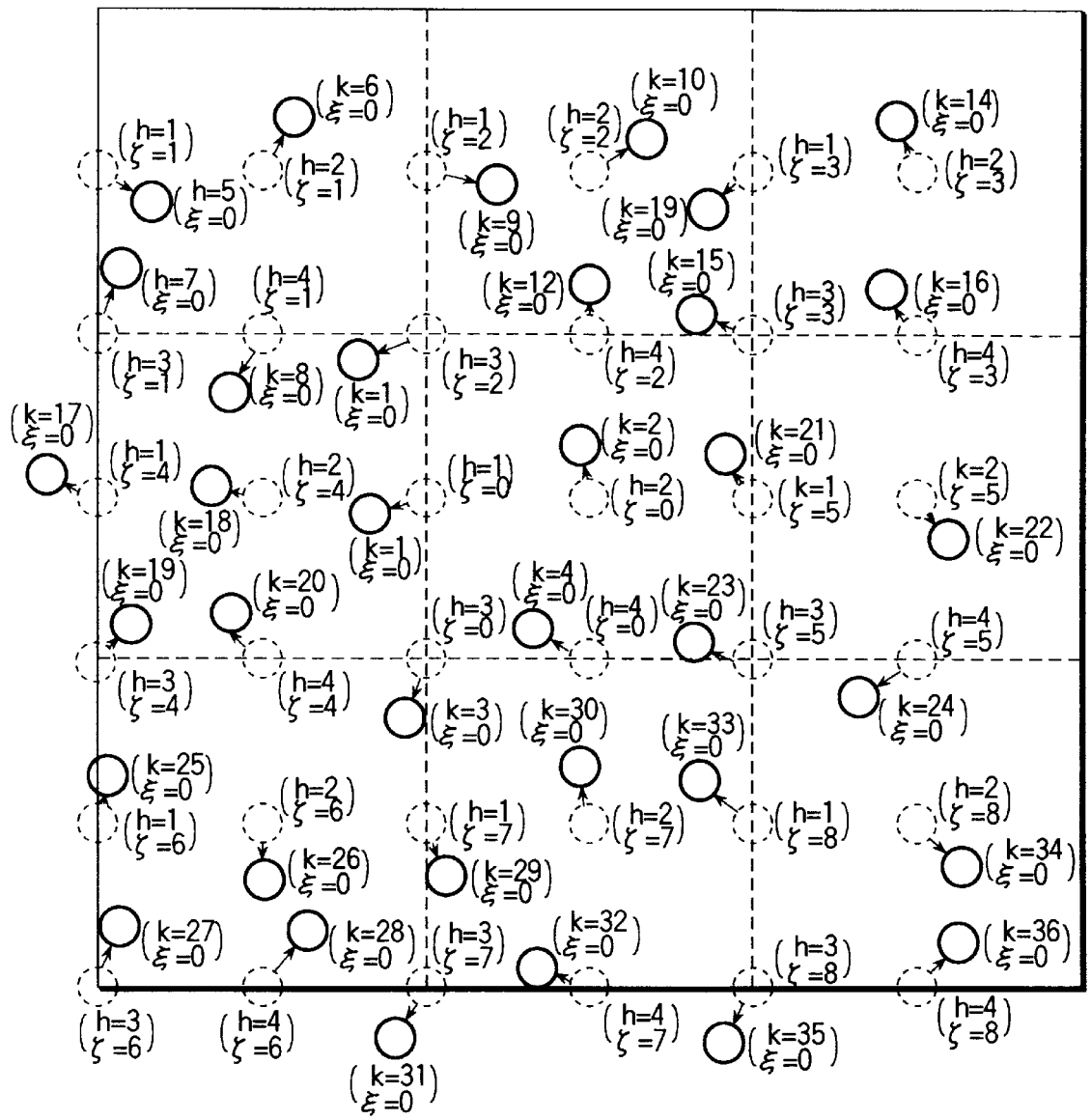
FIG. 16 is a view for explaining the relationship between the reference system $S^0$ and the periodic system $S^1$.

FIG. 16 shows an example of the correspondence between the reference system $S^0$ (constituent atoms and unit cells are indicated by dashed lines) and the periodic system $S^1$ (constituent atoms and unit cells are indicated by solid lines). FIG. 16 shows a two-dimensional structure in which the unit cell $U^1$ of the periodic system $S^1$ is constituted by nine (M=9) unit cells $U^0$ of the reference system $S^0$.

FIG. 18 shows the correspondence list $[S^0 \leftrightarrow S^1]$ for FIG. 16. In the example shown in FIG. 16, the number $N^0$ of atoms per unit cell $U^0$ of the reference system $S^0$ is 4, and the number $N^1$ of atoms per unit cell $U^1$ of the periodic system $S^1$ is 36. In the periodic system $S^1$ processing unit 4-2, instead of directly inputting the values of the lattice constants of the periodic system $S^1$, the number $N^1$ of atoms per unit cell $U^1$, the atomic coordinates $r^1(k0)_\alpha$ of $N^1$ atoms, the potential parameters $A^1(k0)$, and the masses $m^1(k0)$ by the user, information ($M_1 \times M_2 \times M_3$) may be input as follows:

The number $N^1$ of atoms per unit cell $U^1$ is calculated as $N^0 \times M$ on the basis of this information, thereby preparing the correspondence list $[S^0 \leftrightarrow S^1]$. At this time, in the above relation $k=h+\zeta N^0$, assume that $\zeta=(\zeta_1,\zeta_2,\zeta_3)$, ($\zeta_1=1,\ldots,M_1$, $\zeta_2=1,\ldots,M_2$, $\zeta_3=1,\ldots,M_3$). In addition, on the basis of the correspondence list $[S^0 \leftrightarrow S^1]$ and the periodicity of the reference system $S^0$, the initial values of the atomic coordinates $r_1(h0)_\alpha$, the values of the potential parameters $A^1(h0)$ and the masses $m^1(h0)$ may be set as follows:

$$r^1(k0)_\alpha = r^0(h\zeta)_\alpha = r^0(h0)_\alpha + r^0(\zeta)_\alpha \tag{76}$$

$$A^1(k0) = A^0(h\zeta) = A^0(h0) \tag{77}$$

$$m^1(k0) = m^0(h\zeta) = m^0(h0) \tag{78}$$

For the velocities $v^1(k0)_\alpha$, when MD calculation is to be performed at a temperature T, initial velocities corresponding to this temperature must be set. Initial velocities for giving the temperature T, which are designated by the user, may be automatically generated by the materials design system of the present invention or appropriately set by the user.

The interatomic potential processing unit 4-4 shown in FIG. 14 holds a function representing an interatomic interaction. In this embodiment, the interatomic interaction acting between the atom (i) and the atom (j) is described by a function (79) below:

$$\phi(i,j) = A(i)A(j)\phi(r|i,j) \tag{79}$$

where A(i) corresponds to potential parameters $A^0(h\xi)$, $A^1(k\xi)$, and $A^2(i)$ described in the description of the reference system $S^0$ processing unit 4-1, the periodic system $S^1$ processing unit 4-2, and the aperiodic system $S^2$ processing unit 4-3. When $\phi(i,j)$ represents a Coulomb interaction, A(i)=qi (qi is the charge of the atom (i)), and $\psi(r|i,j)=1/r(i,j)$ (r(i,j) is the interatomic distance between the atom (i) and the atom (j)).

In addition to the Coulomb interaction, a van der Waals force, a multipole interaction, and the like are interatomic interactions represented by a function such as equation (79). These interactions are generally taken into consideration in MD calculations, and equation (79) is the representative function of the interatomic interactions. The materials design system of the present invention can simultaneously handle a plurality of interatomic interactions such as Coulomb interaction+van der Waals force+short-range repulsive force. In this case, the interatomic interaction $\phi(i,j)$ acting between the atom (i) and the atom (j) is described by equations (80) and (81):

$$\phi(i,j) = \sum_\mu \phi_\mu(i,j) \tag{80}$$

$$= \sum_\mu A_\mu(i) A_\mu(j) \phi_\mu(r|i,j) \tag{81}$$

Regardless of whether only one or a plurality of interatomic interactions are to be taken into consideration, handling is performed in the same manner. Therefore, a suffix $\mu$ for discriminating the interatomic interactions will be omitted for the above-described reference system $S^0$ processing unit 4-1 and the periodic system $S^1$ processing unit 4-2 and the following description. In this embodiment, a description associated only with an interatomic potential will be made. The materials design system of the present invention can also handle an intermolecular potential.

In the materials design system of the present invention, to perform MD calculation for the periodic system $S^1$, the energies of the reference system $S^0$ and the periodic system $S^1$ and a force acting on each atom are calculated. This method will be described below.

The processing operation of the reference system $S^0$ calculation unit 4-5 shown in FIG. 14 will be described. The reference system $S^0$ calculation unit 4-5 calculates the potential energy of the reference system $S^0$ and the force acting on each atom. First, the $\alpha$ component of the positional vector $r^0(h\zeta,h'\zeta')_\alpha$ between two atoms is defined as follows:

$$r^0(h\zeta,h'\zeta')_\alpha = r^0(h\zeta)_\alpha - r^0(h'\lambda')_\alpha \tag{82}$$

The position vector between two atoms of the periodic system $S^1$ or aperiodic system $S^2$ (to be described later) is also defined by equation (82). The reference system $S^0$ calculation unit 4-5 calculates physical quantities represented by $e^0(h0)$ and $f^0(h0)_\alpha$ using equations (83) to (85) below:

$$e^0(h0) = \sum_{h'}^{N^0} \sum_{\zeta'}^{all} A^0(h'\zeta') \varphi(r^0|h0,h'\zeta') \tag{83}$$

$$f^0(h0)_\alpha = \sum_{h'}^{N^0} \sum_{\zeta'}^{all} A^0(h'\zeta')\varphi'(r^0 \mid h0, h'\zeta')_\alpha \qquad (84)$$

$$\varphi'(r^0 \mid h\zeta, h'\zeta')_\alpha \equiv -\frac{\partial \varphi(r^0 \mid h\zeta, h'\zeta')}{\partial r^0(h\zeta, h'\zeta')_\alpha} \qquad (85)$$

In the above equations, $$\sum^{all}$$

means that the sum is calculated for terms as many as possible until the convergence of the sum attains a sufficient accuracy. The terms added by this sum correspond to the interatomic potential or the differential coefficient of the interatomic potential. As the interatomic distance increases, the value of each term generally becomes small. Therefore, $$\sum^{all}$$

means that interactions are taken into consideration for sufficiently far atoms where the interatomic interactions become negligible. For the Coulomb interaction, the Ewald method may be used for the lattice sum of equations (83) and (84) to increase the calculation efficiency. The Ewald method can be also applied to calculation of lattice sum of interactions whose function is given by $r^{-n}$. When $e^0(h0)$ and $f^0(h0)_\alpha$ are used, a potential energy $E^0_{cell}$ per unit cell $U^0$ and an $\alpha$ component $F^0(h0)_\alpha$ of the force acting on an atom (h0) can be calculated as follows:

$$E^0_{cell} = \frac{1}{2}\sum_h^{N^0} A^0(h0)e^0(h0) \qquad (86)$$

$$F^0(h0)_\alpha = A^0(h0)f^0(h0)_\alpha \qquad (87)$$

The processing operation of the periodic system $S^1$ calculation unit 4-6 shown in FIG. 14 will be described next. The periodic system $S^1$ calculation unit 4-6 calculates a potential energy $E^1_{cell}$ per unit cell $U^1$ of the periodic system $S^1$ and an a component $F^1(k0)_\alpha$ of the force acting on the atom (k0) as follows:

$$E^1_{cell} = \frac{1}{2}\sum_k^{N^1} A^1(k0)e^1(k0) \qquad (88)$$

$$F^{12}(k0)_\alpha = A^1(k0)f^1(k0)_\alpha \qquad (89)$$

where $e^1(k0)$ and $f^1(k0)_\alpha$ are given by the following equations, respectively:

$$e^1(k0) = \qquad (90)$$
$$e^0(k0) + \sum_{(k'\xi') \in R_{cut}} A^1(k'\xi') \times [\varphi(r^1 \mid k0, k'\xi') - \varphi(r^0 \mid k0, k'\xi')]$$

$$f^1(k0)_\alpha = \qquad (91)$$
$$f^0(k0)_\alpha + \sum_{(k'\xi') \in R_{cut}} A^1(k'\xi') \times [\varphi'(r^1 \mid k0, k'\xi')_\alpha - \varphi'(r^0 \mid k0, k'\xi')_\alpha]$$

$$\varphi'(r^n \mid k\xi, k'\xi')_\alpha \equiv -\frac{\partial \varphi(r^n \mid k\xi, k'\xi')}{\partial r^n(k\xi, k'\xi')_\alpha} \qquad (92)$$

$e^0(k0)$ of equation (90) and $f^0(k0)_\alpha$ of equation (91) are physical quantities of the reference system $S^0$. Equations (93) and (94) hold on the basis of the correspondence list [$S^0 \leftrightarrow S^1$] and the periodicity of the reference system $S^0$:

$$e^0(k0) = e^0(h\zeta) = e^0(h0) \qquad (93)$$

$$f^0(k0)_\alpha = f^0(h\zeta)_\alpha = f^0(h0)_\alpha \qquad (94)$$

These physical quantities are equivalent to $e^0(h0)$ and $f^0(h0)_\alpha$ calculated by the reference system $S^0$ calculation unit 4-5 on the basis of equations (83) and (84). In the above equations, $$\sum_{(k'\xi') \in R_{cut}}$$

means that sum is calculated for all atoms (k'ξ') contained in a region $R_{cut}$ centered on an atom (kξ). This region is given as a sphere having the radius $R_{cut}$. The region $R_{cut}$ may be designated by the user or appropriately set by the materials design system of the present invention.

As will be described later, when the region $R_{cut}$ is set considering the balance between the computational time and computational accuracy required by the user, efficient MD calculation for the periodic system $S^1$ can be realized. During the MD calculation, generally, the total energy (kinetic energy+potential energy) of the system is monitored to confirm the energy conservation law. In the calculation method of the present invention, the kinetic energy can be calculated as follows:

$$K^1_{cell} = \sum_k^{N^1} \frac{1}{2}m^1(k0)\sum_\alpha [v^1(k0)_\alpha]^2 \qquad (95)$$

Accordingly, the total energy per unit cell $U^1$ of the periodic system $S^1$ can be obtained as $K^1_{cell} + E^1_{cell}$.

The processing operation of the periodic system MD calculation unit 4-8 shown in FIG. 14 will be described next. In this embodiment, the Verlet method will be exemplified as the algorithm (difference method of Newton's equation) in MD calculation, and microcanonical ensemble (the number of particles, volume, and energy are constant) will be exemplified as an ensemble. However, other methods can also be applied. To perform MD calculation for the periodic system $S^1$, the periodic system MD calculation unit 4-8 calculates the position and velocity of each of the $N^1$ atoms (k0) contained in the fundamental cell (ξ=0) at a time t+Δt using equations (96) and (97):

$$r^1(k0 \mid t + \Delta t)_\alpha = r^1(k0 \mid t)_\alpha + \Delta t v^1(k0 \mid t)_\alpha + \frac{(\Delta t)^2}{2m^1(k0)} F^1(k0 \mid t)_\alpha \qquad (96)$$

$$v^1(k0 \mid t+\Delta t)_\alpha = v^1(k0 \mid t)_\alpha + \frac{\Delta t}{2m^1(k0)}[F^1(k0 \mid t)_\alpha + F^1(k0 \mid t+\Delta t)_\alpha] \quad (97)$$

where $F^1(k0|t)_\alpha$ is the $\alpha$ component of the force acting on the atom (k0) at a time t, which is calculated by the periodic system $S^1$ calculation unit 4-6 in accordance with equation (89), and $\Delta t$ is the time interval of MD calculation. The value $\Delta t$ may be arbitrarily designated by the user or set on the side of the materials design system of the present invention.

The periodic system MD calculation unit 4-8 repeatedly calculates the dynamic behavior of the structure of the periodic system $S^1$ until a time tend using equations (96) and (97). The end time tend is arbitrarily set by the user.

The processing operation in the block diagram (FIG. 14) showing the arrangement of the materials design system for executing MD calculation for the periodic system $S^1$ of the present invention has been described in units of blocks. Next, procedures of MD calculation for the periodic system $S^1$ will be described in detail with reference to flow charts.

Figure 20:
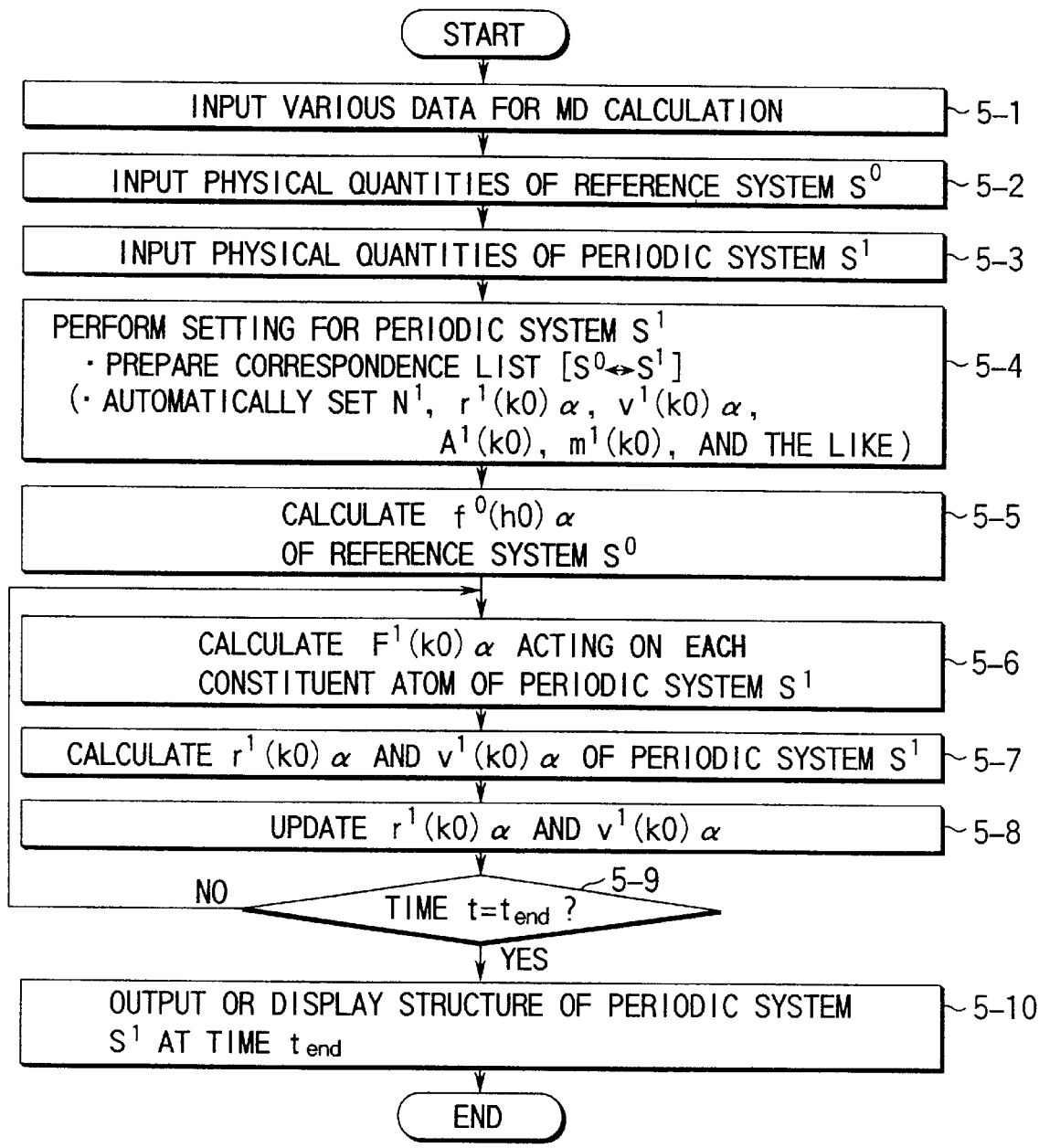
FIG. 20 is a flow chart for executing the MD calculation for the periodic system $S^1$ according to the fifth embodiment.

FIG. 20 shows the procedures of MD calculation for the periodic system $S^1$.

First, various data (temperature T, time interval $\Delta t$, end time $t_{end}$, region $R_{cut}$, and the like) for MD calculation are input (step 5-1). These values may be input after step 5-2 or 5-3 except values such as the temperature T associated with processing in the following step.

Physical quantities of the reference system $S^0$ are input to the reference system $S^0$ processing unit 4-1 (step 5-2). The physical quantities are the lattice constant of the reference system $S^0$, the number $N^0$ of atoms per unit cell $U^0$, the atomic coordinates $r^0(h0)_\alpha$ of the $N^0$ atoms, the potential parameters $A^0(h0)$, and the masses $m^0(h0)$.

Physical quantities of the periodic system $S^1$ are input to the periodic system $S^1$ processing unit 4-2 (step 5-3). These physical quantities are the lattice constants of the periodic system $S^1$, the number $N^1$ of atoms per unit cell $U^1$, the atomic coordinates $r^1(k0)_\alpha$ of the $N^1$ atoms, the velocities $v^1(k0)_\alpha$, the potential parameters $A^1(k0)$, and the masses $m^1(k0)$.

The periodic system $S^1$ processing unit 4-2 also prepares the correspondence list $[S^0 \leftrightarrow S^1]$ (step 5-4). As has already been described in the description of each block, for the physical quantities input to the periodic system $S^1$ processing unit 4-2, the values (initial values for coordinates and velocities) may be automatically set by the materials design system of the present invention on the basis of the physical quantities of the reference system $S^0$ and the temperature T.

The reference system $S^0$ calculation unit 4-5 calculates $f^0(h0)_\alpha$ (step 5-5).

The above-described processing corresponds to initial setting for MD calculation. The following steps correspond to the processing operation of repetitive calculation in the MD calculation. Each step of repetitive calculation corresponds to the time t of MD calculation. For example, the initial time is set as t=0.

First, the periodic system $S^1$ calculation unit 4-6 calculates $F^1(k0)_\alpha$ (step 5-6). Next, the periodic system MD calculation unit 4-8 calculates $r^1(k0)_\alpha$ and $v^1(k0)_\alpha$ using $F^1(k0)_\alpha$ (step 5-7). Accordingly, the periodic system $S^1$ processing unit 4-2 updates the values $r^1(k0)_\alpha$ and $v^1(k0)_\alpha$ (step 5-8). Processing from step 5-6 to step 5-8 is repeatedly executed until it is determined in step 5-9 that the time t reaches the time $t_{end}$. Finally, at the time $t_{end}$, the structure of the periodic system $S^1$ is output or displayed (step 5-10).

In the MD calculation of the present invention, the values $r^1(k0)_\alpha$ and $v^1(k0)_\alpha$ and the physical quantities calculated using these values can be output or displayed at an arbitrary time during repetitive calculation. In step 5-6, the potential energy $E^1_{cell}$ and the kinetic energy $K^1_{cell}$ can be calculated/output at an arbitrary time of user's choice. However, when the potential energy is to be calculated, $e^0(h0)$ must be calculated in step 5-5 in advance.

A supplementary explanation about the flow chart (FIG. 20) of MD calculation for the periodic system $S^1$ will be made.

In FIG. 20, processing from step 5-6 to step 5-8 is simply represented as the processing operations of the periodic system $S^1$ calculation unit 4-6, the periodic system MD calculation unit 4-8, and the periodic system $S^1$ processing unit 4-2. When the Verlet algorithm is to be used, forces at the time t and a time $t+\Delta t$ must be calculated to obtain the velocity at the time $t+\Delta t$ in accordance with equation (97).

Figure 21:
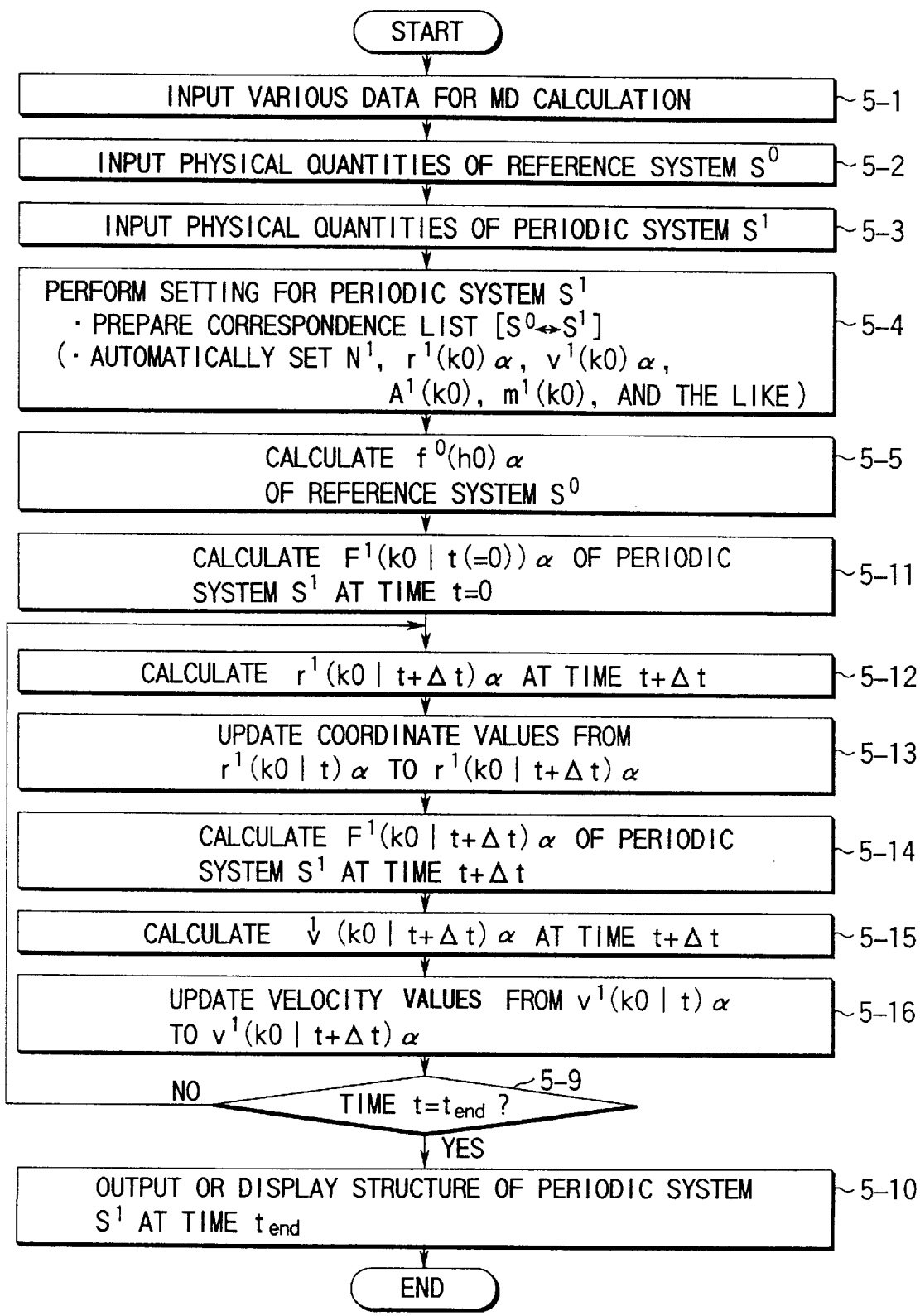
FIG. 21 is a flow chart showing a modification of the MD calculation for the periodic system $S^1$ according to the fifth embodiment.

When the Verlet algorithm is to be used, the flow chart in FIG. 20 is partially changed as shown in FIG. 21. In FIG. 21, step 5-11 is added. In step 5-11, the periodic system $S^1$ calculation unit 4-6 calculates the force $F^1(k0|t(=0))_\alpha$ at the time t=0 (initial time is set as 0). Accordingly, processing from step 5-6 to 5-8 is replaced with the following processing in FIG. 21.

The periodic system MD calculation unit 4-8 calculates coordinates $r^1(k0|t+\Delta t)_\alpha$ at the time $t+\Delta t$ using equation (96) (step 5-12). Accordingly, the periodic system $S^1$ processing unit 4-2 updates the coordinate values $r^1(k0|t)_\alpha$ to $r^1(k0|t+\Delta t)_\alpha$ (step 5-13).

The force $F^1(k0|t+\Delta t)_\alpha$ at the time $t+\Delta t$ is calculated using the updated coordinate values $r^1(k0|t+\Delta t)_\alpha$ (step 5-14). Using the value $F^1(k0|t+\Delta t)_\alpha$ and the value $F^1(k0|t)_\alpha$ which has already been calculated in step 5-14 of the preceding repetitive calculation cycle (step 5-11 when t=0), the periodic system MD calculation unit 4-8 calculates velocities $v^1(k0|t+\Delta t)_\alpha$ at the time $t+\Delta t$ using equation (97) (step 5-15). Accordingly, the periodic system $S^1$ processing unit 4-2 updates the velocity values $v^1(k0|t)_\alpha$ to $v^1(k0|t+\Delta t)_\alpha$ (step 5-16). The procedures from step 5-11 to step 5-16 change depending on the algorithm (e.g., Verlet method) to be used. According to the materials design system of the present invention, the flow chart can be appropriately changed depending on the algorithm to be employed.

Sixth Embodiment

MD calculation for Aperiodic System

In the sixth embodiment, a materials design system for executing MD calculation for an aperiodic system $S^2$ will be described.

This embodiment corresponds to the invention described in claim 2.

Figure 15:
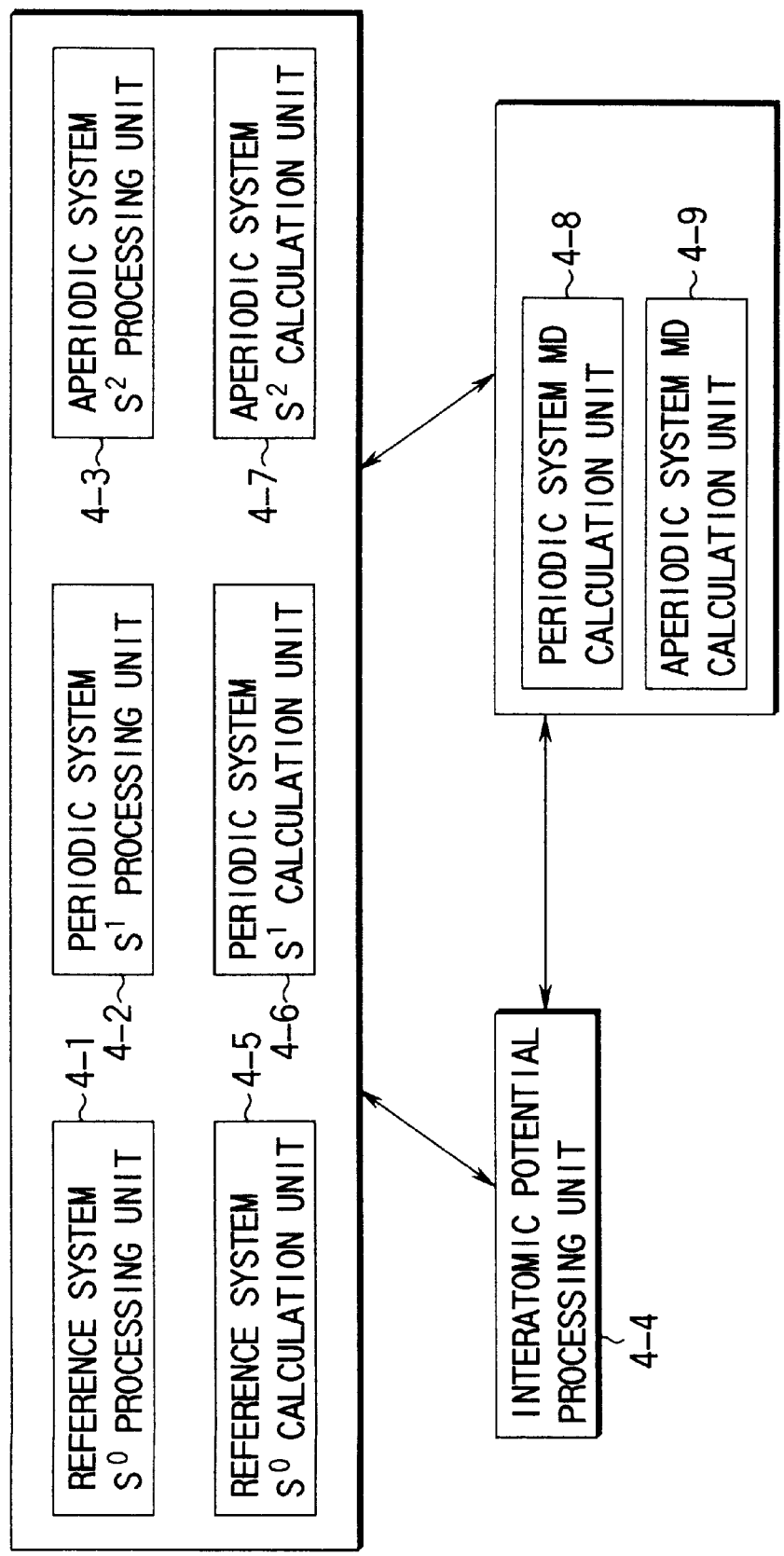
FIG. 15 is a block diagram showing the arrangement of a materials design system for executing MD calculation for an aperiodic system $S^2$ according to the sixth embodiment.

FIG. 15 is a block diagram showing the arrangement of the materials design system for executing MD calculation for the aperiodic system $S^2$. The materials design system comprises a reference system $S^0$ processing unit 4-1, a periodic system $S^1$ processing unit 4-2, an aperiodic system $S^2$ processing unit 4-3, an interatomic potential processing unit 4-4, a reference system $S^0$ calculation unit 4-5, a periodic system $S^1$ calculation unit 4-6, an aperiodic system $S^2$ calculation unit 4-7, a periodic system MD calculation unit 4-8, and an aperiodic system MD calculation unit 4-9.

In FIG. 15, the aperiodic system $S^2$ processing unit 4-3, the aperiodic system $S^2$ calculation unit 4-7, and the aperiodic system MD calculation unit 4-9 are added to the arrangement shown in FIG. 14. The reference system $S^0$ processing unit 4-1, the periodic system $S^1$ processing unit 4-2, the interatomic potential processing unit 4-4, the reference system $S^0$ calculation unit 4-5, the periodic system $S^1$ calculation unit 4-6, and the periodic system MD calculation unit 4-8 are the same as those shown in FIG. 14. The aperiodic system $S^2$ processing unit 4-3, the aperiodic system $S^2$ calculation unit 4-7, and the aperiodic system MD calculation unit 4-9 will be described, and thereafter, the procedures of MD calculation for the aperiodic system $S^2$ will be described with reference to a flow chart.

The processing operation of the aperiodic system $S^2$ processing unit 4-3 shown in FIG. 15 will be described first. The aperiodic system $S^2$ processing unit 4-3 holds/processes the crystal structure and the potential parameters of the aperiodic system $S^2$. In this embodiment, the structure of the aperiodic system $S^2$ is described on the basis of a deviation from a periodic system $S^1$.

This deviation occurs when the structure is modified in a certain region centered on a local disorder (e.g., impurity). In this embodiment, a system containing a local impurity will be exemplified as the aperiodic system $S^2$.

For the description based on such a deviation, the atoms of the periodic system $S^1$ are made to correspond to those of the aperiodic system $S^2$ in one-to-one correspondence using a correspondence list $[S^1 \leftrightarrow S^2]$. In the aperiodic system $S^2$, the periodicity of the periodic system $S^1$ disappears because of the local arrangement of the impurity. For this reason, the notation using atomic numbers (k$\xi$) representing the periodicity is not appropriate, and serial numbers (i) are set for the atoms of the aperiodic system $S^2$. This processing can be performed using, e.g., a relation $i=k+\xi N^1$. This information is stored in the correspondence list $[S^1 \leftrightarrow S^2]$.

Figure 17:
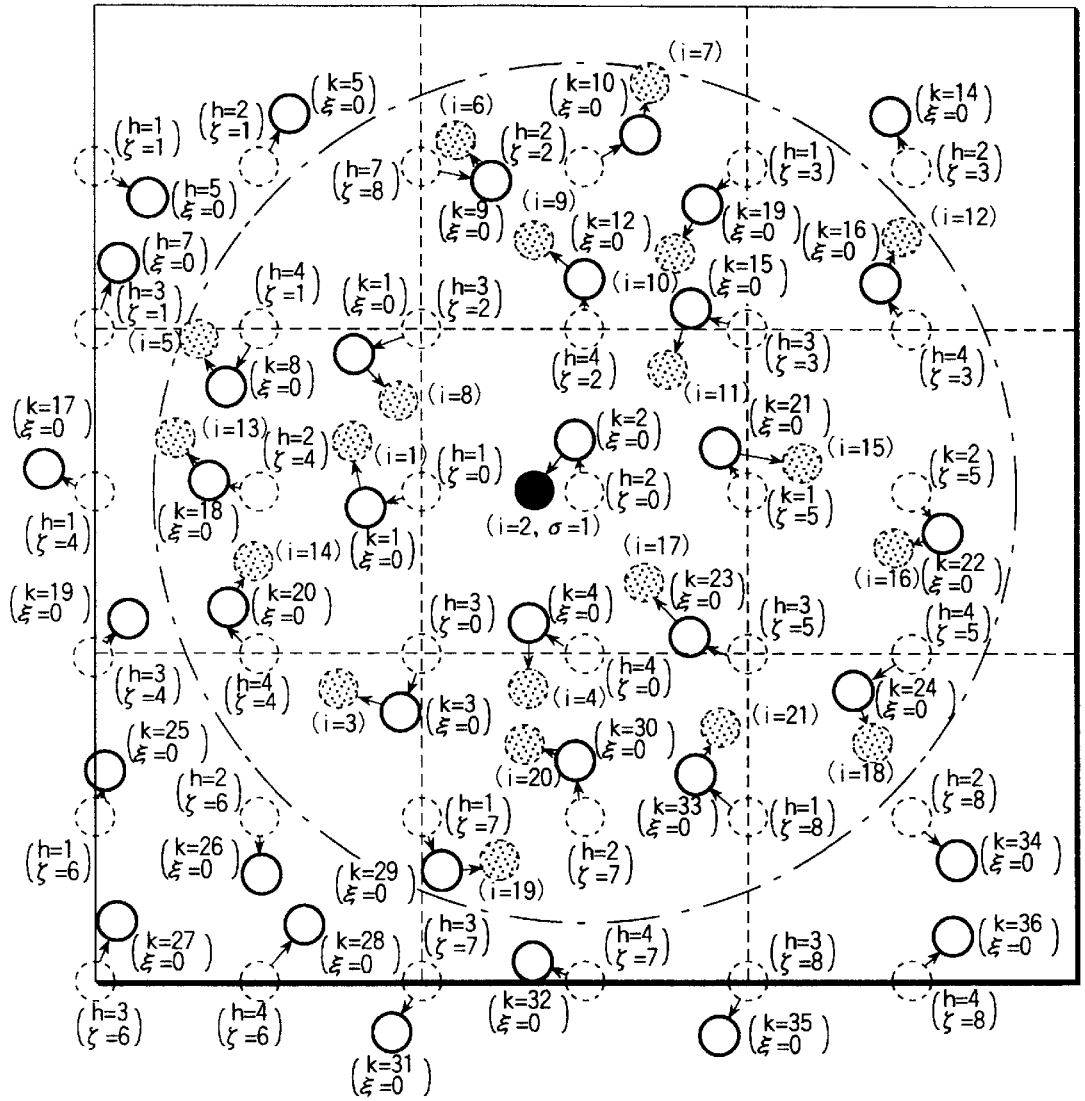
FIG. 17 is a view for explaining the relationship among the reference system $S^0$, the periodic system $S^1$, and the aperiodic system $S^2$.

FIG. 17 shows an example of the correspondence among a reference system $S^0$ (constituent atoms and unit cells are indicated by dashed lines), the periodic system $S^1$ (constituent atoms and unit cells are indicated by solid lines), and the aperiodic system $S^2$ (constituent atoms are indicated by gray bullets, and a region $R_{relax}$ to be described later is indicated by a chain line).

The reference system $S^0$ and the periodic system $S^1$ shown in FIG. 17 are the same as those shown in FIG. 16. The aperiodic system $S^2$ shown in FIG. 17 corresponds to the periodic system $S^1$ in FIG. 16 to which one substitutional impurity atom (indicated by a closed circle) is introduced. More specifically, for the atom ic arrangement of the aperiodic system $S^2$, atoms in the region $R_{relax}$ are indicated by gray bullets (the impurity atom is indicated by the closed circle), and atoms outside the region $R_{relax}$ are indicated by hollow bullets (open circles).

As the correspondence list $[S^1 \leftrightarrow S^2]$ for FIG. 17, FIG. 18 shows an example in which the serial numbers (i) of 21 constituent atoms of the aperiodic system $S^2$ are registered. The 21 atoms correspond to atoms contained in the region $R_{relax}$ represented by the chain line in FIG. 17. In the correspondence list $[S^1 \leftrightarrow S^2]$ shown in FIG. 18, to clarify the relationship between the correspondence lists $[S^0 \leftrightarrow S^1]$ and $[S^1 \leftrightarrow S^2]$, atoms (e.g., (k=5,$\xi$=0) and (k=6,$\xi$=0)) of the periodic system $S^1$, which do not correspond to the atoms of the aperiodic system $S^2$, are also listed. These atoms need not always be registered in the correspondence list $[S^1 \leftrightarrow S^2]$.

In the example shown in FIG. 17, the region $R_{relax}$ is smaller than the unit cell $U^1$ of the periodic system $S^1$. Even when the region $R_{relax}$ is larger than the unit cell $U^1$, the same handling as described above can be performed. For the descriptive convenience, the impurity atom in the aperiodic system $S^2$ is also represented by an impurity number ($\sigma$).

The flow of the processing operation of the aperiodic system $S^2$ processing unit 4-3 will be described in associated with the initial setting stage of MD calculation. The aperiodic system $S^2$ processing unit 4-3 receives the number $N^{imp}$ of impurity atoms, the impurity atom Nos., potential parameters $A^{imp}(\sigma)$ and masses $m^{imp}(\sigma)$, and the region $R_{relax}$ where lattice relaxation is taken into consideration.

The impurity atom No. is the number of each atom of the periodic system $S^1$, which is substituted with an impurity atom. More specifically, when $N^{imp}$ impurity atoms are to be generated, a set $\{(k_1,\xi_1), (k_2,\xi_2), \ldots, (k_{Nimp},\xi_{Nimp})\}$ is designated.

The example shown in FIG. 17 includes one impurity atom ($N^{imp}$=1), so only an atom $\{(k=2,\xi=0)\}$ is designated. As the number $N^{imp}$, an arbitrary number of impurity atoms can be handled. The impurity atoms to be designated may be contained in the fundamental cell ($\zeta$=0) of the periodic system $S^1$ or contained in a peripheral unit cells ($\xi \neq 0$). In addition, the set $\{(k_1,\xi_1), (k_2,\xi_2), \ldots, (k_{Nimp},\xi_{Nimp})\}$ for designating the impurity atoms is made to correspond to a set of impurity numbers $\{(\sigma 1), (\sigma 2), \ldots, (\sigma_{Nimp})\}$ in accordance with the correspondence list $[S^1 \leftrightarrow S^2]$.

The correspondence list $[S^1 \leftrightarrow S^2]$ shown in FIG. 18 contains one impurity atom, and an impurity number ($\sigma$=1) is assigned to an atom (i=2) of the aperiodic system $S^2$ The region $R_{relax}$ where lattice relaxation is taken into consideration will be described next. In the aperiodic system $S^2$, lattice relaxation takes place around impurity atoms. Since the relaxation amount of each atom becomes almost 0 at a position far from the impurity atoms, lattice relaxation may be calculated only in a finite region centered on the impurity atoms. As the region where lattice relaxation is taken into consideration, a sphere having a radius $R_{relax}$ centered on the center of gravity of the impurity atoms can be assumed. This region need not always be spherical, and in this embodiment, the region where lattice relaxation is taken into consideration is generally represented by $R_{relax}$. The region $R_{relax}$ may be arbitrarily designated by the user or appropriately set by the materials design system of the present invention.

The aperiodic system $S^2$ processing unit 4-3 counts the number $N^2$ of atoms contained in the region $R_{relax}$ ($N^2$ does not mean the square of N. In this specification, the square of N is represented by N×N to prevent confusion) and always $N^2 > N^{imp}$. In the example shown in FIG. 17, $N^2$=21. By way of a supplementary explanation, the number of atoms, which is necessary when the same system as the aperiodic system $S^2$ is to be handled by the supercell method, corresponds to the above-mentioned Nsc. Generally Nsc>$N^2$, because, in the supercell method, a region such as a buffer layer must be set around the region $R_{relax}$ to reduce the interaction between disorders.

The computational amount of the calculation method of the present invention for the aperiodic system is smaller than that of the supercell method. Next, the aperiodic system $S^2$ processing unit 4-3 sets the initial values of coordinates $r^2(i)_\alpha$ and velocities $v^2(i)_\alpha$ from the correspondence list $[S^1 \leftrightarrow S^2]$ and the periodicity of the periodic system $S^1$ on the basis of equations (98) and (99):

$$r^2(i)_\alpha = r^1(k\xi)_\alpha r^1(k0)_\alpha + r^1(\xi)_\alpha \qquad (98)$$

$$v^2(i)_\alpha = v^1(k\xi)_\alpha v^1(k0)_\alpha \qquad (99)$$

The initial values need not always be set using equations (98) and (99) and may be appropriately set by the user. Handling of the potential parameters and masses of the aperiodic system $S^2$ will be described next. As described above, the aperiodic system $S^2$ processing unit 4-3 receives the potential parameters $A^{imp}(\sigma)$ and the masses $m^{imp}(\sigma)$ of the $N^{imp}$ impurity atoms ($\sigma$). Accordingly, the aperiodic system $S^2$ processing unit 4-3 sets potential parameters $A^2(i)$ and masses $m^2(i)$ of the $N^2$ atoms (i) contained in the region $R_{relax}$ as follows:

$$\left.\begin{array}{l} A^2(i) = A^1(i)( = A^1(k\xi) = A^1(k0)) \\ m^2(i) = m^1(i)( = m^1(k\xi) = m^1(k0)) \end{array}\right\} i \neq \sigma \quad (100)$$

$$\left.\begin{array}{l} A^2(i) = A^{imp}(\sigma)( \neq A^1(k\xi)) \\ m^2(i) = m^{imp}(\sigma)( \neq m^1(k\xi)) \end{array}\right\} i \neq \sigma \quad (101)$$

As described above about the periodic system $S^1$ processing unit 4-2, each atom of the periodic system $S^1$ has the same potential parameter as that of the atom of the reference system $S^0$, which are made to correspond to each other on the basis of the correspondence list $[S^0 \leftrightarrow S^1]$ (equation (77)). For the aperiodic system $S^2$, however, the impurity atom ($\sigma$) has a potential parameter different from that of the corresponding atom of the periodic system $S^1$. (equation (101)).

The materials design system can handle three types of impurities, i.e., a substitutional impurity atom, an interstitial impurity atom, and a defect. These impurity atoms are designated on the basis of the relationship in the potential parameters between the periodic system $S^1$ and the aperiodic system $S^2$, as shown in FIG. 19. FIG. 19 shows rules associated with handling of a mass m together with a potential parameter A. Handling of the mass m is the same as that of the potential parameter A (see the description of the reference system $S^0$ processing unit 4-1, the periodic system $S^1$ processing unit 4-2, and the aperiodic system $S^2$ processing unit 4-3). The mass m can be regarded as one of the potential parameters A.

Of the three impurity atoms shown in FIG. 19, the interstitial impurity atom must be particularly carefully handled. An atom corresponding to the interstitial impurity atom is not originally present in the reference system $S^1$. To make the one-to-one correspondence based on the correspondence list $[S_1 \leftrightarrow S^2]$, a dummy atom must be set in the periodic system $S^1$ (and the reference system $S^0$) in advance. Since the potential parameter $A^1$ (and $A^0$) of the dummy atom is set to be 0, the energy or force acting on each atom in the periodic system $S^1$ (and the reference system $S^0$) does not undesirably change even when the dummy atom is taken into consideration.

The processing operation of the aperiodic system $S^2$ calculation unit 4-7 shown in FIG. 15 will be described next. The aperiodic system $S^2$ calculation unit 4-7 calculates $\Delta E^2$ as for the potential energy of the aperiodic system $S^2$ and an $\alpha$ component $F^2(i)_\alpha$ of the force acting on the atom (i) using equations (102) and (103) below:

$$\Delta E^2 = \Delta E^{2(a)} + \Delta E^{2(b)} \quad (102)$$

$$F^2(i)_\alpha = \frac{m^2(i)}{m^1(i)} F^1(i)_\alpha + F^{2(a)}(i)_\alpha + \Delta F^{2(b)}(i)_\alpha \quad (103)$$

where $F^1(i)_\alpha$ is the force in the periodic system $S^1$. Equation (104) holds on the basis of the correspondence list $[S^1 \leftrightarrow S^2]$ and the periodicity of the periodic system $S^1$:

$$F^1(i)_\alpha = F^1(k\xi)_\alpha = F^1(k0)_\alpha \quad (104)$$

The value $F^1(i)_\alpha$ corresponds to $F^1(k0)_\alpha$ calculated by the periodic system $S^1$ calculation unit 4-6 using equation (89). For the energy, $\Delta E^{2(a)}$ and $\Delta E^{2(b)}$ are described as follows:

$$\Delta E^{2(a)} = \sum_{i=\sigma}^{N_{imp}} [A^2(i) - A^1(i)]e^1(i) + \quad (105)$$

$$\sum_{i=\sigma}^{N_{imp}} [A^2(i) - A^1(i)] \sum_{j(>i)=\sigma}^{N_{imp}} [A^2(j) - A^1(j)]\varphi(r^1 \mid i, j)$$

$$\Delta E^{2(b)} = \sum_{i \in R_{relax}}^{N^2} A^2(i) \sum_{j(>i)}^{all} A^2(j)[\varphi(r^2 \mid i, j) - \varphi(r^1 \mid i, j)] \quad (106)$$

For the force, $\Delta F^{(a)}(i)_\alpha$ and $\Delta F^{2(b)}(i)_\alpha$ are described as follows:

$$\Delta F^{2(b)}(i)_\alpha = \left[A^2(i) - \frac{m^2(i)}{m^1(i)} A^1(i)\right] f^1(i)_\alpha + \quad (107)$$

$$A^2(i) \sum_{j=\sigma}^{N_{imp}} [A^2(j) - A^1(j)] \varphi'(r^1 \mid i, j)_\alpha$$

$$\Delta F^{2(b)}(i)_\alpha = A^2(i) \sum_{j}^{all} A^2(j)[\varphi'(r^2 \mid i, j)_\alpha - \varphi'(r^1 \mid i, j)_\alpha] \quad (108)$$

$$\varphi'(r^n \mid i, j)_\alpha \equiv -\frac{\partial \varphi(r^n \mid i, j)}{\partial r^n(i, j)_\alpha} \quad (109)$$

where $e^1(i)$ of equation (105) and $f^1(i)_\alpha$ of equation (107) are physical quantities of the periodic system $S^1$. Equations (110) and (111) hold on the basis of the correspondence list $[S^1 \leftrightarrow S^2]$ and the periodicity of the periodic system $S^1$:

$$e^1(i) = e^1(k\xi) = e^1(k0) \quad (110)$$

$$f^1(i)_\alpha = f^1(k\xi)_\alpha = f^1(k0)_\alpha \quad (111)$$

These values correspond to $e^1(k0)$ and $f^1(k0)_\alpha$ calculated by the periodic system $S^1$ calculation unit 4-6 on the basis of equations (90) and (91), respectively. In the above equations, $$\sum_{i=\sigma}^{N^{imp}}$$

represents the sum for the $N^{imp}$ impurity atoms ($\sigma$).

$$\sum_{i \in R_{relax}}^{N^2}$$

means the sum for the $N^2$ atoms contained in the region $R_{relax}$.

A supplementary explanation about $\Delta E^2$ will be made below. $\Delta E^2$ is a physical quantity defined by equation (112) below:

$$\Delta E^2 = E^2_{whole} - E^1_{whole} \quad (112)$$

where $E^1_{whole}$ and $E^2_{whole}$ represent potential energies of the whole periodic system $S^1$ and the whole aperiodic system $S^2$, respectively. More specifically, $\Delta E^2$ corresponds to a change in energy which is caused by the local arrangement of the impurity in the periodic system $S^1$. Since the aperiodic system $S^2$ has no periodical unit (unit cell), a quantity such as $E^0_{cell}$ of the reference system $S^0$, or $E^1_{cell}$ of the periodic system $S^1$ cannot be defined. In this embodiment, the energy of the aperiodic system $S^2$ is described using the potential energy change amount $\Delta E^2$ from the periodic system $S^1$. In addition, the kinetic energy change amount $\Delta E^2$ is calculated as follows:

$$\Delta K^2 = \sum_i^{N^2} \frac{1}{2}\left[m^2(i)\sum_\alpha [v^2(i)_\alpha]^2 - m^1(i)\sum_\alpha [v^1(i)_\alpha]^2\right] \qquad (113)$$

With this calculation, the total energy of the aperiodic system $S^2$ can be obtained as a change amount $\Delta K^2 + \Delta E^2$ from the periodic system $S^1$. A supplementary explanation about a method of calculating equations (106) and (108) will be made.

$$\sum_j^{all}$$

of equations (106) and (108) means that the sum is calculated for terms as many as possible until the convergence of the sum attains a sufficient accuracy. A region $R'_{cut}$ centered on the atom (i) may be assumed, and the sum $$\sum_j^{all}$$

may be calculated only for atoms (j) contained in the region $R'_{cut}$, and in many case, $$\sum_j^{all}$$

is rewritten by $$\sum_{j \in R'_{cut}} \cdot$$

In calculation of $$\sum_j^{all}$$

(or $$\sum_{j \in R'_{cut}} )$$

of equations (106) and (108), interactions with the atoms (j) outside the region $R_{relax}$ must also be calculated. Assume that the regions $R_{relax}$ and $R'_{cut}$ are given as spheres having radii $R_{relax}$ and $R'_{cut}$, respectively, and that the region $R'_{relax}$ is given by a sphere having the radium $R'_{relax}$ ($=R_{relax}+R'_{cut}$). To increase the efficiency of calculation, the correspondence list [$S^1 \leftrightarrow S^2$] is prepared for the $N^2$, for the $N^{2'}$ atoms which are contained in the region $R'_{relax}$, where $N^{2'} > N^2$.

The processing operation of the aperiodic system MD calculation unit 4-9 shown in FIG. 15 will be described below. In the sixth embodiment, the Verlet method will be exemplified as the algorithm (difference method of Newton's equation) of MD calculation, and microcanonical ensemble (the number of particles, volume, and energy are constant) will be exemplified as an ensemble, as in the fifth embodiment. Other methods can also be applied. To perform MD calculation for the aperiodic system $S^2$, the aperiodic system MD calculation unit 4-9 calculates the position and velocity of each of the $N^2$ atoms (i) contained in the region $R_{relax}$ at a time $t+\Delta t$ using equations (114) and (115):

$$r^2(i \mid t+\Delta t)_\alpha = r^2(i \mid t)_\alpha + \Delta t v^2(i \mid t)_\alpha + \frac{(\Delta t)^2}{2m^2(i)} F^2(i \mid t)_\alpha \qquad (114)$$

$$v^2(i \mid t+\Delta t)_\alpha = v^2(i \mid t)_\alpha + \frac{\Delta t}{2m^2(i)}[F^2(i \mid t)_\alpha + F^2(i \mid t+\Delta t)_\alpha] \qquad (115)$$

As in handling by the periodic system MD calculation unit 4-8, $\Delta t$ is the time interval of MD calculation, and $F^2(i|t)_\alpha$ is the $\alpha$ component of the force acting on the atom (i) at a time t, which is calculated by the aperiodic system $S^2$ calculation unit 4-7 using equation (103). When MD calculation for the aperiodic system $S^2$ is to be performed by the materials design system of the present invention, the aperiodic system MD calculation unit 4-9 calculates the change over time in the structure of the aperiodic system $S^2$ using equations (114) and (115), and simultaneously, the periodic system MD calculation unit 4-8 executes MD calculation for the periodic system $S^1$. The procedures of this processing will be described below with reference to flow charts.

Figure 22:
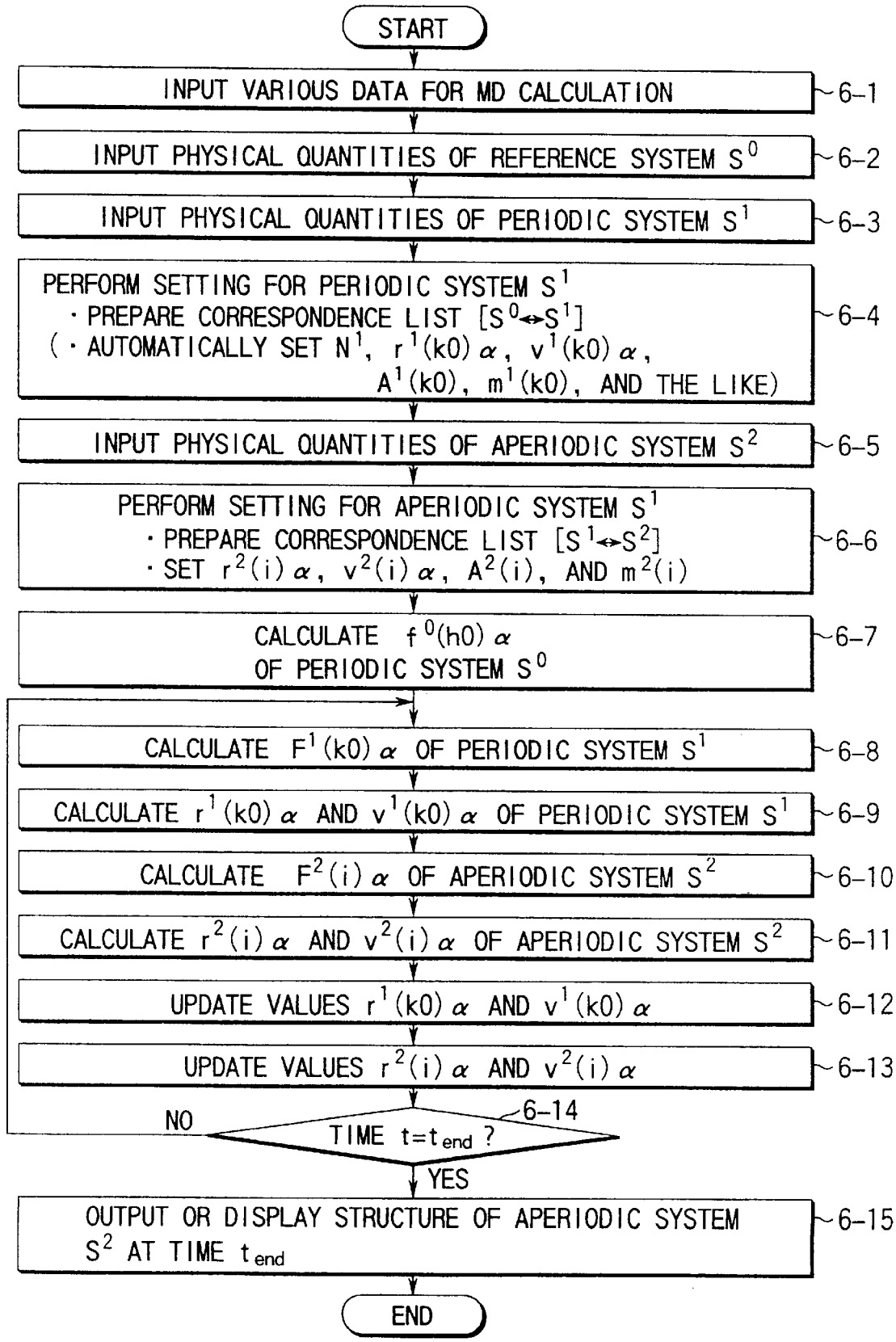
FIG. 22 is a flow chart for executing the MD calculation for the periodic system $S^2$ according to the sixth embodiment.

FIG. 22 shows the procedures of MD calculation for the aperiodic system $S^2$. From step 6-1 to step 6-4, the same processing as that from step 5-1 to step 5-4 in FIG. 20 described above is performed. Next, the physical quantities of the aperiodic system $S^2$ are input to the aperiodic system $S^2$ processing unit 4-3 (step 6-5). The physical quantities are the number $N^{imp}$ of impurity atoms contained in the aperiodic system $S^2$, the numbers of the $N^{imp}$ impurity atoms ($\sigma$), the potential parameter $A^{imp}(\sigma)$ and the mass $m^{imp}(\sigma)$ of each impurity atom ($\sigma$), and the region $R_{relax}$ where lattice relaxation is taken into consideration. Upon receiving the physical quantities, the aperiodic system $S^2$ processing unit 4-3 prepares the correspondence list [$S^1 \leftrightarrow S^2$] and sets the initial values of the coordinates $r^2(i)_\alpha$ and velocities $v^2(i)_\alpha$ and the values of the potential parameter $A^2(i)$ and the mass $m^2(i)$ of each of the $N^2$ atoms contained in the region $R_{relax}$ of the aperiodic system $S^2$ (step 6-6). Next, the reference system $S^0$ calculation unit 4-5 calculates $f^0(h0)_\alpha$ (step 6-7). The above processing corresponds to initial setting for MD calculation, and the following steps correspond to the processing operation of repetitive calculation according to the MD calculation. First, the periodic system $S^1$ calculation unit 4-6 calculates $F^1(k0)_\alpha$ (step 6-8). The periodic system MD calculation unit 4-8 calculates $r^1(k0)_\alpha$ and $v^1(k0)_\alpha$ using $F^1(k0)_\alpha$ (step 6-9). Next, the aperiodic system $S^2$ calculation unit 4-7 calculates $F^2(i)_\alpha$ (step 6-10). The aperiodic system MD calculation unit 4-9 calculates $r^2(i)_\alpha$ and $v^2(i)_\alpha$ using $F^2(i)_\alpha$ (step 6-11). The periodic system $S^1$ processing unit 4-2 updates the values $r^1(i)_\alpha$ and $v^1(i)_\alpha$ (step 6-12), and the aperiodic system $S^2$ processing unit 4-3 updates the values $r^2(i)_\alpha$ and $v^2(i)_\alpha$ (step 6-13). Processing from step 6-8 to step 6-13 is repeatedly executed until it is determined in step 6-14 that the time t reaches the time tend. Finally, at the time tend, the structure of the aperiodic system $S^2$ is output or displayed (step 6-15). In the MD calculation of the present invention, the values $r^2(k0)_\alpha$ and $v^2(k0)_\alpha$ and the physical quantities calculated using these values can be output or displayed at an arbitrary time during repetitive calculation. In step 6-10, the potential energy $\Delta E^2$ and the kinetic energy $\Delta K^2$ can be calculated/output at an arbitrary time of user's choice. However, when the potential energy is to be calculated, $e^0(h0)$ is calculated in step 6-7, and $e^1(k0)$ is calculated in step 6-8 in advance. As described above, when MD calculation for the aperiodic system $S^2$ is to be performed by the materials design system of the present invention, MD calculation for the periodic system $S^1$ is also simultaneously executed. Therefore, for the periodic system $S^1$ as well, the values $r^1(k0)_\alpha$ and $v^1(k0)_\alpha$ and physical quantities calculated using these values can be output or displayed at an arbitrary time, the values $E^1_{cell}$ and $K^1_{cell}$ can be calculated/output at an arbitrary time (step 6-8), and the final structure of the periodic system $S^1$ at the time tend can be output or displayed (step 6-15). The flow chart shown in FIG. 22 can be changed, like the change from FIG. 20 to FIG. 21, in accordance with the algorithm to be used (e.g., Berle's method). In the materials design system of the present invention, for the aperiodic system $S^2$ as well, MD calculation according to the algorithm to be used can be appropriately executed.

Seventh Embodiment

A modification of the materials design systems of the fifth and sixth embodiments will be described below as the seventh embodiment.

Handling of interatomic interactions other than the function given by equation (79) will be described first.

The $r^{-n}$ functions (particularly, Coulomb interaction) described by equation (79) are long-range interactions and therefore have serious problems such as an increase in computational time and a computational error caused by application of the supercell method. The materials design system of the present invention is to solve these problems.

As interatomic interactions which are not described by equation (79), there are a Born-Mayer type interaction (exponential function) representing a short-range repulsive force, Valence-Force Field model (many-body force) representing a covalent bond, and the like. These interatomic interactions are generally short-range interactions.

Since these short-range interactions have no problems such as an increase in computational time and a computational error, the energies or forces of a reference system $S^0$, a periodic system $S^1$, and an aperiodic system $S^2$ can be calculated by a general method without any problems. When the energy and force for the short-range interaction, which are calculated by the conventional method, are added to the energy and force for a long-range interaction, which are calculated by the calculation method of the present invention, MD calculation using a general interatomic interaction can be executed.

When MD calculation for the aperiodic system $S^2$ is to be performed by the materials design system of the sixth embodiment, MD calculation for the periodic system $S^1$ is simultaneously performed, as described above. When MD calculation for the aperiodic system $S^2$ is to be actually performed for the purpose of materials design or the like, it is expected that the MD calculation must be executed a number to times while changing the number or types of impurity atoms in the same parent material (periodic system $S^1$). In such a case, the same calculation is wastefully repeated a number of times for the periodic system $S^1$. To solve this problem, in the materials design system of the present invention, MD calculation for the periodic system $S^1$ is executed only once to prepare a data base associated with the physical quantities (position, velocity, and force of each atom) of the periodic system $S^1$ at each time. MD calculation for the aperiodic system $S^2$ can also be efficiently executed by using the database. The database is prepared in units of simulation conditions including the type of the periodic system $S^1$, the temperature, and the like.

When MD calculation for the aperiodic system $S^2$ is to be performed on the basis of the first embodiment, the data base is prepared in units of simulation conditions including the type of the reference system $S^0$, the temperature, and the like, thereby increasing the efficiency.

A supplementary explanation about the coordinates and velocities of the periodic system $S^1$ and the aperiodic system $S^2$ will be made. As the basic concept of the materials design system of the present invention, the periodic system $S^1$ is described by the deviation from the reference system $S^0$, and the aperiodic system $S^2$ is described by the deviation from the periodic system $S^1$. Therefore, as for the periodic system $S^1$:

$$r^1(k0)_\alpha = r^0(k0)_\alpha + \Delta r^1(k0)_\alpha \tag{116}$$

$$v^1(k0)_\alpha = v^0(k0)_\alpha + \Delta v^1(k0)_\alpha \tag{117}$$

As for the aperiodic system $S^2$:

$$\begin{aligned} r^2(i)_\alpha &= r^1(i)_\alpha + \Delta r^2(i)_\alpha \\ &= r^0(i)_\alpha + \Delta r^1(i)_\alpha + \Delta r^2(i)_\alpha \end{aligned} \tag{118}$$

$$\begin{aligned} v^2(i)_\alpha &= v^1(i)_\alpha + \Delta v^2(i)_\alpha \\ &= v^0(i)_\alpha + \Delta v^1(i)_\alpha + \Delta v^2(i)_\alpha, \end{aligned} \tag{119}$$

where $\Delta r^1(k0)_\alpha$ and $\Delta v^1(k0)_\alpha$ correspond to deviations from the reference system $S^0$ caused by microscopic vibration (lattice vibration) resulting from the temperature effect, and $\Delta r^2(i)_\alpha$ and $\Delta v^2(i)_\alpha$ correspond to deviations from the periodic system $S^1$ caused by the presence of the local impurity. In the fifth and sixth embodiments, $r^1(k0)_\alpha$, $v^1(k0)_\alpha$, $r^2(i)_\alpha$, and $v^2(i)_\alpha$ are directly handled. However, $\Delta r^1(k0)_\alpha$, $\Delta v^1(k0)_\alpha$, $\Delta r^2(i)_\alpha$, and $\Delta v^2(i)_\alpha$ may be calculated first, and then, $r^1(k0)_\alpha$, $v^1(k0)_\alpha$, $r^2(i)_\alpha$, and $v^2(i)_\alpha$ may be obtained using equations (116) to (119). In this case, as the forces of the periodic system $S^1$ and the aperiodic system $S^2$, instead of $F^1(k0)_\alpha$ (equation (89)) and $F^2(i)_\alpha$ (equation (103)), equations (120) and (121) below are calculated:

$$\Delta F^1(k0)_\alpha = F^1(k0)_\alpha - F^0(k0)_\alpha \tag{120}$$

$$\Delta F^2(i)_\alpha = F^2(i)_\alpha - F^1(i)_\alpha \tag{121}$$

The periodic system $S^1$ calculation unit 4-6 performs repetitive calculation while replacing $r^1$, $v^1$, and $F^1$ of equations (96) and (97) with $\Delta r^1$, $\Delta v^1$, $\Delta F^1$. The aperiodic system $S^2$ calculation unit 4-7 performs repetitive calculation while replacing $r^2$, $v^2$, and $F^2$ of equations (115) and (114) with $\Delta r^2$, $\Delta v^2$, and $\Delta F^2$. In equations (117) and (119), $v^0$ represents the velocity of each atom of the reference system $S^0$. Since the reference system $S^0$ is a system at the absolute zero, $v^0$ are uniquely set to be 0.

According to the materials design system of the present invention, the region $R_{relax}$ where lattice relaxation is taken into consideration, which is set in the aperiodic system $S^2$, can be appropriately changed during simulation. With this arrangement, the region $R_{relax}$ can be optimized, and the structure of the aperiodic system $S^2$ can be efficiently calculated. For this purpose, MD calculation combined with the method described in the second embodiment is also enabled.

In the materials design system of the present invention, even when the aperiodic system $S^2$ largely deforms as compared to the periodic system $S^1$, highly accurate calculation can be performed. This corresponds to a case wherein the deviation $\Delta r^2(i)_\alpha$ represented by equation (118) becomes large. When $\Delta r^2(i)_\alpha$ exceeds a predetermined value, the calculation accuracy of equations (106) and (108) may degrade. This problem can be avoided by setting dummy atoms in the periodic system $S^1$ and the reference system $S^0$ such that the deviation $\Delta r^2(i)_\alpha$ becomes small. The materials design system of the present invention can perform highly accurate calculation even when the aperiodic system $S^2$ largely deforms.

For this purpose, MD calculation combined with the method described in each of the first to third embodiments can also be performed. When the structural difference between the reference system $S^0$ and the periodic system $S^1$ becomes large because of, e.g., a large lattice vibration caused by the temperature effect (this corresponds to a case wherein the deviation $\Delta r^1(k0)_\alpha$ of equation (116) increases), the calculation accuracy of equations (90) and (91) may degrade. However, this problem can also be avoided by setting dummy atoms in the reference system $S^0$, as in processing for the periodic system $S^1$. Therefore, the materials design system of the present invention can execute MD calculation for the periodic system $S^1$ even when the lattice vibration caused by the temperature effect is large.

In MD calculation for the aperiodic system $S^2$, when the number $N^0$ of atoms per unit cell $U^0$ of the reference system $S^0$ is almost equal to the number $N^1$ of atoms per unit cell $U^1$ of the periodic system $S^1$, calculation for the periodic system $S^1$ need not always be performed. MD calculation may be executed while taking only the reference system $S^0$ and the aperiodic system $S^2$ into consideration. This method corresponds to the first embodiment.

In the 5th and 6th embodiments, only MD calculation has been described. However, the materials design system of the present invention can also execute MM (Molecular Mechanics) calculation. In this case, the mass m of an atom is set to be 1, and the velocity v is set to be 0. With this setting, MM calculation can be executed following the same procedures as in the description of 5th and 6th embodiments. In addition, since the reference system $S^0$ and the periodic system $S^1$ completely become equivalent by this processing, MM calculation for the periodic system $S^1$ can be omitted.

According to the materials design systems of the above-described fifth to seventh embodiments, the following effects can be obtained, unlike the prior art.

For the periodic system $S^1$,

Shortening of the computational time

For the aperiodic system $S^2$

Shortening of the computational time

Realization of calculation for an infinite system containing a completely isolated disorder (equivalent to the supercell method using a unit cell having an infinite size)

Realization of calculation using a real charge distribution for a system where the charge neutrality has been lost.

These effects will be sequentially described below.

Shortening of the computational time of MD calculation for the periodic system $S^1$ according to the fifth embodiment will be described first.

In MD calculation, most CPU time is spent to calculate the forces. When MD calculation for the periodic system $S^1$ is to be performed by the materials design system of the present invention, most calculation time is spent to calculate the sum $$\sum_{(k'\xi') \in R_{cut}}$$

of equation (91). This $$\sum_{(k'\xi') \in R_{cut}}$$

means that, when the force acting on the atom (k0) is to be calculated, the sum is calculated for atoms (k'ξ') in the region $R_{cut}$ (given as a sphere having the radius $R_{cut}$) centered on the atom (k0).

In equation (91), as the interaction with the atoms (k'ξ') outside the region $R_{cut}$, the interaction in the reference system $S^0$ is approximately used (this interaction is given by the first term $f^0(k0)_\alpha$).

This means that the real interaction in the periodic system $S^1$ is taken into consideration for atoms in the region $R_{cut}$, and the approximate interaction in which lattice vibration caused by the temperature effect is neglected is taken into consideration for atoms outside the region $R_{cut}$.

In the materials design system of the present invention, the region $R_{cut}$ is appropriately set, thereby realizing efficient MD calculation for the periodic system $S^1$ in the following manner. As for the atoms (k'ξ') intracting with the atom (k0), the number of the atoms (k'ξ') outside the region $R_{cut}$ is generally larger than that of the atoms (k'ξ') inside the region Rcut.

In equation (91), the calculation result for the reference system $S^0$ is used as the interaction with the atoms (k'ξ) outside the region Rcut. The amount of calculation of the force of the reference system $S^0$ is small because the unit cell $U^0$ is small. In addition, once calculation for the reference system $S^0$ is performed at the initial setting stage of MD calculation, calculation need not be performed anymore during repetitive calculation (FIG. 20).

For this reason, since the calculation result for the reference system $S^0$ is used for calculation of the force of the periodic system $S^1$, the time required for MD calculation for the periodic system $S^1$ can be largely shortened.

In the conventional method (supercell method), the calculation amount of MD calculation for the periodic system $S^1$ is estimated as $N^1 \times N^1 \times N_{all} \times N_{step}$. In the method of the present invention, the calculation amount is $N^1 \times N_{cut} \times N_{step}$ ($N_{cut}$ is the number of atoms contained in the region $R_{cut}$). Therefore, the calculation speed can be increased to $(N^1 \times N_{all})/N_{cut}$ times that of the conventional method in accordance with setting of the region $R_{cut}$.

The influence of approximation of equation (91) on the calculation accuracy will be described. Interatomic interactions are largely influenced by atoms at close positions. Therefore, equation (91) for introducing approximation only to the interactions with atoms at remote positions is plausible.

Equation (91) does not neglect the interactions with atoms outside the region $R_{cut}$ and only assumes that the atoms are fixed at equilibrium positions (neglect vibration caused by the temperature effect). Since the physical quantities (temperature, pressure, diffusion coefficient, and the like) which are normally calculated by MD calculation are macroquantities which are averaged for a long time, it is generally considered that the physical quantities are not influenced by approximation of equation (91).

In the materials design system of the present invention, the region $R_{cut}$ is appropriately set in consideration of the balance between the calculation accuracy required by the user and the calculation time, efficient MD calculation for the periodic system $S^1$ can be realized. In actual material design, it is important to execute MD calculation a number of times for a number of types of systems while changing the condition to obtain guidelines for materials design. Particularly in such a situation, the materials design system of the present invention particularly can exhibit the effect.

The effect of MD calculation for the aperiodic system $S^2$ according to the sixth embodiment will be described next. In the present invention, when MD calculation for the aperiodic system $S^2$ is to be performed, three systems, i.e., the reference system $S^0$, the periodic system $S^1$, and the aperiodic system $S^2$ are handled. The force $F^2(i)_\alpha$ of the aperiodic system $S^2$ is calculated using equation (103).

According to equation (103), $F^2(i)_\alpha$ is given by three terms, i.e., the force $F^1(i)_\alpha$ acting on an atom of the periodic system $S^1$ and the physical quantities $\Delta F^{2(a)}(i)_\alpha$ and $\Delta F^{2(b)}(i)_\alpha$ of the aperiodic system $S^2$. For $F^1(i)_\alpha$, the efficiency of calculation is increased by equation (91), as in MD calculation for the periodic system $S^1$.

Since $\Delta F^{2(a)}(i)_\alpha$ calculated by equation (107) is given by the physical quantity $f^1(k0)_\alpha$ of the periodic system $S^1$ and the sum for $N^{imp}$ ($<<N^2$) impurity atoms, the calculation amount of this term is very small. Finally, $\Delta F^{2(b)}(i)_\alpha$ is given by the sum for a difference amount $[\psi'(r^2|i,j)_\alpha - \psi'(r^1|i,j)_\alpha]$ of equation (108). Since the differential amount abruptly approaches 0 as the distance from the impurity atom increases, calculation of equation (108) rapidly converges.

Due to the above reason, the efficiency of calculation of $F^2(i)_\alpha$ is increased, so that the time required for MD calculation for the aperiodic system $S^2$ can be shortened.

In the conventional method (supercell method), the calculation amount of MD calculation for the aperiodic system $S^2$ is roughly estimated as $N_{SC} \times N_{SC} \times N_{all} \times N_{step}$. In the method of the present invention, the calculation amount is $(N^1 \times N_{cut} + N^2 \times N'_{cut}) \times N_{step}$ (where $N'_{cut}$ is the number of atoms contained in a region $R'_{cut}$ described in the description of the aperiodic system $S^2$ calculation unit 4-7).

$N_{SC}$, $N^1$, and $N^2$ are values on almost the same order and can be omitted. In the materials design system of the present invention, the calculation speed can be increased to about $(N_{SC} \times N_{all})/(N_{cut} + N'_{cut})$ times that of the supercell method in accordance with setting of the regions $R_{cut}$ and $R'_{cut}$.

In the first to fourth embodiments, only the reference system $S^0$ and the aperiodic system $S^2$ are handled. To the contrary, in the materials design systems of the fifth to seventh embodiments, the periodic system $S^1$ is taken into consideration in addition to the reference system $S^0$ and the aperiodic system $S^2$. Therefore, even when the periodic system has the unit cell $U^1$ ($N^1>>N^0$) with a large size because of lattice vibration caused by the temperature effect, efficient MD calculation for the aperiodic system $S^2$ can be realized.

The second and third effects of MD calculation for the aperiodic system $S^2$ will be described below. The "calculation for an infinite system containing a completely isolated disorder" and the "calculation using a real charge distribution for a system where the charge neutrality has been lost" are realized by describing the structure of the aperiodic system $S^2$ as a deviation from the periodic system $S^1$.

In the materials design system of the present invention, no periodic boundary condition is set for the aperiodic system $S^2$. For this reason, no interaction is present between disorders contained in different unit cells in the supercell method, so that each disorder can be handled as a completely isolated disorder. In the supercell method, when the disorder (impurity) has charges, artificial charges (generally, unique charges) must be assigned to each constituent atom to nullify the sum of charges per unit cell. This restriction is technically required because the energy diverges in a system whose total charges per unit cell are deviated from 0. Consequently, calculation using a real charge distribution cannot be performed by the supercell method. However, in the present invention, since the periodic boundary condition is not used for the aperiodic system $S^2$, calculation using the real charge distribution can be performed even for the aperiodic system $S^2$ where the charge neutrality has been lost.

According to the materials design system of the present invention, high-speed MD calculation for the periodic system $S^1$ and accurate and high-speed MD calculation for the aperiodic system $S^2$ can be realized.

As has been described above, according to the present invention, when the structural stability or dynamic behavior of a periodic system or an aperiodic system is to be analyzed in materials design, high-speed and accurate calculation (simulation) can be performed.

The present invention is not limited to the above-described embodiments. The respective units described in the embodiments can be realized not only by hardware but also by software. The method described in each embodiment can be stored, as a program that a computer can execute, in a recording medium such as a magnetic disk (a floppy disk, a hard disk, or the like), an optical disk (a CD-ROM, a DVD, or the like), or a semiconductor memory and distributed. In addition, various changes and modifications can be made within the spirit and scope of the present invention.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

I claim:

1. A materials design system which analyzes a structural stability or dynamic behavior of an infinite system (aperiodic system $S^2$) having a completely isolated local disorder at an atomic or molecular level, thereby assisting materials design, comprising:

a reference system $S^0$ processing unit for processing a physical quantity of an infinite system (reference system $S^0$) having no disorder, thereby defining the reference system $S^0$;

an aperiodic system $S^2$ processing unit for processing a physical quantity of said aperiodic system $S^2$ thereby defining the aperiodic system $S^2$, and a list for making constituent atoms of said reference system $S^0$ to correspond with those of said aperiodic system $S^2$ in one-to-one correspondence to describe a structure of said aperiodic system $S^2$ on the basis of a deviation from said reference system $S^0$;

a reference system $S^0$ calculation unit for calculating an energy of said reference system $S^0$ and a force acting on each atom or each molecule of said reference system $S^0$;

an aperiodic system $S^2$ calculation unit for calculating an energy of said aperiodic system $S^2$ and a force acting on each constituent atom of said aperiodic system $S^2$ using the energy of said reference system $S^0$ and the force acting on each constituent atom of said reference system $S^0$, which are calculated by said reference system $S^0$ calculation unit; and an aperiodic system MD calculation unit for repeatedly executing an MD calculation of the dynamic behavior of said aperiodic system $S^2$ using a calculation result from said aperiodic system $S^2$ calculation unit until a predetermined condition is met, wherein said aperiodic system MD calculation unit transfers the result of the MD calculation to said reference system $S^0$ processing unit and said aperiodic system $S^2$ processing unit each time the MD calculation is executed, so that the physical quantity of said reference system $S^0$ and aperiodic system $S^2$ are updated.

2. A system according to claim 1, further comprising, when an analysis (MD calculation) of the dynamic behavior of said aperiodic system $S^2$ is to be performed at a finite temperature (temperature T>0 K):

means for describing the structure of said aperiodic system $S^2$ as a deviation from said infinite system (periodic system $S^1$) having no local disorder and for describing a periodic system $S^1$ on a basis of a deviation from said infinite system (reference system $S^0$) which contains neither a local disorder nor considers vibration of atoms which is caused by a temperature effect, said means for describing the structure of said aperiodic system $S^2$ comprising:

a periodic system $S^1$ processing unit for processing a physical quantity of said periodic system $S^1$ thereby defining the periodic system $S^1$, and for processing a list for making constituent atoms of said reference system $S^0$ (the system in which lattice vibration is not taken into account) to correspond to those of said periodic system $S^1$ in one-to-one correspondence to describe a structure of said periodic system $S^1$ on the basis of a deviation from said reference system $S^0$, a periodic system $S^1$ calculation unit for calculating an energy of said periodic system $S^1$ and a force acting on each constituent atom of said periodic system $S^1$ using the energy of said reference system $S^0$ and the force acting on each constituent atom of said reference system $S^0$, which are calculated by said reference system $S^0$ calculation unit, and a periodic system MD calculation unit for repeatedly executing MD calculation using a calculation result from said aperiodic system $S^2$ calculation unit until a predetermined condition is met, thereby analyzing the dynamic behavior of said aperiodic system $S^2$ as a deviation from said periodic system $S^1$; and wherein said aperiodic system $S^2$ calculation unit calculates the energy of said aperiodic system $S^2$ and a force acting on each constituent atom of said aperiodic system $S^2$ by using the energy of said periodic system $S^1$ and the force acting on each constituent atom of said periodic system $S^1$, which are calculated by said periodic system $S^1$ calculation unit, wherein said aperiodic system MD calculation unit repeatedly executes the MD calculation of the structural stability of said aperiodic system $S^2$ by using a calculation result from said aperiodic system $S^2$ calculation unit until a predetermined condition is met, and wherein each time said periodic system MD calculation unit and said aperiodic system MD calculation unit execute MD calculations, they transfer results of the MD calculations to said periodic system $S^1$ and said aperiodic system $S^2$, thereby updating the physical quantities of said periodic system $S^1$ and said aperiodic system $S^2$, respectively.

3. A system according to claim 1, wherein said aperiodic system $S^2$ processing unit comprises means for changing, during simulation, a region where lattice relaxation of said aperiodic system $S^2$ is taken into consideration.

4. A system according to claim 1, wherein said reference system $S^0$ processing unit comprises means for setting a dummy atom or a dummy molecule in said reference system $S^0$.

5. The materials design system according to claim 1, further comprising an MM calculation unit for repeatedly executing MM calculations of the structural stability of said aperiodic reference system $S^2$ by using a calculation from said aperiodic system $S^2$ until a predetermined condition is met.

6. A materials design system which analyzes a dynamic behavior of atoms or molecules in infinite system (periodic system $S^1$) which has no local disorder but has vibration of atoms which is caused by a temperature effect, thereby assisting materials design, comprising:

a reference system $S^0$ processing unit for processing a physical quantity of an infinite system (reference system $S^0$) which neither contains a local disorder nor considers vibration of atoms which is caused by the temperature effect;

a periodic system $S^1$ processing unit for processing a physical quantity of said periodic system $S^1$ and a list for making constituent atoms of said reference system $S^0$ to correspond with those of said periodic system $S^1$ in one-to-one correspondence to describe a structure of said periodic system $S^1$ on the basis of a deviation from said reference system $S^0$;

a reference system $S^0$ calculation unit for calculating an energy of said reference system $S^0$ and a force acting on each atom or each molecule of said reference system $S^0$;

a periodic system $S^1$ calculation unit for calculating an energy of said periodic system $S^1$ and a force acting on each constituent atom of said periodic system $S^1$, by partly substituting said energy and force of said periodic system $S^1$ for said energy and force of said reference system $S^0$, which are calculated by said reference system $S^0$ calculation unit; and a periodic system $S^1$ MD calculation unit for repeatedly executing MD calculations of the dynamic behavior of said periodic system $S^1$ until a predetermined condition is met, wherein the MD calculation unit transfers the result of the MD calculations to said periodic system $S^1$ processing unit each time the MD calculation is executed so that the physical quantities of said periodic system $S^1$ are updated.

7. A system according to claim 6, wherein said reference system $S^0$ processing unit comprises means for setting a dummy atom or a dummy molecule in said reference system $S^0$.

8. A storage medium which stores a computer program for causing a computer system to analyze a structural stability or dynamic behavior of an infinite crystal system (aperiodic system $S^2$) having a completely isolated local disorder at an atomic or molecular level to assist materials design, comprising:

a reference system $S^0$ processing procedure code of processing a physical quantity of an infinite system (reference system $S^0$) having no disorder, thereby defining the reference system $S^0$;

an aperiodic system $S^2$ processing procedure code of processing a physical quantity of said aperiodic system $S^2$ thereby defining the aperiodic system $S^2$ and for processing a list of making constituent atoms of said reference system $S^0$ to correspond with those of said aperiodic system $S^2$ in one-to-one correspondence to describe a structure of said aperiodic system $S^2$ on the basis of a deviation from said reference system $S^0$;

a reference system $S^0$ calculation procedure code of calculating an energy of said reference system $S^0$ and a force acting on each atom or each molecule of said reference system $S^0$;

an aperiodic system $S^2$ calculation procedure code of calculating an energy of said aperiodic system $S^2$ and a force acting on each constituent atom of said aperiodic system $S^2$ using the energy of said reference system $S^0$ and the force acting on each constituent atom of said reference system $S^0$, which are calculated by said reference system $S^0$ calculation procedure code; and an aperiodic system MD calculation procedure code for repeatedly executing an MD calculation of the dynamic behavior of said aperiodic system $S^2$ using a calculation result from said aperiodic system $S^2$ calculation procedure code until a predetermined condition is met, wherein said aperiodic system MD calculation procedure code transfers the result of the MD calculation to said reference system $S^0$ procedure code and said aperiodic system $S^2$ procedure code each time the MD calculation is executed, so that the physical quantity of said reference system $S^0$ and aperiodic system $S^2$ are updated.

9. A medium according to claim 8, further comprising, when an analysis (MD calculation) of the dynamic behavior of said aperiodic system $S^2$ is to be performed at a finite temperature (temperature T>0 K):

a procedure code of describing the structure of said aperiodic system $S^2$ as a deviation from said infinite system (periodic system $S^1$) having no local disorder and for describing a periodic system $S^1$ on a basis of a deviation from said infinite system (reference system $S^0$) which contains neither a local disorder nor considers vibration of atoms which is caused by the temperature effect, said procedure code of describing the structure of said aperiodic system $S^2$ comprising, a periodic system $S^1$ processing procedure code of processing a physical quantity of said periodic system $S^1$ thereby defining the periodic system $S^1$, and for processing a list for making constituent atoms of a reference system $S^0$ (the system in which lattice vibration is not taken into account) to correspond to those of said periodic system $S^1$ in one-to-one correspondence to describe a structure of said periodic system $S^1$ on the basis of a deviation from said reference system $S^0$, a periodic system $S^1$ calculation procedure code of calculating an energy of said periodic system $S^1$ and a force acting on each constituent atom of said periodic system $S^1$ using the energy of said reference system $S^0$ and the force acting on each constituent atom of said reference system $S^0$, which are calculated by said reference system $S^0$ calculation procedure code, and a periodic system MD calculation procedure code for repeatedly executing MD calculation using a calculation result from said periodic system $S^2$ calculation procedure code until a predetermined condition is met, thereby analyzing the dynamic behavior of said aperiodic system $S^2$ as a deviation from said periodic system $S^1$; and wherein said aperiodic system $S^2$ calculation procedure code calculates the energy of said aperiodic system $S^2$ and a force acting on each constituent atom of said aperiodic system $S^2$ by using the energy of said periodic system $S^1$ and the force acting on each constituent atom of said periodic system $S^1$, which are calculated by said periodic system $S^1$ calculation procedure code, wherein said aperiodic system MD calculation procedure code repeatedly executes the MD calculation of the structural stability of said aperiodic system $S^2$ by using a calculation result from said aperiodic system $S^2$ calculation procedure code until a predetermined condition is met, and wherein each time said periodic system MD calculation procedure code and said aperiodic system MD calculation procedure code execute MD calculations, they transfer results of the MD calculations to said periodic system $S^1$ and said aperiodic system $S^2$, thereby updating the physical quantities of said periodic system $S^1$ and said aperiodic system $S^2$, respectively.

10. A medium according to claim 8, wherein said aperiodic system $S^2$ processing procedure code comprises a procedure code of changing, during simulation, a region where lattice relaxation of said aperiodic system $S^2$ is taken into consideration.

11. A medium according to claim 8, wherein said reference system $S^0$ processing procedure code comprises a procedure code of setting a dummy atom or a dummy molecule in said reference system $S^0$.

12. The storage medium according to claim 8, further comprising an MM calculation procedure code for repeatedly executing MM calculations of the structural stability of said aperiodic reference system $S^2$ by using a calculation from said aperiodic system $S^2$ until a predetermined condition is met.

13. A storage medium which stores a computer program for causing a computer system to analyze a dynamic behavior of atoms or molecules in an infinite system (periodic system $S^1$) which has no local disorder but has vibration of atoms which is caused by a temperature effect, thereby assisting materials design, comprising:

a reference system $S^0$ processing procedure code of processing a physical quantity of an infinite system (reference system $S^0$) which neither contains a local disorder nor considers the vibration of atoms which is caused by the temperature effect;

a periodic system $S^1$ processing procedure code of processing a physical quantity of said periodic system $S^1$ and a list for making constituent atoms of said reference system $S^0$ to correspond with those of said periodic system $S^1$ in one-to-one correspondence to describe a structure of said periodic system $S^1$ on the basis of a deviation from said reference system $S^0$;

a reference system $S^0$ calculation procedure code of calculating an energy of said reference system $S^0$ and a force acting on each atom or each molecule of said reference system $S^0$; and a periodic system calculation procedure code of calculating an energy of said periodic system $S^1$ and a force acting on each constituent atom of said periodic system $S^1$ by partly substituting said energy and force of said periodic system $S^1$ for said energy and force of said reference system $S^0$, which are calculated by said reference system $S^0$ calculation procedure code; and a periodic system $S^1$ MD calculation procedure code for repeated executing MD calculations of the dynamic behavior of said periodic system $S^1$ until a predetermined conditions is met, wherein the MD calculation procedure code transfers the result of the MD calculations to said periodic system $S^1$ calculation procedure code each time the MD calculation is executed so that the physical quantities of said periodic system $S^1$ are updated.

14. A medium according to claim 13, wherein said reference system $S^0$ processing procedure code comprises a procedure code of setting a dummy atom or a dummy molecule in said reference system $S^0$.

* * * * *

UNITED STATES PATENT AND TRADEMARK OFFICE
CERTIFICATE OF CORRECTION

PATENT NO. : 6,038,514
DATED : March 14, 2000
INVENTOR(S) : Hanae NOZAKI

It is certified that error appears in the above-identified patent and that said Letters Patent is hereby corrected as shown below:

Claim 13, Col. 59, line 5, after "conditions", should read --condition--.

Signed and Sealed this

Seventeenth Day of April, 2001

Attest:

NICHOLAS P. GODICI

*Attesting Officer*  *Acting Director of the United States Patent and Trademark Office*